US012570641B2

(12) United States Patent
Clark et al.

(10) Patent No.: US 12,570,641 B2
(45) Date of Patent: Mar. 10, 2026

(54) SOLID FORMS OF A CDK4 INHIBITOR

(71) Applicant: Pfizer Inc., New York, NY (US)

(72) Inventors: Wesley Dewitt Clark, Gales Ferry, CT (US); Judith Gail Deal, Wildomar, CA (US); Brian Matthew Samas, Niantic, CT (US)

(73) Assignee: Pfizer Inc., New York, NY (US)

(*) Notice: Subject to any disclaimer, the term of this patent is extended or adjusted under 35 U.S.C. 154(b) by 443 days.

(21) Appl. No.: 18/245,039

(22) PCT Filed: Sep. 13, 2021

(86) PCT No.: PCT/IB2021/058320
§ 371 (c)(1),
(2) Date: Mar. 13, 2023

(87) PCT Pub. No.: WO2022/058871
PCT Pub. Date: Mar. 24, 2022

(65) Prior Publication Data

US 2023/0357211 A1 Nov. 9, 2023

Related U.S. Application Data

(60) Provisional application No. 63/240,268, filed on Sep. 2, 2021, provisional application No. 63/078,636, filed on Sep. 15, 2020.

(51) Int. Cl.
*C07D 405/14* (2006.01)

(52) U.S. Cl.
CPC ........ *C07D 405/14* (2013.01); *C07B 2200/13* (2013.01)

(58) Field of Classification Search
None
See application file for complete search history.

(56) References Cited

FOREIGN PATENT DOCUMENTS

| | | | |
|---|---|---|---|
| CN | 105111191 | A | 12/2015 |
| WO | 2011/014515 | A1 | 2/2011 |
| WO | 2014/160017 | A1 | 10/2014 |
| WO | 2018/013867 | A1 | 1/2018 |
| WO | 2019/207463 | A1 | 10/2019 |
| WO | WO 2019/207463 | * | 10/2019 |
| WO | 2022/058871 | A1 | 3/2022 |

OTHER PUBLICATIONS

Golub et al., Science, vol. 286, Oct. 15, 1999, pp. 531-537.*
Mount Sinai "Deciphering the Mechanism of Resistance to CDK4/6 Inhibitors in Mulitple Tumor Types" 2022.*
Knudsen et al. "The Strange Case of CDK4/6 Inhibitors: Mechanisms, Resistance, and Combination Strategies" 2017.*
Aaltonen, J., et al., "Solid form screening—A review," 2009, European Journal of Pharmaceutics and Biopharmaceutics, 71:23-37.
International Preliminary Report on Patentability issued in PCT/IB2021/058320; mailed on Mar. 30, 2023; 12 pp.
Mitkina, L.I., et al., "Stress studies and photostability as part of pharmaceutical drug development data," 2015, Gazette of the Scientific Center for Expertise of Medical Products, 2:9-12.
Morissette, S., et al., "High-throughput crystallization: polymorphs, salts, co-crystals and solvates of pharmaceutical solids," Advanced Drug Delivery Reviews, 2004, 56:275-300.
Tian, F., et al., "Factors affecting crystallization of hydrates," Journal of Pharmacy and Pharmacology, 2010, 62:1534-1546.
Variankaval, N. and Cote, A., "From Form to Function: Crystallization of Active Pharmaceutical Ingredients," AIChE, 2008, 54(7):1682-1688.
Byrn, Stephen et al., "Pharmaceutical Solids: A Strategic Approach to Regulatory Considerations", Pharmaceutical Research, 1995, 945-954, 12(7).
Caira, Mino R., "Crystalline Polymorphism of Organic Compounds", Topics in Current Chemistry, 1998, 163-208, 198.
Yu, Lian, "Amorphous pharmaceutical solids: preparation, characterization and stabilization", Advanced Drug Delivery Reviews, 2001, 27-42, 48.
PCT Search Report, PCT/IB2021/058320, Mar. 11, 2022.
PCT Written Opinion, PCT/IB2021/058320, Mar. 11, 2022.
Sugimoto, Isao & Takahashi, Yoshiteru, "Solvates, amorphous solids and pharmaceutical formulations", Journal of the Society of Powder Technology, 1985, 86-97, 22(2), Japan. English translation provided.
Takada, "Drug Substance Form Screening and Selection during the Drug Discovery Phase", API form screening and selection in drug discovery stage, Pharm Stage, 2007, 20-25, 6(10). English translation provided.
Ashizawa, Polymorphism and Crystallization Science of Pharmaceuticals, "Examples of Pseudo-crystalline Polymorphs (Hydrates and Solvates)", Publisher: Maruzen Planet Co., Ltd., 2002, Section 1, 273, 278 & 305-317. English translation provided.

* cited by examiner

*Primary Examiner* — Danah Al-Awadi
(74) *Attorney, Agent, or Firm* — Carmen K. Robinson

(57) ABSTRACT

This invention relates to crystalline and amorphous forms of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol, to pharmaceutical compositions comprising such solid forms, and to use of such solid forms and pharmaceutical compositions for the treatment of cancer.

20 Claims, 17 Drawing Sheets

SOLID FORMS OF A CDK4 INHIBITOR

CROSS-REFERENCE TO RELATED APPLICATIONS

This application is the U.S. National Phase under 35 U.S.C. § 371 of International Patent Application No. PCT/IB2021/058320 filed Sep. 13, 2021, which claims the benefit of priority to U.S. Provisional Application No. 63/240,268, filed on Sep. 2, 2021, and U.S. Provisional Application No. 63/078,636, filed on Sep. 15, 2020, the contents of which are incorporated by reference herein in their entirety.

BACKGROUND OF THE INVENTION

Field of the Invention

This invention relates to solid forms of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (also referred to herein as PF-07220060), to pharmaceutical compositions comprising such solid forms, and to use of such solid forms and pharmaceutical compositions for the treatment of cancer.

Description of Related Art

The compound 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060) is a potent inhibitor of cyclin dependent kinase 4 (CDK4), having the structure:

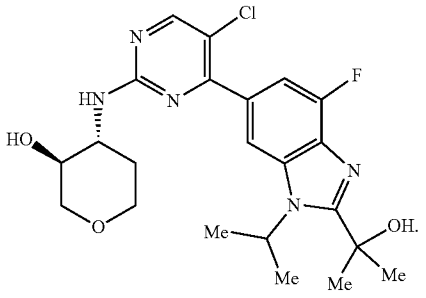 [SMILES: CC(C)n1c(C(C)(C)O)nc2c(F)cc(-c3nc(N[C@@H]4CCOC[C@H]4O)ncc3Cl)cc21]

Preparation of PF-07220060, isolated as a crystalline hydrate (Form 1), is disclosed in International Patent Publication No. WO 2019/207463 and U.S. Pat. No. 10,233,188, the contents of each of which are incorporated herein by reference in their entirety.

The present invention provides solid forms of PF-07220060 having desirable properties, such as high crystallinity, high purity, low hygroscopicity, favorable dissolution or mechanical properties, manufacturability, and/or favorable stability.

BRIEF SUMMARY OF THE INVENTION

The present invention provides solid forms of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060).

In some aspects and embodiments, the invention provides a crystalline form of PF-07220060 monohydrate (Form 2), as further described herein.

In one aspect, the invention provides a crystalline form of PF-07220060 monohydrate (Form 2) having:

(1) a powder X-ray diffraction (PXRD) pattern (2θ) comprising: (a) one, two, three, four, five, or more than five peaks selected from the group consisting of the peaks in Table 1 in ° 2θ±0.2°2θ; or (b) peaks at 2θ values essentially the same as in FIG. 1;

(2) a Raman spectrum comprising: (a) one, two, three, four, five, or more than five wavenumber ($cm^{-1}$) values selected from the group consisting of the values in Table 2 in $cm^{-1}$±2 $cm^{-1}$; or (b) wavenumber ($cm^{-1}$) values essentially the same as in FIG. 2;

(3) a $^{13}C$ solid state NMR spectrum (ppm) comprising: (a) one, two, three, four, five, or more than five resonance (ppm) values selected from the group consisting of the values in Table 3 in ppm±0.2 ppm; or (b) resonance (ppm) values essentially the same as in FIG. 3; or (4) a $^{19}F$ solid state NMR spectrum (ppm) comprising: (a) one or two resonance (ppm) values selected from the group consisting of the values in Table 4 in ppm±0.2 ppm; or (b) resonance (ppm) values essentially the same as in FIG. 4;

or any combination of two or more of (1)(a)-(b), (2)(a)-(b), (3)(a)-(b), and (4)(a)-(b), provided they are not inconsistent with each other.

In another aspect, the invention provides a crystalline form of PF-07220060 monohydrate (Form 2) having a powder X-ray diffraction (PXRD) pattern comprising peaks at 2θ values of: 9.6, 11.8 and 14.7°2θ±0.2°2θ.

In another aspect, the invention provides a crystalline form of PF-07220060 monohydrate (Form 2) having a Raman spectrum comprising wavenumber ($cm^{-1}$) values of: 1484, 1555 and 1587 $cm^{-1}$±2 $cm^{-1}$.

In another aspect, the invention provides a crystalline form of PF-07220060 monohydrate (Form 2) having a $^{13}C$ solid state NMR spectrum comprising resonance (ppm) values of: 22.8 and 163.0 ppm±0.2 ppm.

In a further aspect, the invention provides a crystalline form of PF-07220060 monohydrate (Form 2) having a $^{19}F$ solid state NMR spectrum comprising resonance (ppm) values of: −126.1 and −125.6 ppm±0.2 ppm.

In another aspect, the invention provides a crystalline form of PF-07220060 monohydrate (Form 2) having: (a) a powder X-ray diffraction (PXRD) pattern comprising peaks at 2θ values of: 9.6, 11.8 and 14.7°2θ±0.2°2θ; (b) a Raman spectrum comprising wavenumber ($cm^{-1}$) values of: 1484, 1555 and 1587 $cm^{-1}$ 2 $cm^{-1}$; (c) a $^{13}C$ solid state NMR spectrum comprising resonance (ppm) values of: 22.8 and 163.0 ppm±0.2 ppm; or (d) a $^{19}F$ solid state NMR spectrum comprising resonance (ppm) values of: −126.1 and −125.6 ppm±0.2 ppm; or any combination of two or more of (a), (b), (c) and (d).

In some aspects and embodiments, the invention provides an anhydrous crystalline form of PF-07220060 (Form 6), according to the aspects or embodiments as further described herein.

In other aspects and embodiments, the invention provides an anhydrous crystalline form of PF-07220060 (Form 11), according to the aspects or embodiments as further described herein.

In further aspects and embodiments, the invention provides an amorphous form of PF-07220060 (Form 8), according to the aspects or embodiments as further described herein.

In another aspect, the invention provides a pharmaceutical composition comprising a crystalline or amorphous form of PF-07220060, according to any of the aspects or embodiments described herein, and a pharmaceutically acceptable carrier or excipient.

In preferred embodiments, the pharmaceutical composition comprises crystalline PF-07220060 monohydrate (Form 2). In some embodiments, the pharmaceutical composition comprises anhydrous crystalline PF-07220060 (Form 6). In some embodiments, the pharmaceutical composition comprises anhydrous crystalline PF-07220060 (Form 11). In some embodiments, the pharmaceutical composition comprises amorphous PF-07220060 (Form 8).

In another aspect, the invention provides a method of treating cancer in a subject in need thereof, comprising administering to the subject a therapeutically effective amount of a crystalline or amorphous form of PF-07220060, or a pharmaceutical composition comprising a crystalline or amorphous form of PF-07220060, according to any of the aspects or embodiments described herein.

In another aspect, the invention provides use of a crystalline or amorphous form of PF-07220060, or a pharmaceutical composition comprising a crystalline or amorphous form of PF-07220060, according to any of the aspects or embodiments described herein, for the treatment of cancer.

In another aspect, the invention provides use of a crystalline or amorphous form of PF-07220060, or a pharmaceutical composition comprising a crystalline or amorphous form of PF-07220060, according to any of the aspects or embodiments described herein, in the manufacture of a medicament for the treatment of cancer.

In preferred embodiments of the foregoing methods and uses, the method or use comprises crystalline PF-07220060 monohydrate (Form 2). In some embodiments, the method or use comprises anhydrous crystalline PF-07220060 (Form 6). In some embodiments, the method or use comprises anhydrous crystalline PF-07220060 (Form 11). In some embodiments, the method or use comprises amorphous PF-07220060 (Form 8).

In another aspect, the invention provides a crystalline or amorphous form of PF-07220060, or a pharmaceutical composition comprising a crystalline or amorphous form of PF-07220060, according to any of the aspects or embodiments described herein, for use in the treatment of cancer. In preferred embodiments, the crystalline form is crystalline PF-07220060 monohydrate (Form 2). In some embodiments, the crystalline form is anhydrous crystalline PF-07220060 (Form 6). In some embodiments, the crystalline form is anhydrous crystalline PF-07220060 (Form 11). In some embodiments, the amorphous form is amorphous PF-07220060 (Form 8).

DETAILED DESCRIPTION OF THE INVENTION

Figure 1:
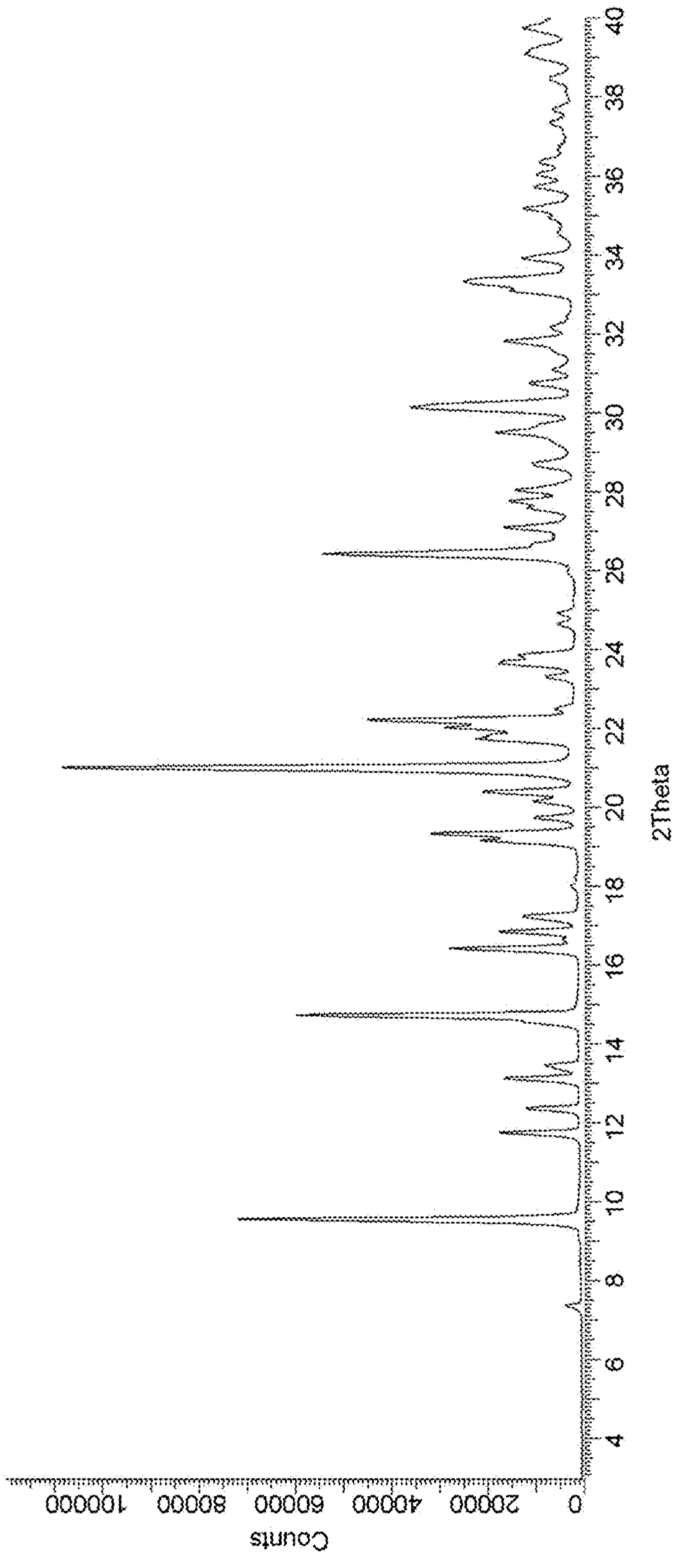
FIG. 1. PXRD pattern of crystalline PF-07220060 monohydrate (Form 2).

The present invention may be understood more readily by reference to the following detailed description of the embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

The invention described herein may be suitably practiced in the absence of any element(s) not specifically disclosed herein. Thus, for example, in each instance herein any of the terms "comprising", "consisting essentially of", and "consisting of" may be replaced with either of the other two terms.

As used herein, the singular form "a", "an", and "the" include plural references unless indicated otherwise. For example, "a" substituent includes one or more substituents.

The invention described herein suitably may be practiced in the absence of any element(s) not specifically disclosed herein. Thus, for example, in each instance herein any of the terms "comprising", "consisting essentially of", and "consisting of" may be replaced with either of the other two terms.

The term "about" means having a value falling within an accepted standard of error of the mean, when considered by one of ordinary skill in the art, typically such as plus or minus (±) 10%, unless otherwise indicated.

As used herein, the term "essentially the same" means that variability typical for the particular method is taken into account. For example, with reference to powder X-ray diffraction (PXRD) peak positions, the term "essentially the same" means that typical variability in peak position and intensity are taken into account. One skilled in the art will appreciate that the peak positions (2θ) will show some variability, typically as much as ±0.2° (2θ) for crystalline forms, or ±0.5° (2θ) for amorphous forms. Further, one skilled in the art will appreciate that relative peak intensities will show inter-apparatus variability, as well as variability due to the degree of crystallinity, preferred orientation, prepared sample surface, and other factors known to those skilled in the art and should be taken as qualitative measures only. Similarly, Raman spectrum wavenumber ($cm^{-1}$) values show variability, typically as much as ±2 $cm^{-1}$, while $^{13}C$ and $^{19}F$ solid state NMR spectrum (ppm) show variability, typically as much as ±0.2 ppm for crystalline forms, or ±0.5 ppm for amorphous forms.

The term "amorphous" as used herein, refers to a solid substance which (1) lacks order in three dimensions, or (2) exhibits order in less than three dimensions, order only over short distances (e.g., less than 10 Å), or both. Amorphous solids give diffuse PXRD patterns typically comprising one or two broad peaks.

The term "crystalline" as used herein, means having a regularly repeating arrangement of molecules or external face planes. Crystalline forms may differ with respect to thermodynamic stability, physical parameters, x-ray structure and preparation processes.

The terms "polymorph" or "polymorphic" refers to a crystalline form of a compound with a distinct spatial lattice arrangement as compared to other crystalline forms of the same compound.

The term "solvate" describes a molecular complex comprising a compound (e.g., the active pharmaceutical ingredient (API) of a drug product) and a stoichiometric or non-stoichiometric amount of one or more solvent molecules (e.g., water or ethanol). When the solvent is tightly bound to the compound, the resulting complex will have a well-defined stoichiometry that is independent of humidity. When, however, the solvent is weakly bound, as in channel solvates and hygroscopic compounds, the solvent content will be dependent on humidity and drying conditions. In such cases the complex will often be non-stoichiometric.

The term "hydrate" describes a solvate comprising the compound and a stoichiometric or non-stoichiometric amount of water. A "monohydrate" is a hydrate comprising one molecule of water per molecule of compound (i.e., a 1:1 stoichiometry of water to compound).

The expression "substantially pure" means that the crystalline or amorphous form described as substantially pure comprises less than 5%, preferably less than 3%, and more preferably less than 1% by weight of impurities, including any other physical form of the compound. Alternatively, the crystalline or amorphous form described as substantially pure may be expressed as >95% pure, preferably >97% pure, and more preferably >99% pure, in each case by weight of impurities, including any other physical form of the compound.

The crystalline and amorphous forms of PF-07220060 described herein may be characterized by the following methods: (1) powder X-ray diffraction (PXRD) (2θ); (2) Raman spectroscopy ($cm^{-1}$); (3)$^{13}C$ solid state NMR spectroscopy (ppm); (4)$^{19}F$ solid state NMR spectroscopy (ppm); or (5) differential scanning calorimetry (DSC) scan (Tg ° C.); or any combination of two or more of methods (1), (2), (3), (4) and (5).

In each of the aspects and embodiments herein that are characterized by PXRD, the PXRD peaks were collected using CuKα radiation at 1.5418λ.

Such solid forms may be further characterized by additional techniques, such as Fourier transform infrared spectroscopy (FTIR), thermogravimetric analysis (TGA) or differential thermal analysis (DTA).

In a preferred aspect, the invention provides a crystalline form of PF-07220060 monohydrate (Form 2). In some embodiments the crystalline form of PF-07220060 monohydrate (Form 2) is characterized by its powder X-ray diffraction (PXRD) pattern. In other embodiments, the crystalline form of PF-07220060 monohydrate (Form 2) is characterized by its Raman spectrum. In other embodiments, the crystalline form of PF-07220060 monohydrate (Form 2) is characterized by its $^{13}C$ solid state NMR spectrum. In still other embodiments, the crystalline form of PF-07220060 monohydrate (Form 2) is characterized by its $^{19}F$ solid state NMR spectrum.

In further embodiments, crystalline PF-07220060 monohydrate (Form 2) is characterized by any combination of two or more of these methods. Exemplary combinations including two or more of the following are provided herein: powder X-ray diffraction (PXRD) pattern (2θ); Raman spectrum wavenumber values ($cm^{-1}$); $^{13}C$ solid state NMR spectrum (ppm); or $^{19}F$ solid state NMR spectrum (ppm). In some embodiments crystalline PF-07220060 monohydrate (Form 2) is characterized by PXRD and Raman. In other embodiments, crystalline PF-07220060 monohydrate (Form 2) is characterized by PXRD and $^{13}C$ solid state NMR. In other embodiments, the crystalline PF-07220060 monohydrate (Form 2) is characterized by PXRD and $^{19}F$ solid state NMR. In other embodiments the crystalline PF-07220060 monohydrate (Form 2) is characterized by $^{19}F$ solid state NMR and Raman. In other embodiments crystalline PF-07220060 monohydrate (Form 2) is characterized by $^{19}F$ solid state NMR and $^{13}C$ solid state NMR. In other embodiments crystalline PF-07220060 monohydrate (Form 2) is characterized by PXRD, Raman and $^{13}C$ solid state NMR. In other embodiments crystalline PF-07220060 monohydrate (Form 2) is characterized by PXRD, Raman and $^{19}F$ solid state NMR.

In one aspect, the invention provides a crystalline form of PF-07220060 monohydrate (Form 2) characterized by a powder X-ray diffraction (PXRD) pattern.

In one embodiment, the invention provides a crystalline form of PF-07220060 monohydrate (Form 2) having a powder X-ray diffraction (PXRD) pattern comprising peaks at 2θ values of: 9.6, 11.8 and 14.7°2θ±0.2°2θ.

In one embodiment, the invention provides a crystalline form of PF-07220060 monohydrate (Form 2) having a powder X-ray diffraction (PXRD) pattern comprising peaks at 2θ values of: 9.6, 11.8, 12.4 and 14.7°2θ±0.2°2θ.

In one embodiment, the invention provides a crystalline form of PF-07220060 monohydrate (Form 2) having a powder X-ray diffraction (PXRD) pattern comprising peaks at 2θ values of: 9.6, 11.8, 14.7 and 21.0°2θ±0.2°2θ.

In another embodiment, the invention provides a crystalline form of PF-07220060 monohydrate (Form 2) having a powder X-ray diffraction (PXRD) pattern comprising peaks at 2θ values of: 9.6, 11.8, 12.4, 14.7 and 21.0°2θ±0.2°2θ.

In one embodiment, the invention provides a crystalline form of PF-07220060 monohydrate (Form 2) having a powder X-ray diffraction (PXRD) pattern comprising peaks at 2θ values of: 9.6, 11.8 and 14.7°2θ±0.2°2θ; and one or two peaks selected from the group consisting of: 12.4 and 21.0°2θ±0.2°2θ.

In another embodiment, the invention provides a crystalline form of PF-07220060 monohydrate (Form 2) having a PXRD pattern comprising three or more peaks at 20 values selected from the group consisting of: 9.6, 11.8, 12.4, 14.7 and 21.0°2θ±0.2° 2θ.

In another embodiment, the invention provides a crystalline form of PF-07220060 monohydrate (Form 2) having a PXRD pattern comprising: (a) one, two, three, four, five, or more than five peaks selected from the group consisting of the peaks in Table 1 in ° 2θ±0.2°2θ; or (b) peaks at 2θ values essentially the same as in FIG. 1.

In another aspect, the invention provides a crystalline form of PF-07220060 monohydrate (Form 2) characterized by a Raman spectrum.

In one embodiment, the invention provides a crystalline form of PF-07220060 monohydrate (Form 2) having a Raman spectrum comprising wavenumber ($cm^{-1}$) values of: 1484, 1555 and 1587 $cm^{-1}$±2 $cm^{-1}$.

In one embodiment, the invention provides a crystalline form of PF-07220060 monohydrate (Form 2) having a Raman spectrum comprising wavenumber ($cm^{-1}$) values of: 1387, 1484, 1555 and 1587 $cm^{-1}$±2 $cm^{-1}$.

In another embodiment, the invention provides a crystalline form of PF-07220060 monohydrate (Form 2) having a Raman spectrum comprising wavenumber ($cm^{-1}$) values of: 1395, 1484, 1555 and 1587 $cm^{-1}$±2 $cm^{-1}$.

In another embodiment, the invention provides a crystalline form of PF-07220060 monohydrate (Form 2) having a Raman spectrum comprising wavenumber ($cm^{-1}$) values of: 1387, 1395, 1484, 1555 and 1587 $cm^{-1}$±2 $cm^{-1}$.

In one embodiment, the invention provides a crystalline form of PF-07220060 monohydrate (Form 2) having a Raman spectrum comprising wavenumber ($cm^{-1}$) values of: 1484, 1555 and 1587 $cm^{-1}$±2 $cm^{-1}$; and one or two peaks selected from the group consisting of: 1387 and 1395 $cm^{-1}$±2 $cm^{-1}$.

In one embodiment, the invention provides a crystalline form of PF-07220060 monohydrate (Form 2) having a Raman spectrum comprising: (a) one, two, three, four, five, or more than five wavenumber ($cm^{-1}$) values selected from the group consisting of the values in Table 2 in $cm^{-1}$±2 $cm^{-1}$; or (b) wavenumber ($cm^{-1}$) values essentially the same as in FIG. 2.

In another aspect, the invention provides a crystalline form of PF-07220060 monohydrate (Form 2) characterized by a $^{13}C$ solid state NMR spectrum.

In one embodiment, the invention provides a crystalline form of PF-07220060 monohydrate (Form 2) having a $^{13}C$ solid state NMR spectrum comprising resonance (ppm) values of: 22.8 and 163.0 ppm±0.2 ppm.

In one embodiment, the invention provides a crystalline form of PF-07220060 monohydrate (Form 2) having a $^{13}C$ solid state NMR spectrum comprising resonance (ppm) values of: 22.8, 50.3 and 163.0 ppm±0.2 ppm.

In one embodiment, the invention provides a crystalline form of PF-07220060 monohydrate (Form 2) having a $^{13}C$ solid state NMR spectrum comprising resonance (ppm) values of: 22.8, 109.8 and 163.0 ppm±0.2 ppm.

In another embodiment, the invention provides a crystalline form of PF-07220060 monohydrate (Form 2) having a $^{13}C$ solid state NMR spectrum comprising resonance (ppm) values of: 22.8, 129.1 and 163.0 ppm±0.2 ppm.

In one embodiment, the invention provides a crystalline form of PF-07220060 monohydrate (Form 2) having a $^{13}C$ solid state NMR spectrum comprising resonance (ppm) values of: 22.8 and 163.0 ppm±0.2 ppm; and one, two or three resonance (ppm) values selected from the group consisting of: 50.3, 109.8 and 129.1 ppm±0.2 ppm.

In another embodiment, the invention provides a crystalline form of PF-07220060 monohydrate (Form 2) having a $^{13}C$ solid state NMR spectrum (ppm) comprising: (a) one, two, three, four, five, or more than five resonance (ppm) values selected from the group consisting of the values in Table 3 in ppm±0.2 ppm; or (b) resonance (ppm) values essentially the same as in FIG. 3.

In another aspect, the invention provides a crystalline form of PF-07220060 monohydrate (Form 2) characterized by a $^{19}F$ solid state NMR spectrum.

In one embodiment, the invention provides a crystalline form of PF-07220060 monohydrate (Form 2) having a $^{19}F$ solid state NMR spectrum comprising a resonance (ppm) value of: −126.1 ppm±0.2 ppm.

In another embodiment, the invention provides a crystalline form of PF-07220060 monohydrate (Form 2) having a $^{19}F$ solid state NMR spectrum comprising a resonance (ppm) value of: −125.6 ppm±0.2 ppm.

In a preferred embodiment, the invention provides a crystalline form of PF-07220060 monohydrate (Form 2) having a $^{19}F$ solid state NMR spectrum comprising resonance (ppm) values of: −126.1 and −125.6 ppm±0.2 ppm.

Figure 4:
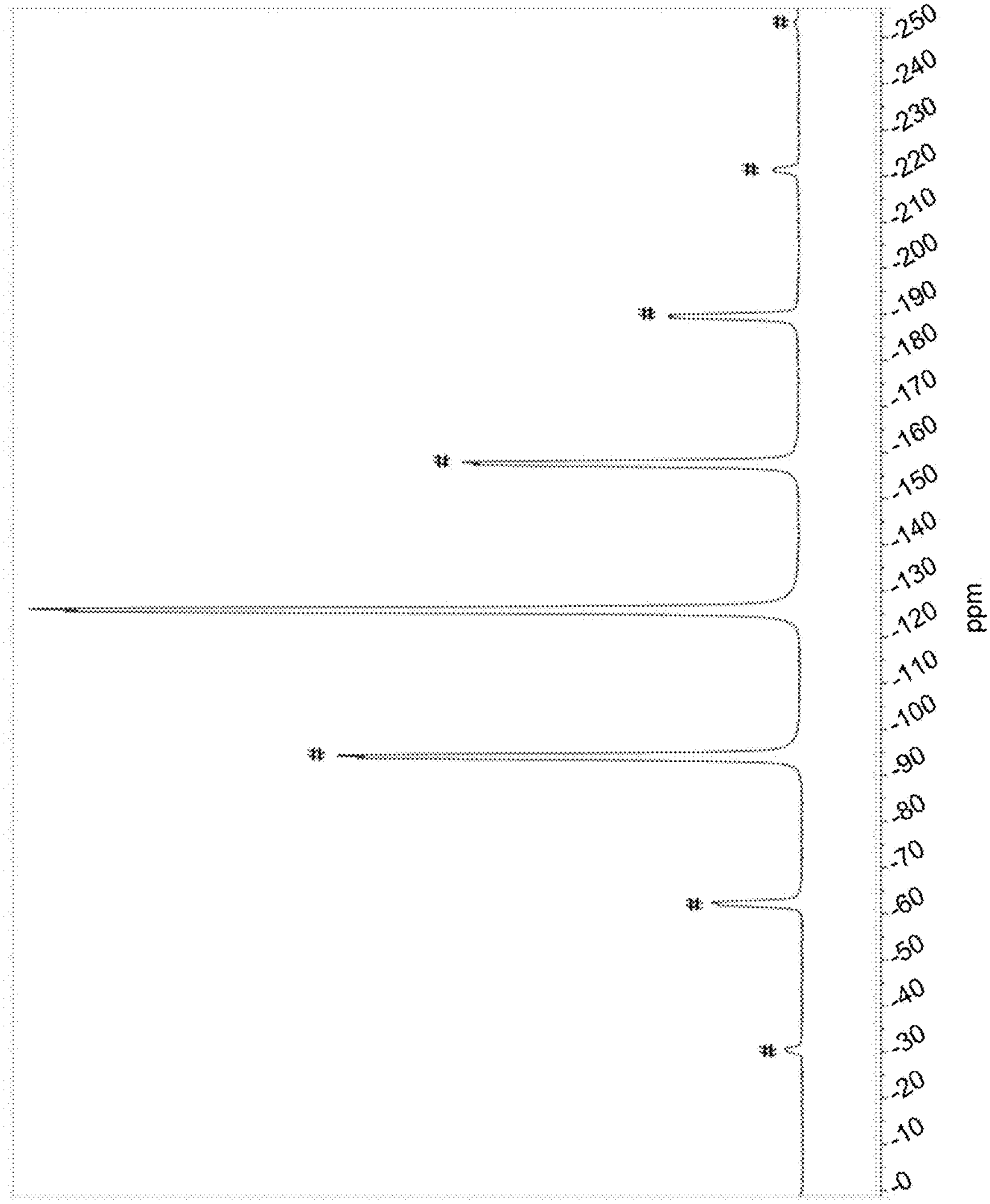
FIG. 4. Fluorine MAS spectrum of crystalline PF-07220060 monohydrate (Form 2) (# indicates spinning sidebands).

In another embodiment, the invention provides a crystalline form of PF-07220060 monohydrate (Form 2) having a $^{19}F$ solid state NMR spectrum (ppm) comprising: (a) one or two resonance (ppm) values selected from the group consisting of the values in Table 4 in ppm±0.2 ppm; or (b) resonance (ppm) values essentially the same as shown in FIG. 4.

In another aspect, the invention provides a crystalline form of PF-07220060 monohydrate (Form 2) having:

(a) a powder X-ray diffraction (PXRD) pattern comprising peaks at 2θ values of: 9.6, 11.8 and 14.7°2θ±0.2°2θ;

(b) a Raman spectrum comprising wavenumber ($cm^{-1}$) values of: 1484, 1555 and 1587 $cm^{-1}$±2 $cm^{-1}$;

(c) a $^{13}C$ solid state NMR spectrum comprising resonance (ppm) values of: 22.8 and 163.0 ppm±0.2 ppm; or (d) a $^{19}F$ solid state NMR spectrum comprising resonance (ppm) values of: −126.1 and −125.6 ppm±0.2 ppm;

or any combination of two or more of (a), (b), (c) and (d).

In another aspect, the invention provides a crystalline form of PF-07220060 monohydrate (Form 2) having:

(1) a powder X-ray diffraction (PXRD) pattern comprising peaks at 2θ values of:
  (a) 9.6, 11.8 and 14.7°2θ±0.2°2θ;
  (b) 9.6, 11.8, 12.4 and 14.7°2θ±0.2°2θ;
  (c) 9.6, 11.8, 14.7 and 21.0°2θ±0.2°2θ; or
  (d) 9.6, 11.8, 12.4, 14.7 and 21.0°2θ±0.2°2θ;

(2) a Raman spectrum comprising wavenumber ($cm^{-1}$) values of:
  (a) 1484, 1555 and 1587 $cm^{-1}$±2 $cm^{-1}$;
  (b) 1387, 1484, 1555 and 1587 $cm^{-1}$ 2 $cm^{-1}$;
  (c) 1395, 1484, 1555 and 1587 $cm^{-1}$ 2 $cm^{-1}$; or
  (d) 1387, 1395, 1484, 1555 and 1587 $cm^{-1}$±2 $cm^{-1}$;

(3) a $^{13}C$ solid state NMR spectrum comprising resonance (ppm) values of:
  (a) 22.8 and 163.0 ppm±0.2 ppm;
  (b) 22.8, 50.3 and 163.0 ppm±0.2 ppm;
  (c) 22.8, 109.8 and 163.0 ppm±0.2 ppm;
  (d) 22.8, 129.1 and 163.0 ppm±0.2 ppm;
  (e) 22.8, 50.3, 109.8 and 163.0 ppm±0.2 ppm;
  (f) 22.8, 50.3, 129.1 and 163.0 ppm±0.2 ppm;
  (g) 22.8, 109.8, 129.1 and 163.0 ppm±0.2 ppm; or
  (h) 22.8, 50.3, 109.8, 129.1 and 163.0 ppm±0.2 ppm;

or (4) a $^{19}F$ solid state NMR spectrum comprising a resonance (ppm) value of:
  (a) −126.1 ppm±0.2 ppm;
  (b) −125.6 ppm±0.2 ppm; or
  (c) −125.6 and −126.1 ppm±0.2 ppm;

or any combination of two or more of (1)(a)-(d), (2)(a)-(d), (3)(a)-(h) and (4)(a)-(c).

In another aspect, the invention provides a pharmaceutical composition comprising the crystalline form of PF-07220060 monohydrate (Form 2), according to the aspects or embodiments described herein, and a pharmaceutically acceptable carrier or excipient.

In another aspect, the invention provides a method of treating cancer in a subject in need thereof, comprising administering to the subject a therapeutically effective amount of the crystalline form of PF-07220060 monohydrate (Form 2), or a pharmaceutical composition comprising the crystalline form of PF-07220060 monohydrate (Form 2), according to the aspects or embodiments described herein.

In another aspect, the invention provides a method of treating cancer in a subject in need thereof, comprising administering to the subject an amount of the crystalline form of PF-07220060 monohydrate (Form 2), or a pharmaceutical composition comprising the crystalline form of PF-07220060 monohydrate (Form 2), according to the aspects or embodiments described herein, and an amount of an additional anticancer agent, wherein the amounts of PF-07220060 monohydrate (Form 2) and the additional anticancer agent together are effective in treating cancer.

In another aspect, the invention provides use of the crystalline form of PF-07220060 monohydrate (Form 2), or a pharmaceutical composition comprising the crystalline form of PF-07220060 monohydrate (Form 2), according to the aspects or embodiments described herein, for the treatment of cancer.

In yet another aspect, the invention provides use of the crystalline form of PF-07220060 monohydrate (Form 2), according to the aspects or embodiments described herein, in the manufacture of a medicament for the treatment of cancer.

In another aspect, the invention provides the crystalline form of PF-07220060 monohydrate (Form 2) or a pharmaceutical composition comprising the crystalline form of PF-07220060 monohydrate (Form 2), according to the aspects or embodiments described herein, for use in the treatment of cancer.

In each of the aspects and embodiments of crystalline PF-07220060 monohydrate (Form 2) described herein, the crystalline form may be a substantially pure crystalline form of PF-07220060 monohydrate (Form 2).

Each of the embodiments described herein for crystalline PF-07220060 monohydrate (Form 2) may be combined with other such embodiments, provided the embodiments are not inconsistent with each other.

In another aspect, the invention provides an amorphous form of PF-07220060 (Form 8). In some embodiments, the amorphous form of PF-07220060 (Form 8) is characterized by its powder X-ray diffraction (PXRD) pattern. In some embodiments, the amorphous form of PF-07220060 (Form 8) is characterized by differential scanning calorimetry (DSC) scan. In further embodiments, the amorphous form of PF-07220060 (Form 8) is characterized by a combination of PXRD and DSC. In other embodiments, the amorphous form of PF-07220060 (Form 8) is characterized by its Raman spectrum. In other embodiments, the amorphous form of PF-07220060 (Form 8) is characterized by its $^{13}C$ solid state NMR spectrum. In still other embodiments, the amorphous form of PF-07220060 (Form 8) is characterized by its $^{19}F$ solid state NMR spectrum. In further embodiments, the amorphous form of PF-07220060 (Form 8) is characterized by any combination of two or more of these methods. In some such embodiments, the amorphous form of PF-07220060 (Form 8) is characterized by $^{19}F$ solid state NMR and $^{13}C$ solid state NMR.

In one embodiment, the invention provides an amorphous form of PF-07220060 (Form 8). In another embodiment, the invention provides an amorphous form of PF-07220060 (Form 8) characterized by its powder X-ray diffraction (PXRD) pattern. In some such embodiments, the invention provides an amorphous form of PF-07220060 (Form 8) having a powder X-ray diffraction (PXRD) pattern (2θ) comprising: (a) a broad peak at diffraction angles (2θ) from about 4 to about 40°2θ±0.5°2θ; or (b) peaks at 20 values essentially the same as in FIG. 8.

In another embodiment, the invention provides an amorphous form of PF-07220060 (Form 8) characterized by DSC. In some such embodiments, the invention provides an amorphous form of PF-07220060 (Form 8) having: (a) a glass transition temperature (Tg) of about 102° C. as measured by DSC at a ramp rate of 2° C./min; or (b) a DSC thermogram essentially the same as in FIG. 9.

In another aspect, the invention provides an amorphous form of PF-07220060 (Form 8) characterized by a Raman spectrum.

In one embodiment, the invention provides an amorphous form of PF-07220060 (Form 8) having a Raman spectrum comprising wavenumber ($cm^{-1}$) values of: 1430 and 1453 $cm^{-1}$±2 $cm^{-1}$. In one embodiment, the invention provides an amorphous form of PF-07220060 (Form 8) having a Raman spectrum comprising wavenumber ($cm^{-1}$) values of: 1430 and 1574 $cm^{-1}$±2 $cm^{-1}$. In one embodiment, the invention provides an amorphous form of PF-07220060 (Form 8) having a Raman spectrum comprising wavenumber ($cm^{-1}$) values of: 1430, 1453 and 1574 $cm^{-1}$±2 $cm^{-1}$.

In one embodiment, the invention provides amorphous form of PF-07220060 (Form 8) having a Raman spectrum comprising: (a) one, two, three, four, five, or more than five wavenumber ($cm^{-1}$) values selected from the group consisting of the values in Table 7 in $cm^{-1}$±2 $cm^{-1}$; or (b) wavenumber ($cm^{-1}$) values essentially the same as in FIG. 10.

In another aspect, the invention provides an amorphous form of PF-07220060 (Form 8) characterized by a $^{13}C$ solid state NMR spectrum.

In one embodiment, the invention provides an amorphous form of PF-07220060 (Form 8) having a $^{13}C$ solid state NMR spectrum comprising resonance (ppm) values of: 20.9, 49.3 and 116.6 ppm±0.5 ppm. In one embodiment, the invention provides an amorphous form of PF-07220060 (Form 8) having a $^{13}C$ solid state NMR spectrum comprising resonance (ppm) values of: 20.9 and 49.3 ppm±0.5 ppm. In one embodiment, the invention provides an amorphous form of PF-07220060 (Form 8) having a $^{13}C$ solid state NMR spectrum comprising resonance (ppm) values of: 20.9 and 116.6 ppm±0.5 ppm. In one embodiment, the invention provides an amorphous form of PF-07220060 (Form 8) having a $^{13}C$ solid state NMR spectrum comprising resonance (ppm) values of: 49.3, and 116.6 ppm±0.5 ppm.

In another embodiment, the invention provides an amorphous form of PF-07220060 (Form 8) having a $^{13}C$ solid state NMR spectrum (ppm) comprising: (a) one, two, three, four, five, or more than five resonance (ppm) values selected from the group consisting of the values in Table 8 in ppm±0.5 ppm; or (b) resonance (ppm) values essentially the same as in FIG. 11.

Figure 12:
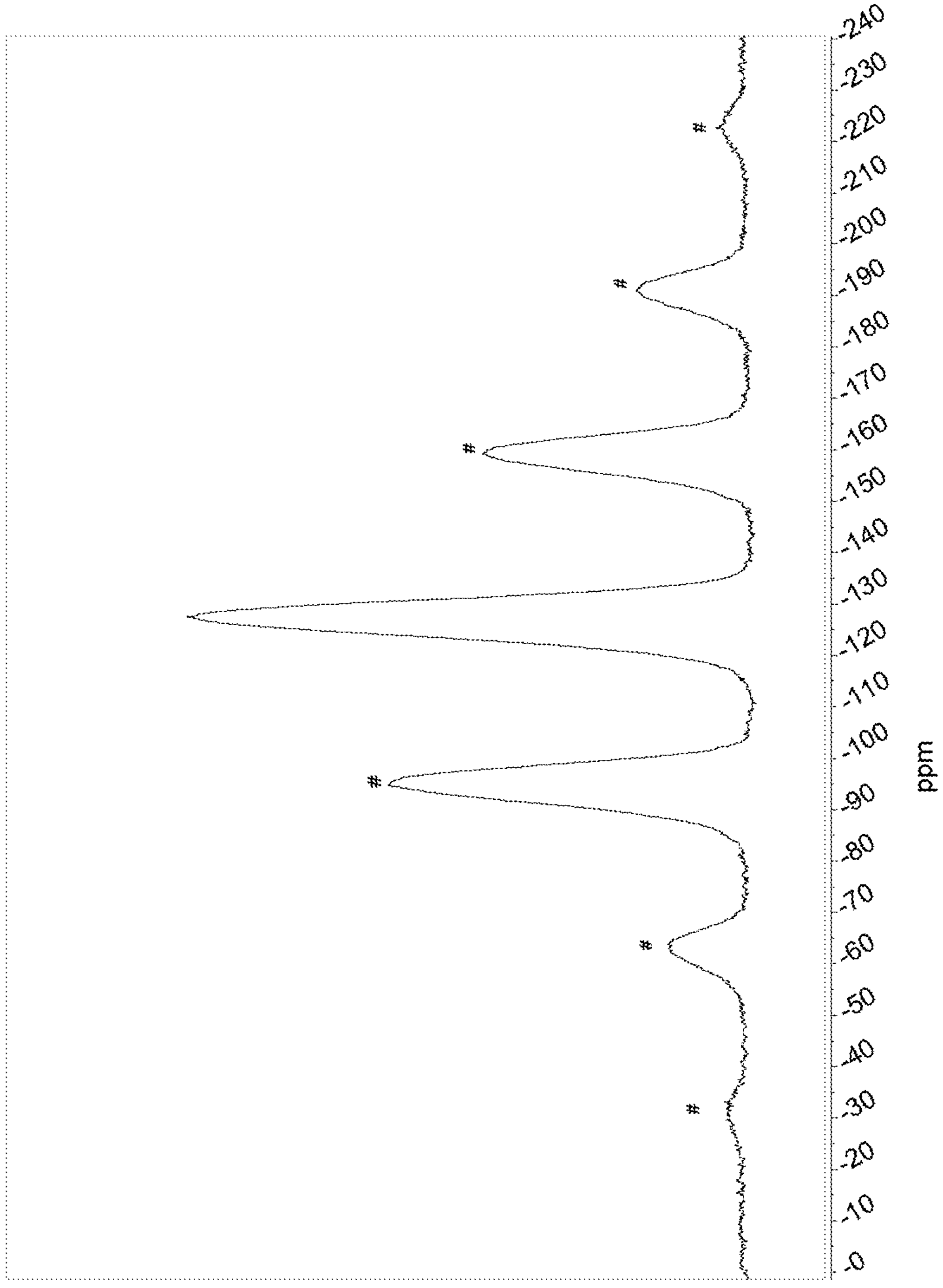
FIG. 12. Fluorine MAS spectrum of amorphous PF-07220060 (Form 8) (# indicates spinning sidebands).

In another aspect, the invention provides an amorphous form of PF-07220060 (Form 8) characterized by a $^{19}F$ solid state NMR spectrum. In one embodiment, the invention provides an amorphous form of PF-07220060 (Form 8)

having a $^{19}F$ solid state NMR spectrum comprising a resonance (ppm) value of: −127.5 ppm±0.5 ppm. In another embodiment, the invention provides an amorphous form of PF-07220060 (Form 8) having a $^{19}F$ solid state NMR spectrum (ppm) comprising: (a) the resonance (ppm) value in Table 9 in ppm±0.5 ppm; or (b) resonance (ppm) values essentially the same as shown in FIG. 12.

In one embodiment, the invention provides an amorphous form of PF-07220060 (Form 8) having a $^{19}F$ solid state NMR spectrum comprising a resonance (ppm) value of: −127.5 ppm±0.5 ppm; and a $^{13}C$ solid state NMR spectrum comprising resonance (ppm) values of: (a) 20.9, 49.3 and 116.6 ppm±0.5 ppm; (b) 20.9 and 49.3 ppm±0.5 ppm; (c) 20.9 and 116.6 ppm±0.5 ppm; or (d) 49.3 and 116.6 ppm±0.5 ppm.

In another embodiment, the invention provides an amorphous form of PF-07220060 (Form 8) having:

(1) a powder X-ray diffraction (PXRD) pattern (2θ) comprising:
  (a) a broad peak at diffraction angles (2θ) from about 4 to about 40°2θ±0.5°2θ; or
  (b) peaks at 2θ values essentially the same as in FIG. 8; or
(2) a DSC thermogram comprising:
  (a) a glass transition temperature (Tg) of about 102° C. as measured by DSC at a ramp rate of 2° C./min; or
  (b) a DSC thermogram essentially the same as in FIG. 9; or
(3) a $^{19}F$ solid state NMR spectrum comprising:
  (a) a resonance (ppm) value of: −127.5 ppm±0.5 ppm; or
  (b) resonance (ppm) values essentially the same as shown in FIG. 12; or
(4) a $^{13}C$ solid state NMR spectrum comprising resonance (ppm) values of:
  (a) 20.9, 49.3 and 116.6 ppm±0.5 ppm;
  (b) 20.9 and 49.3 ppm±0.5 ppm;
  (c) 20.9 and 116.6 ppm±0.5 ppm; or
  (d) 49.3 and 116.6 ppm±0.5 ppm;

or any combination of two or more of (1)(a)-(b), (2)(a)-(b), (3)(a)-(b) and (4)(a)-(d).

In another aspect, the invention provides a pharmaceutical composition comprising an amorphous form of PF-07220060 (Form 8), according to the aspects or embodiments described herein, and a pharmaceutically acceptable carrier or excipient.

In another aspect, the invention provides a method of treating cancer in a subject in need thereof, comprising administering to the subject a therapeutically effective amount of an amorphous form of PF-07220060 (Form 8), or a pharmaceutical composition comprising an amorphous form of PF-07220060 (Form 8), according to the aspects or embodiments described herein.

In another aspect, the invention provides a method of treating cancer in a subject in need thereof, comprising administering to the subject an amount of an amorphous form of PF-07220060 (Form 8), or a pharmaceutical composition comprising an amorphous form of PF-07220060 (Form 8), according to the aspects or embodiments described herein, and an amount of an additional anticancer agent, wherein the amounts of PF-07220060 and the additional anticancer agent together are effective in treating cancer.

In another aspect, the invention provides use of an amorphous form of PF-07220060 (Form 8), or a pharmaceutical composition comprising an amorphous form of PF-07220060 (Form 8), according to the aspects or embodiments described herein, for the treatment of cancer.

In yet another aspect, the invention provides use of an amorphous form of PF-07220060 (Form 8), or a pharmaceutical composition comprising an amorphous form of PF-07220060 (Form 8), according to the aspects or embodiments described herein, in the manufacture of a medicament for the treatment of cancer.

In another aspect, the invention provides an amorphous form of PF-07220060 (Form 8), or a pharmaceutical composition comprising an amorphous form of PF-07220060 (Form 8), according to the aspects or embodiments described herein, for use in the treatment of cancer.

In each of the aspects and embodiments of amorphous PF-07220060 (Form 8) described herein, the amorphous form may be a substantially pure amorphous form of PF-07220060 (Form 8).

Each of the embodiments described herein for amorphous PF-07220060 (Form 8) may be combined with other such embodiments, provided the embodiments are not inconsistent with each other.

In one aspect, the invention provides an anhydrous crystalline form of PF-07220060 (Form 6). In some embodiments the anhydrous crystalline form of PF-07220060 (Form 6) is characterized by its powder X-ray diffraction (PXRD) pattern. In other embodiments, the anhydrous crystalline form of PF-07220060 (Form 6) is characterized by its Raman spectrum. In other embodiments, the anhydrous crystalline form of PF-07220060 (Form 6) is characterized by its $^{13}C$ solid state NMR spectrum. In still other embodiments, the anhydrous crystalline form of PF-07220060 (Form 6) is characterized by its $^{19}F$ solid state NMR spectrum.

In further embodiments, anhydrous crystalline PF-07220060 (Form 6) is characterized by any combination of two or more of these methods. Exemplary combinations including two or more of the following are provided herein: powder X-ray diffraction (PXRD) pattern (2θ); Raman spectrum wavenumber values ($cm^{-1}$); $^{13}C$ solid state NMR spectrum (ppm); or $^{19}F$ solid state NMR spectrum (ppm). In some embodiments anhydrous crystalline PF-07220060 (Form 6) is characterized by PXRD and Raman. In other embodiments, anhydrous crystalline PF-07220060 (Form 6) is characterized by PXRD and $^{13}C$ solid state NMR. In other embodiments, anhydrous crystalline PF-07220060 (Form 6) is characterized by PXRD and $^{19}F$ solid state NMR. In other embodiments anhydrous crystalline PF-07220060 (Form 6) is characterized by $^{19}F$ solid state NMR and Raman. In other embodiments anhydrous crystalline PF-07220060 (Form 6) is characterized by $^{19}F$ solid state NMR and $^{13}C$ solid state NMR. In other embodiments anhydrous crystalline PF-07220060 (Form 6) is characterized by PXRD, $^{19}F$ solid state NMR and $^{13}C$ solid state NMR. In other embodiments anhydrous crystalline PF-07220060 (Form 6) is characterized by PXRD, Raman and $^{19}F$ solid state NMR.

In one aspect, the invention provides an anhydrous crystalline form of PF-07220060 (Form 6) characterized by a powder X-ray diffraction (PXRD) pattern.

In one embodiment, the invention provides an anhydrous crystalline form of PF-07220060 (Form 6) having a powder X-ray diffraction (PXRD) pattern comprising peaks at 2θ values of: 6.8 and 10.1°2θ±0.2°2θ.

In one embodiment, the invention provides an anhydrous crystalline form of PF-07220060 (Form 6) having a powder X-ray diffraction (PXRD) pattern comprising peaks at 2θ values of: 6.8, 10.1 and 12.2°2θ±0.2°2θ.

In one embodiment, the invention provides an anhydrous crystalline form of PF-07220060 (Form 6) having a powder X-ray diffraction (PXRD) pattern comprising peaks at 2θ values of: 6.8, 10.1 and 17.8°2θ±0.2°2θ.

In one embodiment, the invention provides an anhydrous crystalline form of PF-07220060 (Form 6) having a powder X-ray diffraction (PXRD) pattern comprising peaks at 2θ values of: 6.8, 10.1, 12.2 and 17.8°2θ±0.2°2θ.

In another embodiment, the invention provides an anhydrous crystalline form of PF-07220060 (Form 6) having a powder X-ray diffraction (PXRD) pattern comprising peaks at 2θ values of: 8.5, 10.1 and 13.8°2θ±0.2°2θ.

In another embodiment, the invention provides an anhydrous crystalline form of PF-07220060 (Form 6) having a powder X-ray diffraction (PXRD) pattern comprising peaks at 2θ values of: 6.8, 8.5 and 13.8°2θ±0.2°2θ.

In another embodiment, the invention provides an anhydrous crystalline form of PF-07220060 (Form 6) having a powder X-ray diffraction (PXRD) pattern comprising peaks at 2θ values of: 6.8, 8.5, 10.1 and 13.8°2θ±0.2°2θ.

In another embodiment, the invention provides an anhydrous crystalline form of PF-07220060 (Form 6) having a powder X-ray diffraction (PXRD) pattern comprising peaks at 2θ values of: 6.8, 8.5, 10.1, 12.2 and 13.8°2θ±0.2°2θ.

In one embodiment, the invention provides an anhydrous crystalline form of PF-07220060 (Form 6) having a powder X-ray diffraction (PXRD) pattern comprising peaks at 2θ values of: 6.8 and 10.1°2θ±0.2°2θ; and one, two, three or four peaks selected from the group consisting of: 8.5, 12.2, 13.8 and 17.8°2θ±0.2°2θ.

In another embodiment, the invention provides an anhydrous crystalline form of PF-07220060 (Form 6) having a PXRD pattern comprising three or more peaks at 20 values selected from the group consisting of: 6.8, 8.5, 10.1, 12.2, 13.8 and 17.8°2θ±0.2°2θ.

In another embodiment, the invention provides an anhydrous crystalline form of PF-07220060 (Form 6) having a PXRD pattern comprising: (a) one, two, three, four, five, or more than five peaks selected from the group consisting of the peaks in Table 10 in ° 2θ±0.2°2θ; or (b) peaks at 2θ values essentially the same as in FIG. 13.

In another aspect, the invention provides an anhydrous crystalline form of PF-07220060 (Form 6) characterized by a Raman spectrum.

In one embodiment, the invention provides an anhydrous crystalline form of PF-07220060 (Form 6) having a Raman spectrum comprising a wavenumber ($cm^{-1}$) value of: 1436 $cm^{-1}$±2 $cm^{-1}$.

In one embodiment, the invention provides an anhydrous crystalline form of PF-07220060 (Form 6) having a Raman spectrum comprising wavenumber ($cm^{-1}$) values of: 1436 and 1566 $cm^{-1}$±2 $cm^{-1}$.

In one embodiment, the invention provides an anhydrous crystalline form of PF-07220060 (Form 6) having a Raman spectrum comprising wavenumber ($cm^{-1}$) values of: 1436 and 1465 $cm^{-1}$±2 $cm^{-1}$.

In one embodiment, the invention provides an anhydrous crystalline form of PF-07220060 (Form 6) having a Raman spectrum comprising wavenumber ($cm^{-1}$) values of: 1436, 1465 and 1566 $cm^{-1}$±2 $cm^{-1}$.

In one embodiment, the invention provides an anhydrous crystalline form of PF-07220060 (Form 6) having a Raman spectrum comprising: (a) one, two, three, four, five, or more than five wavenumber ($cm^{-1}$) values selected from the group consisting of the values in Table 11 in $cm^{-1}$±2 $cm^{-1}$; or (b) wavenumber ($cm^{-1}$) values essentially the same as in FIG. 14.

In another aspect, the invention provides an anhydrous crystalline form of PF-07220060 (Form 6) characterized by a $^{13}C$ solid state NMR spectrum.

In one embodiment, the invention provides an anhydrous crystalline form of PF-07220060 (Form 6) having a $^{13}C$ solid state NMR spectrum comprising resonance (ppm) values of: 54.7 and 112.6 ppm±0.2 ppm.

In one embodiment, the invention provides an anhydrous crystalline form of PF-07220060 (Form 6) having a $^{13}C$ solid state NMR spectrum comprising resonance (ppm) values of: 54.7 and 132.8 ppm±0.2 ppm.

In one embodiment, the invention provides an anhydrous crystalline form of PF-07220060 (Form 6) having a $^{13}C$ solid state NMR spectrum comprising resonance (ppm) values of: 112.6 and 132.8 ppm±0.2 ppm.

In one embodiment, the invention provides an anhydrous crystalline form of PF-07220060 (Form 6) having a $^{13}C$ solid state NMR spectrum comprising resonance (ppm) values of: 54.7, 112.6 and 132.8 ppm±0.2 ppm.

In another embodiment, the invention provides an anhydrous crystalline form of PF-07220060 (Form 6) having a $^{13}C$ solid state NMR spectrum comprising resonance (ppm) values of: 49.2, 54.7 and 112.6 ppm±0.2 ppm.

In one embodiment, the invention provides an anhydrous crystalline form of PF-07220060 (Form 6) having a $^{13}C$ solid state NMR spectrum comprising resonance (ppm) values of: 49.2, 54.7 and 132.8 ppm±0.2 ppm.

In another embodiment, the invention provides an anhydrous crystalline form of PF-07220060 (Form 6) having a $^{13}C$ solid state NMR spectrum comprising resonance (ppm) values of: 49.2, 54.7, 112.6 and 132.8 ppm±0.2 ppm.

In one embodiment, the invention provides an anhydrous crystalline form of PF-07220060 (Form 6) having a $^{13}C$ solid state NMR spectrum comprising resonance (ppm) value of: 54.7 and 112.6 ppm±0.2 ppm; and one or two resonance (ppm) values selected from the group consisting of: 49.2 and 132.8 ppm±0.2 ppm.

In one embodiment, the invention provides an anhydrous crystalline form of PF-07220060 (Form 6) having a $^{13}C$ solid state NMR spectrum comprising resonance (ppm) value of: 54.7 ppm±0.2 ppm; and one, two or three resonance (ppm) values selected from the group consisting of: 49.2, 112.6 and 132.8 ppm±0.2 ppm.

In another embodiment, the invention provides an anhydrous crystalline form of PF-07220060 (Form 6) having a $^{13}C$ solid state NMR spectrum (ppm) comprising: (a) one, two, three, four, five, or more than five resonance (ppm) values selected from the group consisting of the values in Table 12 in ppm±0.2 ppm; or (b) resonance (ppm) values essentially the same as in FIG. 15.

In another aspect, the invention provides an anhydrous crystalline form of PF-07220060 (Form 6) characterized by a $^{19}F$ solid state NMR spectrum.

In one embodiment, the invention provides an anhydrous crystalline form of PF-07220060 (Form 6) having a $^{19}F$ solid state NMR spectrum comprising a resonance (ppm) value of: −132.4 ppm±0.2 ppm.

In another embodiment, the invention provides an anhydrous crystalline form of PF-07220060 (Form 6) having a $^{19}F$ solid state NMR spectrum comprising a resonance (ppm) value of: −131.1 ppm±0.2 ppm.

In another embodiment, the invention provides an anhydrous crystalline form of PF-07220060 (Form 6) having a $^{19}F$ solid state NMR spectrum comprising resonance (ppm) values of: −131.1 and −132.4 ppm±0.2 ppm.

Figure 16:
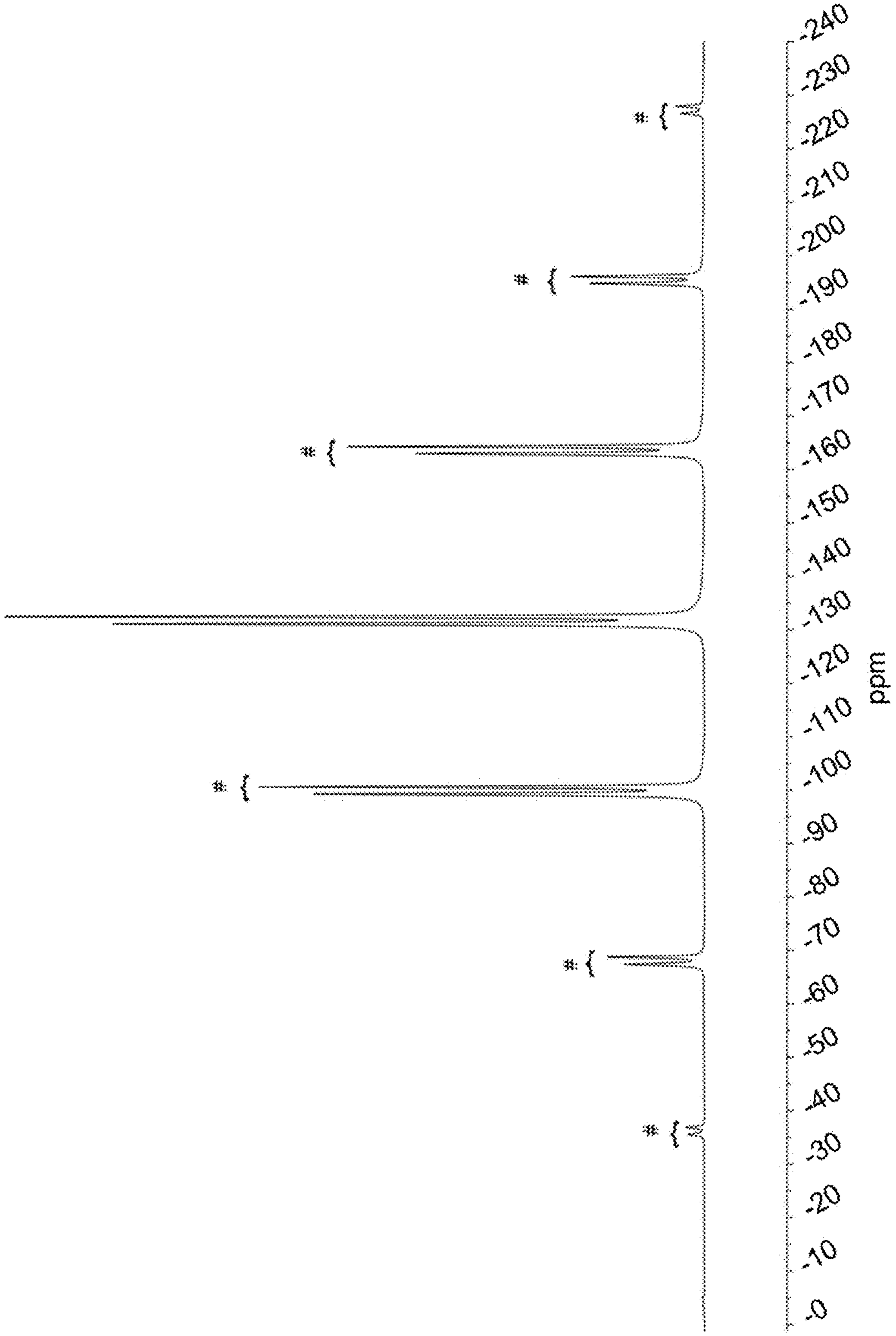
FIG. 16. Fluorine MAS spectrum of anhydrous crystalline PF-07220060 (Form 6) (# indicates spinning sidebands).

In another embodiment, the invention provides an anhydrous crystalline form of PF-07220060 (Form 6) having a $^{19}F$ solid state NMR spectrum (ppm) comprising: (a) one or two resonance (ppm) values selected from the group consisting of the values in Table 13 in ppm±0.2 ppm; or (b) resonance (ppm) values essentially the same as shown in FIG. 16.

In another aspect, the invention provides an anhydrous crystalline form of PF-07220060 (Form 6) having:

(1) a powder X-ray diffraction (PXRD) pattern comprising peaks at 2θ values of:
  (a) 6.8 and 10.1°2θ±0.2°2θ;
  (b) 6.8, 10.1 and 12.2°2θ±0.2°2θ;
  (c) 6.8, 10.1 and 17.8°2θ±0.2°2θ;
  (d) 6.8, 10.1, 12.2 and 17.8°2θ±0.2°2θ;
  (e) 8.5, 10.1 and 13.8°2θ±0.2°2θ;
  (f) 6.8, 8.5 and 13.8°2θ±0.2°2θ;
  (g) 6.8, 8.5, 10.1 and 13.8°2θ±0.2°2θ; or
  (h) 6.8, 8.5, 10.1, 12.2 and 13.8°2θ0.2°2θ;
(2) a Raman spectrum comprising wavenumber ($cm^{-1}$) values of:
  (a) 1436 and 1566 $cm^{-1}$±2 $cm^{-1}$;
  (b) 1436 and 1465 $cm^{-1}$±2 $cm^{-1}$; or
  (c) 1436, 1465 and 1566 $cm^{-1}$±2 $cm^{-1}$;
(3) a $^{13}C$ solid state NMR spectrum comprising resonance (ppm) values of:
  (a) 54.7 and 112.6 ppm±0.2 ppm;
  (b) 54.7 and 132.8 ppm±0.2 ppm;
  (c) 112.6 and 132.8 ppm±0.2 ppm;
  (d) 54.7, 112.6 and 132.8 ppm±0.2 ppm;
  (e) 49.2, 54.7 and 112.6 ppm±0.2 ppm;
  (f) 49.2, 54.7 and 132.8 ppm±0.2 ppm; or
  (g) 49.2, 54.7, 112.6 and 132.8 ppm±0.2 ppm;
or
(4) a $^{19}F$ solid state NMR spectrum comprising a resonance (ppm) value of:
  (a) −132.4 ppm±0.2 ppm;
  (b) −131.1 ppm±0.2 ppm; or
  (c) −131.1 and −132.4 ppm±0.2 ppm;
or any combination of two or more of (1)(a)-(h), (2)(a)-(c), (3)(a)-(g) and (4)(a)-(c).

In another aspect, the invention provides a pharmaceutical composition comprising an anhydrous crystalline form of PF-07220060 (Form 6), according to the aspects or embodiments described herein, and a pharmaceutically acceptable carrier or excipient.

In another aspect, the invention provides a method of treating cancer in a subject in need thereof, comprising administering to the subject a therapeutically effective amount of the anhydrous crystalline form of PF-07220060 (Form 6), or a pharmaceutical composition comprising an anhydrous crystalline form of PF-07220060 (Form 6), according to the aspects or embodiments described herein.

In another aspect, the invention provides a method of treating cancer in a subject in need thereof, comprising administering to the subject an amount of an anhydrous crystalline form of PF-07220060 (Form 6), or a pharmaceutical composition comprising an anhydrous crystalline form of PF-07220060 (Form 6), according to the aspects or embodiments described herein, and an amount of an additional anticancer agent, wherein the amounts of anhydrous crystalline PF-07220060 (Form 6) and the additional anticancer agent together are effective in treating cancer.

In another aspect, the invention provides use of an anhydrous crystalline form of PF-07220060 (Form 6), or a pharmaceutical composition comprising an anhydrous crystalline form of PF-07220060 (Form 6), according to the aspects or embodiments described herein, for the treatment of cancer.

In yet another aspect, the invention provides use of an anhydrous crystalline form of PF-07220060 (Form 6), according to the aspects or embodiments described herein, in the manufacture of a medicament for the treatment of cancer.

In another aspect, the invention provides an anhydrous crystalline form of PF-07220060 (Form 6) or a pharmaceutical composition comprising an anhydrous crystalline form of PF-07220060 (Form 6), according to the aspects or embodiments described herein, for use in the treatment of cancer.

In each of the aspects and embodiments of anhydrous crystalline PF-07220060 (Form 6) described herein, the crystalline form may be a substantially pure anhydrous crystalline form of PF-07220060 (Form 6).

Each of the embodiments described herein for anhydrous crystalline PF-07220060 (Form 6) may be combined with other such embodiments, provided the embodiments are not inconsistent with each other.

In one aspect, the invention provides an anhydrous crystalline form of PF-07220060 (Form 11). In some embodiments the anhydrous crystalline form of PF-07220060 (Form 11) is characterized by its powder X-ray diffraction (PXRD) pattern. In an embodiment, the invention provides an anhydrous crystalline form of PF-07220060 (Form 11) having a PXRD pattern comprising peaks at 2θ values essentially the same as in FIG. 17.

In another aspect, the invention provides a pharmaceutical composition comprising an anhydrous crystalline form of PF-07220060 (Form 11), according to the aspects or embodiments described herein, and a pharmaceutically acceptable carrier or excipient.

In another aspect, the invention provides a method of treating cancer in a subject in need thereof, comprising administering to the subject a therapeutically effective amount of the anhydrous crystalline form of PF-07220060 (Form 11), or a pharmaceutical composition comprising an anhydrous crystalline form of PF-07220060 (Form 11), according to the aspects or embodiments described herein.

In another aspect, the invention provides a method of treating cancer in a subject in need thereof, comprising administering to the subject an amount of an anhydrous crystalline form of PF-07220060 (Form 11), or a pharmaceutical composition comprising an anhydrous crystalline form of PF-07220060 (Form 11), according to the aspects or embodiments described herein, and an amount of an additional anticancer agent, wherein the amounts of anhydrous crystalline PF-07220060 (Form 11) and the additional anticancer agent together are effective in treating cancer.

In another aspect, the invention provides use of an anhydrous crystalline form of PF-07220060 (Form 11), or a pharmaceutical composition comprising an anhydrous crystalline form of PF-07220060 (Form 11), according to the aspects or embodiments described herein, for the treatment of cancer.

In yet another aspect, the invention provides use of an anhydrous crystalline form of PF-07220060 (Form 11), according to the aspects or embodiments described herein, in the manufacture of a medicament for the treatment of cancer.

In another aspect, the invention provides an anhydrous crystalline form of PF-07220060 (Form 11) or a pharmaceutical composition comprising an anhydrous crystalline form of PF-07220060 (Form 11), according to the aspects or embodiments described herein, for use in the treatment of cancer.

In each of the aspects and embodiments of anhydrous crystalline PF-07220060 (Form 11) described herein, the crystalline form may be a substantially pure anhydrous crystalline form of PF-07220060 (Form 11).

Each of the embodiments described herein for anhydrous crystalline PF-07220060 (Form 11) may be combined with other such embodiments, provided the embodiments are not inconsistent with each other.

In some embodiments of each of the methods and uses described herein, the cancer is selected from the group consisting of breast cancer, prostate cancer, lung cancer (including non-small cell lung cancer, NSCLC, and small cell lung cancer, SCLC), liver cancer (including hepatocellular carcinoma, HCC), kidney cancer (including renal cell carcinoma, RCC), bladder cancer (including urothelial carcinomas, such as upper urinary tract urothelial carcinoma, UUTUC), ovarian cancer (including epithelial ovarian cancer, EOC), peritoneal cancer (including primary peritoneal cancer, PPC), fallopian tube cancer, cervical cancer, uterine cancer (including endometrial cancer), pancreatic cancer, stomach cancer, colorectal cancer, esophageal cancer, head and neck cancer (including squamous cell carcinoma of the head and neck (SCCHN), thyroid cancer, and salivary gland cancer), testicular cancer, adrenal cancer, skin cancer (including basal cell carcinoma and melanoma), brain cancer (including astrocytoma, meningioma, and glioblastoma), sarcoma (including osteosarcoma and liposarcoma), and lymphoma (including mantle cell lymphoma, MCL).

In some embodiments of the methods and uses described herein, the cancer is advanced or metastatic cancer. In some embodiments of the methods and uses described herein, the cancer is early stage or non-metastatic cancer.

In some embodiments of the methods and uses described herein, the cancer is characterized by amplification or overexpression of CDK4, CDK6 and/or cyclin D1 (CCND1). In some embodiments, the cancer is RB-positive or RB-proficient.

In some embodiments of each of the methods and uses described herein, the cancer is resistant to a therapeutic agent or class of agents, such as a standard of care agent or class for the particular cancer. In some embodiments of each of the methods, and uses described herein, the cancer is characterized by innate or acquired resistance to a therapeutic agent or class of agents. In some such embodiments, the cancer is resistant to treatment with antiandrogens, taxanes, platinum agents, aromatase inhibitors, selective estrogen receptor degraders (SERDs), selective estrogen receptor modulators (SERMs), or CDK4/6 inhibitors.

In some embodiments of each of the methods and uses described herein, the cancer is breast cancer. In some such embodiments, the breast cancer is androgen-dependent breast cancer. In some embodiments, the breast cancer is AR+ breast cancer.

In some embodiments of the methods and uses described herein, the breast cancer is advanced or metastatic breast cancer. In some embodiments of the methods and uses described herein, the breast cancer is early stage or non-metastatic breast cancer.

In some embodiments of the methods and uses described herein, the breast cancer is characterized by amplification or overexpression of CDK4, CDK6 and/or cyclin D1 (CCND1). In some embodiments, the breast cancer is characterized as RB-positive, RB-proficient, or RB wild type.

In some embodiments of the methods and uses described herein, the breast cancer is BRCA1- or BRCA2-mutated breast cancer.

In some embodiments of the methods and uses described herein, the breast cancer is PIK3CA-mutated cancer breast cancer.

In some embodiments of the methods and uses described herein, the breast cancer is refractory or resistant to treatment with, or has progressed on, one or more standard of care agents. In some such embodiments, the breast cancer is refractory or resistant to treatment with, or has progressed on, an antiestrogen, such as an aromatase inhibitor, SERD, or a SERM. In some such embodiments, the breast cancer is refractory or resistant to treatment with, or has progressed on, a CDK4/6 inhibitor, such as palbociclib or a pharmaceutically acceptable salt thereof. In other embodiments, the breast cancer is refractory or resistant to treatment with, or has progressed on, treatment with antineoplastic chemotherapeutic agents such as taxanes, platinum agents, anthracyclines or anti-metabolites.

In some embodiments of each of the methods and uses described herein, the breast cancer is hormone receptor (HR)-positive (HR+) breast cancer, i.e., the breast cancer is estrogen receptor (ER)-positive (ER+) and/or progesterone receptor (PR)-positive (PR+).

In some embodiments, the breast cancer is hormone receptor (HR)-negative (HR−), i.e., the breast cancer is estrogen receptor (ER)-negative (ER−) and progesterone receptor (PR)-negative (PR−).

In some embodiments, the breast cancer is human epidermal growth factor receptor 2 (HER2)-positive (HER2+).

In some embodiments, the breast cancer is human epidermal growth factor receptor 2 (HER2)-negative (HER2−). In some such embodiments, the breast cancer is is estrogen receptor alpha (ERα)-negative.

In some embodiments, the breast cancer is triple negative breast cancer (TNBC), i.e., the breast cancer is ER−, PR− and HER2−.

In some embodiments, the breast cancer is selected from the group consisting of HR+/HER2− breast cancer, HR+/HER2+ breast cancer, HR−/HER2+ breast cancer, and triple negative breast cancer (TNBC). In some such embodiments, the breast cancer is androgen-dependent or AR+ breast cancer. In some such embodiments, the breast cancer is BRCA1− or BRCA2-mutated breast cancer.

In some embodiments, the breast cancer is HR+/HER2− breast cancer. In some such embodiments, the HR+/HER2− breast cancer is advanced or metastatic HR+/HER2− breast cancer. In some embodiments, the HR+/HER2− breast cancer is early or non-metastatic HR+/HER2− breast cancer.

In some embodiments, the HR+/HER2− breast cancer is characterized by amplification or overexpression of CDK4, CDK6 and/or cyclin D1 (CCND1). In some embodiments, the HR+/HER2− breast cancer is characterized as RB-positive, RB-proficient, or RB wild type.

In some embodiments, the HR+/HER2− breast cancer is BRCA1− or BRCA2− mutated breast cancer.

In some embodiments, the HR+/HER2− breast cancer is PIK3CA-mutated cancer breast cancer In some such embodiments, the HR+/HER2− breast cancer is refractory or resistant to treatment with, or has progressed on, a standard of care agent, e.g., an antiestrogen such as an aromatase inhibitor, a SERD, or a SERM. In some such embodiments, the HR+/HER2− breast cancer is refractory or resistant to treatment with, or has progressed on, a CDK4/6 inhibitor, such as palbociclib or a pharmaceutically acceptable salt thereof.

In some such embodiments, the HR+/HER2− breast cancer is refractory or resistant to treatment an antiestrogen such as an aromatase inhibitor, a SERD, or a SERM. In some such embodiments, the HR+/HER2− breast cancer is refractory or resistant to treatment with a CDK4/6 inhibitor, such as palbociclib or a pharmaceutically acceptable salt thereof. In some such embodiments, the HR+/HER2− breast cancer is refractory or resistant to treatment with a CDK4/6 inhibitor, such as palbociclib or a pharmaceutically acceptable salt thereof, in further combination with an antiestrogen, e.g., letrozole or fulvestrant.

In some such embodiments, the HR+/HER2− breast cancer is resistant to treatment an antiestrogen such as an aromatase inhibitor, a SERD, or a SERM. In some such embodiments, the HR+/HER2− breast cancer is resistant to treatment with a CDK4/6 inhibitor, such as palbociclib or a pharmaceutically acceptable salt thereof. In some such embodiments, the HR+/HER2− breast cancer is resistant to treatment with a CDK4/6 inhibitor, such as palbociclib or a pharmaceutically acceptable salt thereof, in further combination with an antiestrogen, e.g., letrozole or fulvestrant.

In some embodiments, the breast cancer is HR+/HER2+ breast cancer. In some embodiments, the breast cancer is HR−/HER2+ breast cancer.

In some embodiments wherein the breast cancer is HR+, the methods and uses described herein further comprise an additional anti-cancer agent. In some such embodiments, the additional anti-cancer agent is an antiestrogen, such as an aromatase inhibitor, a SERD, or a SERM. In some such embodiments, the antiestrogen is letrozole or fulvestrant. In some such embodiments, the additional anti-cancer agent is a CDK4/6 inhibitor, such as palbociclib or a pharmaceutically acceptable salt thereof. In some such embodiments, the additional anti-cancer agent is a CDK4/6 inhibitor, such as palbociclib or a pharmaceutically acceptable salt thereof, in further combination with an antiestrogen, e.g., letrozole or fulvestrant. In some such embodiments, the additional anti-cancer agent is a PI3K inhibitor, e.g., alpelisib.

In some embodiments wherein the breast cancer is HER2+, the methods and uses described herein further comprise an additional anti-cancer agent. In some such embodiments, the additional anti-cancer agent is a HER2-targeted agent, e.g., trastuzumab emtansine, fam-trastuzumab deruxtecan, pertuzumab, lapatinib, neratinib or tucatinib, or an agent targeting the PI3K/AKT/mTOR molecular pathway, e.g., ipatasertib.

In some embodiments, the breast cancer is triple negative breast cancer (TNBC). In some embodiments, the TNBC is androgen-dependent or AR+ TNBC. In some such embodiments, the TNBC is RN+ or RB-proficient. In some such embodiments, the TNBC is AR+, RB+ or AR+, RB-proficient TNBC.

In some such embodiments, the TNBC is locally recurrent/advanced or metastatic TNBC. In some such embodiments, the TNBC is advanced or metastatic TNBC. In some such embodiments, the TNBC is early or non-metastatic TNBC.

In some embodiments, the TNBC is characterized by amplification or overexpression of CDK4, CDK6 and/or cyclin D1 (CCND1).

In some embodiments, the TNBC is BRCA1- or BRCA2-mutated TNBC.

In some embodiments, the TNBC is refractory or resistant to treatment with, or has progressed on, a standard of care agent, e.g., an antineoplastic chemotherapeutic agent such as a taxane, platinum agent, anthracycline or anti-metabolite.

In some embodiments of each of the methods and uses described herein, the cancer is prostate cancer. In some such embodiments, the prostate cancer is androgen-dependent. In some such embodiments, the prostate cancer is AR+ prostate cancer.

In some embodiments of the methods and uses described herein, the prostate cancer is advanced or metastatic prostate cancer. In some embodiments of the methods and uses described herein, the prostate cancer is early stage or non-metastatic prostate cancer. In some embodiments of the methods and uses described herein, the prostate cancer is BRCA1- or BRCA2-mutated prostate cancer.

In some embodiments, the prostate cancer is castration resistant prostate cancer. In other embodiments, the prostate cancer is castration sensitive prostate cancer. In some embodiments of each of the methods and uses described herein, the prostate cancer is metastatic prostate cancer (mPC). In some such embodiments, the mPC is metastatic castration resistant prostate cancer (mCRPC). In other such embodiments, the mPC is metastatic castration-sensitive prostate cancer (mCSPC). In some embodiments of each of the methods and uses described herein, the prostate cancer is non-metastatic prostate cancer (nmPC). In some such embodiments, the nmPC is non-metastatic castration resistant prostate cancer (nmCRPC). In some such embodiments, the nmPC is non-metastatic castration sensitive prostate cancer (nmCSPC).

In some embodiments of the methods and uses described herein, the prostate cancer is refractory or resistant to treatment with, or has progressed on, one or more standard of care agents. In some such embodiments, the prostate cancer is refractory or resistant to treatment with, or has progressed on, antiandrogen therapy. In other embodiments, the prostate cancer is refractory or resistant to treatment with, or has progressed on, antineoplastic chemotherapeutic agents such as taxanes, platinum agents, anthracyclines or anti-metabolites.

In some such embodiments, the prostate cancer is refractory or resistant to treatment with an antiandrogen.

In some embodiments of each of the methods and uses described herein, the cancer is lung cancer. In some embodiments, the lung cancer is non-small_cell lung cancer (NSCLC). In some embodiments, the lung cancer is small cell lung cancer (SCLC). In some such embodiments, the lung cancer is advanced or metastatic lung cancer.

In some embodiments of each of the methods and uses described herein, the cancer is liver cancer. In some such embodiments the liver cancer is hepatocellular carcinoma (HCC). In some such embodiments, the liver cancer is advanced or metastatic liver cancer.

In some embodiments of each of the methods and uses described herein, the cancer is kidney cancer. In some such embodiments the kidney cancer is renal cell carcinoma (RCC). In some such embodiments, the kidney cancer is advanced or metastatic kidney cancer.

In some embodiments of each of the methods and uses described herein, the cancer is bladder cancer. In some such embodiments the bladder cancer is a urothelial carcinoma, including an upper urinary tract urothelial carcinoma (UUTUC). In some such embodiments, the bladder cancer is advanced or metastatic bladder cancer.

In some embodiments of each of the methods and uses described herein, the cancer is ovarian cancer, including epithelial ovarian cancer (EOC). In some such embodiments, the ovarian cancer is advanced or metastatic ovarian cancer.

In some embodiments of each of the methods and uses described herein, the cancer is peritoneal cancer, including primary peritoneal cancer (PPC). In some such embodiments, the peritoneal cancer is advanced or metastatic peritoneal cancer.

In some embodiments of each of the methods and uses described herein, the cancer is fallopian tube cancer. In some such embodiments, the fallopian tube cancer is advanced or metastatic fallopian tube cancer.

In some embodiments of each of the methods and uses described herein, the cancer is cervical cancer. In some such embodiments, the cervical cancer is advanced or metastatic cervical cancer.

In some embodiments of each of the methods and uses described herein, the cancer is uterine cancer, including endometrial cancer. In some such embodiments, the uterine cancer is advanced or metastatic uterine cancer.

In some embodiments of each of the methods and uses described herein, the cancer is pancreatic cancer. In some such embodiments, the pancreatic cancer is advanced or metastatic pancreatic cancer. In some such embodiments, the pancreatic cancer is resistant to antineoplastic chemotherapeutic agents such as taxanes, platinum agent, anthracyclines or anti-metabolites. In some such embodiments, the pancreatic cancer is resistant to gemcitabine or nab-paclitaxel.

In some embodiments of each of the methods and uses described herein, the cancer is stomach cancer. In some such embodiments, the stomach cancer is advanced or metastatic stomach cancer.

In some embodiments of each of the methods and uses described herein, the cancer is colorectal cancer. In some such embodiments, the colorectal cancer is advanced or metastatic colorectal cancer.

In some embodiments of each of the methods and uses described herein, the cancer is esophageal cancer. In some such embodiments, the esophageal cancer is advanced or metastatic esophageal cancer.

In some embodiments of each of the methods and uses described herein, the cancer is head and neck cancer. In some such embodiments, the head and neck cancer is advanced or metastatic head and neck cancer. In some such embodiments, the head and neck cancer is squamous cell carcinoma of the head and neck (SCCHN), thyroid cancer, or salivary gland cancer. In some such embodiments the head and neck cancer is salivary gland cancer.

In some embodiments of each of the methods and uses described herein, the cancer is testicular cancer. In some such embodiments, the testicular cancer is advanced or metastatic testicular cancer.

In some embodiments of each of the methods and uses described herein, the cancer is adrenal cancer. In some such embodiments, the adrenal cancer is advanced or metastatic adrenal cancer.

In some embodiments of each of the methods and uses described herein, the cancer is skin cancer. In some such embodiments, the skin cancer is basal cell carcinoma or melanoma. In some such embodiments, the skin cancer is advanced or metastatic skin cancer.

In some embodiments of each of the methods and uses described herein, the cancer is brain cancer. In some such embodiments, the brain cancer is astrocytoma, meningioma, or glioblastoma. In some such embodiments, the brain cancer is advanced or metastatic brain cancer.

In some embodiments of each of the methods and uses described herein, the cancer is sarcoma. In some such embodiments, the sarcoma is osteosarcoma or liposarcoma In some embodiments of each of the methods and uses described herein, the cancer is lymphoma. In some such embodiments, the lymphoma is mantle cell lymphoma (MCL).

In some embodiments, the compound of the invention is administered as first line therapy. In other embodiments, the compound of the invention is administered as second (or later) line therapy.

In some embodiments, the compound of the invention is administered as second (or later) line therapy following treatment with an endocrine therapeutic agent and/or a CDK4/CDK6 inhibitor. In some embodiments, the compound of the invention is administered as second (or later) line therapy following treatment with an endocrine therapeutic agent, e.g., an aromatase inhibitor, a SERM or a SERD. In some embodiments, the compound of the invention is administered as second (or later) line therapy following treatment with a CDK4/6 inhibitor. In some embodiments, the compound of the invention is administered as second (or later) line therapy following treatment with one or more chemotherapy regimens, e.g., including taxanes or platinum agents. In some embodiments, the compound of the invention is administered as second (or later) line therapy following treatment with anti-HER2 targeted agents, e.g., trastuzumab.

As used herein, an “effective dosage”, “effective amount” or “therapeutically effective amount” of a compound or pharmaceutical composition is the amount that, when used as indicated (which may be alone if used as a single agent or together with other agents if used in combination) is sufficient to affect one or more beneficial or desired outcomes, including preventing, ameliorating or treating the biochemical, histological or behavioral symptoms of the disease, its complications, and intermediate pathological phenotypes presenting during development of the disease. For prophylactic use, beneficial or desired outcomes may include: eliminating or reducing the risk, lessening the severity, or delaying the onset of the disease. For therapeutic use, beneficial or desired outcomes may include: reducing the incidence or ameliorating one or more symptoms of the disease, reducing the dose of another medication used to treat the disease, enhancing the efficacy or safety of another medication used to treat the disease, or delaying the time to disease progression.

In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

An effective dosage can be administered in one or more administrations. For the purposes of this invention, an effective dosage of a drug, compound, or pharmaceutical composition is an amount sufficient to accomplish prophylactic or therapeutic treatment either directly or indirectly. As is understood in the clinical context, an effective dosage of a drug, compound or pharmaceutical composition may or may not be achieved in conjunction with another drug, compound or pharmaceutical composition.

A “non-standard dosing regimen” refers to a regimen for administering an amount of a substance, agent, compound or pharmaceutical composition, which is different from the amount, dose or schedule typically used for that substance, agent, compound or pharmaceutical composition in a clinical or therapeutic setting. A "non-standard dosing regimen", includes a "non-standard dose" or a "non-standard dosing schedule."

A "low dose amount regimen" refers to a dosing regimen where the amount of one or more of the substances, agents, compounds or pharmaceutical compositions in the regimen is dosed at a lower amount or dose than typically used in a clinical or therapeutic setting for that agent, for example when that agent is dosed as a single agent therapy.

The retinoblastoma susceptibility gene (RB1) was the first tumor suppressor gene to be molecularly defined. The retinoblastoma gene product, RB, is frequently mutated or deleted in retinoblastoma and osteosarcoma, and is mutated or deleted with variable frequency in other tumor types, such as prostate cancer (including neuroendocrine prostate carcinoma), breast cancer (including triple negative breast cancer, TNBC), lung cancer (including small cell lung cancer, SCLC, and non-small cell lung cancer, NSCLC), liver cancer, bladder cancer, ovarian cancer, uterine cancer, cervical cancer, stomach cancer, esophageal cancer, head and neck cancer, glioblastoma, and lymphoma. In human cancers, the function of RB may be disrupted through neutralization by a binding protein, (e.g., the human papilloma virus-E7 protein in cervical carcinoma, Ishiji, T, 2000, *J Dermatol.,* 27: 73-86) or deregulation of pathways ultimately responsible for its phosphorylation.

By "RB pathway" it is meant the entire pathway of molecular signaling that includes retinoblastoma protein (RB), and other protein/protein families in the pathway, including but not limited to CDK, E2f, atypical protein kinase C, and Skp2. Inactivation of the RB pathway often results from perturbation of p161NK4a, Cyclin D1, and CDK4.

The terms "RB+," "RB plus," "RB-proficient" or "RB-positive" may be used to describe cells expressing detectable amounts of functional RB protein. RB-positive includes wild-type and non-mutated RB protein. A wild-type RB (RB-WT) is generally understood to mean that form of the RB protein which is normally present in a corresponding population and which has the function which is currently assigned to this protein. RB-positive may be cells which contain a functional RB gene. Cells which are RB-positive may also be cells that can encode a detectable RB protein function.

The terms "RB−," "RB minus," "RB-deficient" or "RB-negative" describe several types of cell where the function of RB is disrupted, including cells which produce no detectable amounts of functional RB protein. Cells that are RB-negative may be cells which do not contain a functional RB gene. Cells that are RB-negative may also be cells that can encode an RB protein, but in which the protein does not function properly.

In some embodiments of each of the methods and uses described herein, the cancer is characterized as retinoblastoma wild type (RB-WT). In some embodiments of each of the methods and uses described herein, the cancer is characterized as RB-positive or RB-proficient. Such RB-positive or RB-proficient cancers contain at least some functional retinoblastoma genes. In some embodiments, such RB-WT, RB-positive or RB-proficient cancers are characterized as RB1-WT, RB1-positive or RB1-proficient cancers.

In some embodiments of each of the methods and uses described herein, the cancer is characterized as RB-negative or RB-deficient. Such RB-negative or RB-deficient cancers may be characterized by loss of function mutations, which may encode missense mutations (i.e., encode the wrong amino acid) or nonsense mutatons (i.e., encode a stop codon). Alternatively, such RB-negative cancers may be characterized by deletion of all or part of the retinoblastoma gene. In some embodiments, such RB-negative or RB-deficient cancers are characterized as RB1-negative or RB1-deficient.

"Tumor" as it applies to a subject diagnosed with, or suspected of having, a cancer refers to a malignant or potentially malignant neoplasm or tissue mass of any size and includes primary tumors and secondary neoplasms. A solid tumor is an abnormal growth or mass of tissue that usually does not contain cysts or liquid areas. Examples of solid tumors are sarcomas, carcinomas, and lymphomas. Leukaemia's (cancers of the blood) generally do not form solid tumors (National Cancer Institute, Dictionary of Cancer Terms).

"Tumor burden" or "tumor load", refers to the total amount of tumorous material distributed throughout the body. Tumor burden refers to the total number of cancer cells or the total size of tumor(s), throughout the body, including lymph nodes and bone marrow. Tumor burden can be determined by a variety of methods known in the art, such as, e.g., using calipers, or while in the body using imaging techniques, e.g., ultrasound, bone scan, computed tomography (CT), or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CR or MRI scans.

The term "patient" or "subject" refer to any single subject for which therapy is desired or that is participating in a clinical trial, epidemiological study or used as a control, including humans and mammalian veterinary patients such as cattle, horses, dogs and cats. In some embodiments, the subject is a human.

In some embodiments of each of the methods and uses described herein, the patient or subject is an adult human. In some embodiments, the subject is a woman of any menopausal status or a man. In some embodiments, the subject is a post-menopausal woman or a man. In some embodiments, the subject is a post-menopausal woman. In some embodiments, the subject is a pre-menopausal or peri-menopausal woman. In some embodiments, the subject is a pre-menopausal or peri-menopausal woman treated with a luteinizing hormone-releasing hormone (LHRH) agonist. In some such embodiments, the subject is a man. In some embodiments, the subject is a man treated with an LHRH or gonadotropin-releasing hormone (GnRH) agonist.

The terms "treat" or "treating" of a cancer as used herein means to administer a compound of the present invention to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, inhibiting the progress of, or preventing or delaying recurrence the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject, for example, following surgery or radiotherapy.

For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of a tumor; remission of the cancer; decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer.

Positive therapeutic effects in cancer can be measured in several ways (see, for example, W. A. Weber, Assessing tumor response to therapy, J. Nucl. Med. 50 Suppl. 1:1S-10S (2009). For example, with respect to tumor growth inhibition (T/C), according to the National Cancer Institute (NCI) standards, a T/C less than or equal to 42% is the minimum level of anti-tumor activity. A T/C<10% is considered a high anti-tumor activity level, with T/C (%)=median tumor volume of the treated/median tumor volume of the control×100.

In some embodiments, the treatment achieved by a compound of the invention is defined by reference to any of the following: partial response (PR), complete response (CR), overall response (OR), objective response rate (ORR), progression free survival (PFS), radiographic PFS, metastasis fee survival (MFS), disease free survival (DFS) and overall survival (OS).

As used herein, the term "complete response" or "CR" means the disappearance of all signs of cancer (e.g., disappearance of all target lesions) in response to treatment. This does not always mean the cancer has been cured.

As used herein, the term "disease-free survival" (DFS) means the length of time after primary treatment for a cancer ends that the patient survives without any signs or symptoms of that cancer.

As used herein, the term "duration of response" (DoR) means the length of time that a tumor continues to respond to treatment without the cancer growing or spreading.

Treatments that demonstrate improved DoR can produce a durable, meaningful delay in disease progression.

As used herein, the terms "objective response" and "overall response" refer to a measurable response, including complete response (CR) or partial response (PR). The term "overall response rate" (ORR) refers to the sum of the complete response (CR) rate and the partial response (PR) rate.

As used herein, the term "overall survival" (OS) means the length of time from either the date of diagnosis or the start of treatment for a disease, such as cancer, that patients diagnosed with the disease are still alive. OS is typically measured as the prolongation in life expectancy in patients who receive a certain treatment as compared to patients in a control group (i.e., taking either another drug or a placebo).

As used herein, the term "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

As used herein, the term "progression free survival" or "PFS" refers to the length of time during and after treatment during which the disease being treated (e.g., cancer) does not get worse. PFS, also referred to as "Time to Tumor Progression", may include the amount of time patients have experienced a CR or PR, as well as the amount of time patients have experienced SD.

As used herein, the term "progressive disease" or "PD" refers to a cancer that is growing, spreading or getting worse. In some embodiments, PR refers to at least a 20% increase in the SLD of target lesions, taking as reference the smallest SLD recorded since the treatment started, or to the presence of one or more new lesions.

As used herein, the term "stable disease" (SD) refers to a cancer that is neither decreasing nor increasing in extent or severity.

As used herein, the term "sustained response" refers to the sustained effect on reducing tumor growth after cessation of a treatment. For example, the tumor size may be the same size or smaller as compared to the size at the beginning of the medicament administration phase. In some embodiments, the sustained response has a duration of at least the same as the treatment duration, at least 1.5-, 2-, 2.5-, or 3-times the length of the treatment duration, or longer.

The anti-cancer effect of the method of treating cancer, including "objective response," "complete response," "partial response," "progressive disease," "stable disease," "progression free survival," "duration of response," as used herein, may be defined and assessed by the investigators using RECIST v1.1 (Eisenhauer et al., New response evaluation criteria in solid tumours: Revised RECIST guideline (version 1.1), Eur J of Cancer, 2009; 45(2):228-47).

In some embodiments of each of the methods and uses described herein, the invention relates to neoadjuvant therapy, adjuvant therapy, first-line therapy, second-line therapy, second-line or later lines of therapy, or third-line or later lines of therapy. In each case as further described herein, the cancer may be localized, advanced or metastatic, and the intervention may occur at point along the disease continuum (i.e., at any stage of the cancer).

The treatment regimen for a compound of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrat-testy and the Wilcon on-test.

The terms "treatment regimen", "dosing protocol" and "dosing regimen" may be used interchangeably to refer to the dose and timing of administration of the crystalline or amorphous form of PF-07220060, or a pharmaceutical composition comprising the crystalline or amorphous form of PF-07220060, as described herein, alone or in combination with an additional anticancer agent. In preferred embodiments, the treatment regimen relates to crystalline PF-07220060 monohydrate (Form 2). In some embodiments, the treatment regimen relates to anhydrous crystalline PF-07220060 (Form 6), anhydrous crystalline PF-07220060 (Form 11), or amorphous PF-07220060 (Form 8). "Ameliorating" means reducing to some extent or improving one or more symptoms upon treatment with a compound or drug, such as the crystalline or amorphous form of PF-07220060, or a pharmaceutical composition comprising the crystalline or amorphous form of PF-07220060, as described herein, as compared to not administering the compound. "Ameliorating" also includes shortening or reduction in duration of a symptom. that is, reducing to some extent, preferably, eliminating a symptom.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). In frequent embodiments of the methods provided herein, the abnormal cell growth is cancer.

Abnormal cell growth includes the abnormal growth of: (1) tumors characterized by amplification or overexpression of CDK4, CDK6 and/or cyclin D1 (CCND1); (2) tumors that proliferate by aberrant CDK4 activation; and (3) tumors that are resistant to endocrine therapy, CDK4 and/or CDK6 inhibition, HER2 antagonists, taxanes, platinum agents, or other standard of care agents.

In some embodiments, the methods and uses of the present invention may further comprise one or more additional anti-cancer agents. In some embodiments, the additional anti-cancer agent is selected from the group consisting of an anti-tumor agent, an anti-angiogenesis agent, a signal transduction inhibitor, and an antiproliferative agent. In some embodiments, the additional anti-cancer agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, and endocrine therapeutic agents, such as antiandrogens, androgen deprivation therapy (ADT), and antiestrogens. Additional anti-cancer agents may include small molecules therapeutics and pharmaceutically acceptable salts or solvates thereof, therapeutic antibodies, antibody-drug conjugates (ADCs), proteolysis targeting chimeras, or antisense molecules.

In some embodiments, the additional anti-cancer agent is an antiestrogen, wherein the antiestrogen is an aromatase inhibitor, a SERD, or a SERM. In some embodiments, the antiestrogen is an aromatase inhibitor. In some such embodiments, the aromatase inhibitor is selected from the group consisting of letrozole, anastrozole, and exemestane. In some such embodiments, the aromatase inhibitor is letrozole. In some embodiments, the antiestrogen is a SERD. In some such embodiments, the SERD is selected from the group consisting of fulvestrant, elacestrant (RAD-1901, Radius Health), SAR439859 (Sanofi), RG6171 (Roche), AZD9833 (AstraZeneca), AZD9496 (AstraZeneca), rintodestrant (G1 Therapeutics), ZN-c5 (Zentalis), LSZ102 (Novartis), D-0502 (Inventisbio), LY3484356 (Lilly), and SHR9549 (Jiansu Hengrui Medicine). In some such embodiments, the SERD is fulvestrant. In some embodiments, the antiestrogen is a SERM. In some such embodiments, the SERM is selected from the group consisting of tamoxifen, raloxifene, toremifene, lasofoxifene, bazedoxifene and afimoxifene. In some such embodiments, the SERM is tamoxifen or raloxifene.

In some embodiments, the additional anti-cancer agent is an antiandrogen, such as abiraterone, apalutamide, bicalutamide, cyproterone, enzalutamide, flutamide, or nilutamide. In some embodiments, the method or use further comprises androgen deprivation therapy (ADT), e.g., a luteinizing hormone-releasing hormone (LHRH) agonist, a LHRH antagonist, a gonadotropin releasing hormone (GnRH) agonist or a GnRH antagonist.

In some embodiments, the methods and uses of the present invention further comprise one or more additional anti-cancer agents selected from the following: Anti-angiogenesis agents include, for example, VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors.

Signal transduction inhibitors include, for example, kinase inhibitors (e.g., inhibitors of tyrosine kinases, serine/threonine kinases or cyclin dependent kinases), proteasome inhibitors, PI3K/AKT/mTOR pathway inhibitors, phosphoinositide 3-kinase (PI3K) inhibitors, isocitrate dehydrogenase 1 and 2 (IDH1 and IDH2) inhibitors, B-cell lymphoma 2 (BCL2) inhibitors, neurotrophin receptor kinase (NTRK) inhibitors, Rearranged during Transfection (RET) inhibitors, Notch inhibitors, PARP inhibitors, Hedgehog pathway inhibitors, and selective inhibitors of nuclear export (SINE).

Examples of signal transduction inhibitors include, but are not limited to: acalabrutinib, afatinib, alectinib, alpelisib, axitinib, binimetinib, bortezomib, bosutinib, brigatinib, cabozantinib, carfilzomib, ceritinib, cobimetinib, copanlisib, crizotinib, dabrafenib, dacomitinib, dasatinib, duvelisib, enasidenib, encorafenib, entrectinib, erlotinib, gefitinib, gilteritinib, glasdegib, ibrutinib, idelalisib, imatinib, ipatasertib, ivosidenib, ixazomib, lapatinib, larotrectinib, lenvatinib, lorlatinib, midostaurin, neratinib, nilotinib, niraparib, olaparib, osimertinib, pazopanib, ponatinib, regorafenib, rucaparib, ruxolitinib, sonidegib, sorafenib, sunitinib, talazoparib, trametinib, vandetanib, vemurafenib, venetoclax, and vismodegib, or pharmaceutically acceptable salts and solvates thereof.

Antineoplastic agents include, for example, alkylating agents, platinum coordination complexes, cytotoxic antibiotics, antimetabolies, biologic response modifiers, histone deacetylate (HDAC) inhibitors, hormonal agents, monoclonal antibodies, growth factor inhibitors, taxanes, topoisomerase inhibitors, *Vinca* alkaloids and miscellaneous agents.

Alkylating agents include: altretamine, bendamustine, busulfan, carmustine, chlorambucil, cyclophosphamide, dacarbazine, ifosfamide, lomustine, mechlorethamine, melphalan, procarbazine, streptozocin, temozolomide, thiotepa, and trabectedin.

Platinum coordination complexes (also referred to herein as "platinum agents") include: carboplatin, cisplatin, and oxaliplatin.

Cytotoxic antibiotics include: bleomycin, dactinomycin, daunorubicin, doxorubicin, epirubicin, idarubicin, mitomycin, mitoxantrone, plicamycin, and valrubicin.

Antimetabolites include: antifolates, such as methotrexate, pemetrexed, pralatrexate, and trimetrexate, purine analogues, such as azathioprine, cladribine, fludarabine, mercaptopurine, and thioguanine; and pyrimidine analogues such as azacitidine, capecitabine, cytarabine, decitabine, floxuridine, fluorouracil, gemcitabine, and trifluridine/tipracil.

Biologic response modifiers include: aldesleukin (IL-2), denileukin diftitox, and interferon gamma.

Histone deacetylase inhibitors include belinostat, panobinostat, romidepsin, and vorinostat.

Hormonal agents include antiandrogens, antiestrogens, gonadotropin releasing hormone (GnRH) analogues and peptide hormones. Examples of antiestrogens include: aromatase inhibitors, such as letrozole, anastrozole, and exemestane; SERDs, such as fulvestrant, elacestrant (RAD-1901, Radius Health), SAR439859 (Sanofi), RG6171 (Roche), AZD9833 (AstraZeneca), AZD9496 (AstraZeneca), rintodestrant (G1 Therapeutics), ZN-c5 (Zentalis), LSZ102 (Novartis), D-0502 (Inventisbio), LY3484356

(Lilly), SHR9549 (Jiansu Hengrui Medicine); and SERMs, such as tamoxifen, raloxifene, toremifene, lasofoxifene, bazedoxifene, afimoxifene. Examples of GnRH analogues include: degarelix, goserelin, histrelin, leuprolide, and triptorelin. Examples of peptide hormones include: lanreotide, octreotide, and pasireotide. Examples of antiandrogens include: abiraterone, apalutamide, bicalutamide, cyproterone, enzalutamide, flutamide, and nilutamide, and pharmaceutically acceptable salts and solvates thereof.

Monoclonal antibodies include: alemtuzumab, atezolizumab, avelumab, bevacizumab, blinatumomab, brentuximab, cemiplimab, cetuximab, daratumumab, dinutuximab, durvalumab, elotuzumab, gemtuzumab, inotuzumab ozogamicin, ipilimumab, mogamulizumab, moxetumomab pasudotox, necitumumab, nivolumab, ofatumumab, olaratumab, panitumumab, pembrolizumab, pertuzumab, ramucirumab, rituximab, tositumomab, and trastuzumab.

Taxanes include: cabazitaxel, docetaxel, paclitaxel and paclitaxel albumin-stabilized nanoparticle formulation (Nab-paclitaxel).

Topoisomerase inhibitors include: etoposide, irinotecan, teniposide, and topotecan.

Vinca alkaloids include: vinblastine, vincristine, and vinorelbine, and pharmaceutically acceptable salts thereof.

Miscellaneous antineoplastic agents include: asparaginase (pegaspargase), bexarotene, eribulin, everolimus, hydroxyurea, ixabepilone, lenalidomide, mitotane, omacetaxine, pomalidomide, tagraxofusp, telotristat, temsirolimus, thalidomide, and venetoclax.

In some embodiments, the additional anti-cancer agent is selected from the group consisting of: abiraterone acetate; acalabrutinib; ado-trastuzumab emtansine; afatinib dimaleate; afimoxifene; aldesleukin; alectinib; alemtuzumab; alpelisib; amifostine; anastrozole; apalutamide; aprepitant; arsenic trioxide; asparaginase *Erwinia chrysanthemi*; atezolizumab; avapritinib; avelumab; axicabtagene ciloleucel; axitinib; azacitidine; AZD9833 (AstraZeneca); AZD9496 (AstraZeneca); bazedoxifene; belinostat; bendamustine hydrochloride; bevacizumab; bexarotene; bicalutamide; binimetinib; bleomycin sulfate; blinatumomab; bortezomib; bosutinib; brentuximab vedotin; brigatinib; cabazitaxel; cabozantinib-s-malate; calaspargase pegol-mknl; capecitabine; caplacizumab-yhdp; capmatinib hydrochloride; carboplatin; carfilzomib; carmustine; cemiplimab-rwlc; ceritinib; cetuximab; chlorambucil; cisplatin; cladribine; clofarabine; cobimetinib; copanlisib hydrochloride; crizotinib; cyclophosphamide; cytarabine; D-0502 (Inventisbio); dabrafenib mesylate; dacarbazine; dacomitinib; dactinomycin; daratumumab; daratumumab and hyaluronidase-fihj; darbepoetin alfa; darolutamide; dasatinib; daunorubicin hydrochloride; decitabine; defibrotide sodium; degarelix; denileukin diftitox; denosumab; dexamethasone; dexrazoxane hydrochloride; dinutuximab; docetaxel; doxorubicin hydrochloride; durvalumab; duvelisib; elacestrant; elotuzumab; eltrombopag olamine; emapalumab-lzsg; enasidenib mesylate; encorafenib; enfortumab vedotin-ejfv; entrectinib; enzalutamide; epirubicin hydrochloride; epoetin alfa; erdafitinib; eribulin mesylate; erlotinib hydrochloride; etoposide; etoposide phosphate; everolimus; exemestane; fam-trastuzumab deruxtecan-nxki; fedratinib hydrochloride; filgrastim; fludarabine phosphate; fluorouracil; flutamide; fostamatinib disodium; fulvestrant; gefitinib; gemcitabine hydrochloride; gemtuzumab ozogamicin; gilteritinib fumarate; glasdegib maleate; glucarpidase; goserelin acetate; granisetron; granisetron hydrochloride; hydroxyurea; ibritumomab tiuxetan; ibrutinib; idarubicin hydrochloride; idelalisib; ifosfamide; imatinib mesylate; imiquimod; inotuzumab ozogamicin; interferon alfa-2b recombinant; iobenguane 1-131; ipatasertib; ipilimumab; irinotecan hydrochloride; isatuximab-irfc; ivosidenib; ixabepilone; ixazomib citrate; lanreotide acetate; lapatinib ditosylate; larotrectinib sulfate; lasofoxifene; lenalidomide; lenvatinib mesylate; letrozole; leucovorin calcium; leuprolide acetate; lomustine; lorlatinib; LSZ102 (Novartis); lurbinectedin; LY3484356 (Lilly); megestrol acetate; melphalan; melphalan hydrochloride; mercaptopurine; methotrexate; midostaurin; mitomycin; mitoxantrone hydrochloride; mogamulizumab-kpkc; moxetumomab pasudotox-tdfk; necitumumab; nelarabine; neratinib maleate; nilotinib; nilutamide; niraparib tosylate monohydrate; nivolumab; obinutuzumab; ofatumumab; olaparib; omacetaxine mepesuccinate; ondansetron hydrochloride; osimertinib mesylate; oxaliplatin; paclitaxel; paclitaxel albumin-stabilized nanoparticle formulation; palifermin; palonosetron hydrochloride; pamidronate disodium; panitumumab; panobinostat; pazopanib hydrochloride; pegaspargase; pegfilgrastim; peginterferon alfa-2b; pembrolizumab; pemetrexed disodium; pemigatinib; pertuzumab; pexidartinib hydrochloride; plerixafor; polatuzumab vedotin-piiq; pomalidomide; ponatinib hydrochloride; pralatrexate; prednisone; procarbazine hydrochloride; propranolol hydrochloride; radium 223 dichloride; raloxifene hydrochloride; ramucirumab; rasburicase; ravulizumab-cwvz; recombinant interferon alfa-2b; regorafenib; RG6171 (Roche); rintodestrant; ripretinib; rituximab; rolapitant hydrochloride; romidepsin; romiplostim; rucaparib camsylate; ruxolitinib phosphate; sacituzumab govitecan-hziy; SAR439859 (Sanofi); selinexor; selpercatinib; selumetinib sulfate; SHR9549 (Jiansu Hengrui Medicine); siltuximab; sipuleucel-t; sonidegib; sorafenib tosylate; tagraxofusp-erzs; talazoparib tosylate; talimogene laherparepvec; tamoxifen citrate; tazemetostat hydrobromide; temozolomide; temsirolimus; thalidomide; thioguanine; thiotepa; tisagenlecleucel; tocilizumab; topotecan hydrochloride; toremifene; trabectedin; trametinib; trastuzumab; trastuzumab and hyaluronidase-oysk; trifluridine and tipiracil hydrochloride; tucatinib; uridine triacetate; valrubicin; vandetanib; vemurafenib; venetoclax; vinblastine sulfate; vincristine sulfate; vinorelbine tartrate; vismodegib; vorinostat; zanubrutinib; ziv-aflibercept; ZN-c5 (Zentalis); and zoledronic acid; or free base, pharmaceutically acceptable salt (including an alternative salt forms to the salts named above), or solvate forms of the foregoing; or combinations thereof.

The terms "cancer" or "cancerous" refer to or describe malignant and/or invasive growth or tumor caused by abnormal cell growth. As used herein "cancer" refers to solid tumors named for the type of cells that form them, as well as cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

The efficacy of the methods and uses described herein in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD-1 or PD-L1 antagonists and the like. The methods and uses of the current invention may further comprise one or more additional anti-cancer agents.

Administration of crystalline or amorphous forms of the invention may be affected by any method that enables delivery of the compound to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, the crystalline or amorphous form of the present invention may be administered as a single bolus, as several divided doses administered over time, or the dose may be proportionally reduced or increased as indicated by the exigencies of the therapeutic situation. It may be particularly advantageous to formulate a therapeutic agent in a dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention may be dictated by and directly dependent on (a) the unique characteristics of the solid form and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compounds or pharmaceutical compositions, taking into consideration factors such as the severity of the disorder or condition, the rate of administration, the disposition of the compound and the discretion of the prescribing physician. The dosage ranges set forth herein are exemplary only and are not intended to limit the scope or practice of the claimed solid form or pharmaceutical composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein The dosage of the crystalline or amorphous form of the invention is typically in the range of from about 0.001 to about 100 mg per kg body weight per day, preferably about 1 to about 35 mg/kg/day, in single or divided doses. For a 70 kg human, this would amount to about 0.01 to about 7 g/day, preferably about 0.02 to about 2.5 g/day. In some instances, dosage levels below the lower limit of the aforesaid range may be more than adequate, while in other cases still larger doses may be employed without causing any harmful side effects, provided that such larger doses are first divided into several small doses for administration throughout the day. The dosage may be administered as a single dose (QD), or optionally may be subdivided into smaller doses, suitable for BID (twice daily), TID (three times daily) or QID (four times daily) administration. The dosage regimen may be adjusted to provide the optimal therapeutic response. For example, the dose may be proportionally reduced or increased as indicated by the exigencies of the therapeutic situation, including temporary or permanent dose reductions if required to ameliorate or prevent side effects.

Repetition of the administration or dosing regimens, or adjustment of the administration or dosing regimen may be conducted as necessary to achieve the desired treatment. A "continuous dosing schedule" as used herein is an administration or dosing regimen without dose interruptions, e.g., without days off treatment. Repetition of 21 day or 28 day treatment cycles without dose interruptions between the treatment cycles is an example of a continuous dosing schedule.

In some embodiments, the crystalline or amorphous form of the invention is administered at a daily dosage of from about 1 mg to about 1000 mg per day. In some embodiments, the crystalline or amorphous form of the invention is administered at a daily dosage from about 10 mg to about 500 mg per day, and in some embodiments, it is administered at a dosage of from about 25 mg to about 300 mg per day. In some embodiments it is administered at dosages of about 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 260, 270, 275, 280, 290, 300, 325, 350, 375, 400, 425, 450, 475 or 500 mg on a QD, BID, TID or QID schedule.

Repetition of the administration or dosing regimens, or adjustment of the administration or dosing regimen may be conducted as necessary to achieve the desired treatment. An "intermittent dosing schedule" refers to an administration or dosing regimen that includes a period of dose interruption, e.g. days off treatment. Repetition of 14 or 21 day treatment cycles with a 7 day treatment interruption between the treatment cycles is an example of an intermittent dosing schedule. Such schedules, with 2 or 3 weeks on treatment and 1 week off treatment, are sometimes referred to as a 2/1-week or 3/1-week treatment cycle, respectively. Alternatively, intermittent dosing may comprise a 7 day treatment cycle, with 5 days on treatment and 2 days off treatment.

A "continuous dosing schedule" as used herein is an administration or dosing regimen without dose interruptions, e.g. without days off treatment. Repetition of 21 or 28 day treatment cycles without dose interruptions between the treatment cycles is an example of a continuous dosing schedule.

In some embodiments, the crystalline or amorphous form of the invention is administered in an intermittent dosing schedule. In other embodiments, the crystalline or amorphous form of the invention is administered in a continuous dosing schedule.

A "pharmaceutical composition" refers to a mixture of one or more of the therapeutic agents described herein, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients.

As used herein, a "pharmaceutically acceptable carrier" refers to a carrier or diluent that does not cause significant irritation to an organism and does not abrogate the biological activity and properties of the active compound or therapeutic agent.

The pharmaceutical acceptable carrier may comprise any conventional pharmaceutical carrier or excipient. The choice of carrier and/or excipient will to a large extent depend on factors such as the particular mode of administration, the effect of the excipient on solubility and stability, and the nature of the dosage form.

In one embodiment, the invention relates to a pharmaceutical composition comprising crystalline PF-07220060 monohydrate (Form 2), and a pharmaceutically acceptable carrier or excipient.

In one embodiment, this invention relates to a pharmaceutical composition comprising amorphous PF-07220060 and a pharmaceutically acceptable carrier or excipient.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid pharmaceutical compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Pharmaceutical compositions of the present invention may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 19th Edition (1995).

The crystalline and amorphous forms of the invention may be administered orally. Oral administration may involve swallowing, so that the therapeutic agent enters the gastrointestinal tract, or buccal or sublingual administration may be employed by which the therapeutic agent enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The crystalline and amorphous forms of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the crystalline or amorphous form of PF-07220060 may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets may contain from about 1 wt % to about 80 wt % active agent, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated, or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Capsules (made, for example, from gelatin or HPMC), blisters and cartridges for use in an inhaler or insufflator may be formulated to contain a powder mix of the therapeutic agent, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles may be found in Verma et al, Current Status of Drug Delivery Technologies and Future Directions, Pharmaceutical Technology On-line, (2001) 25:1-14. The use of chewing gum to achieve controlled release is described in WO 00/35298. The disclosures of these references are incorporated herein by reference in their entireties.

The crystalline and amorphous forms of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of therapeutic agents used in the preparation of parenteral solutions may potentially be increased by the use of appropriate formulation techniques, such as the incorporation of solubility-enhancing agents.

The crystalline and amorphous forms of the invention may be in the form of a kit suitable for administration of the pharmaceutical composition. Such kits may comprise the active agent in the form of a pharmaceutical composition, which pharmaceutical composition comprises an active agent, or a pharmaceutically acceptable salt or solvate thereof, and a pharmaceutically acceptable carrier. The kit may contain means for separately retaining the pharmaceutical composition, such as a container, divided bottle, or divided foil packet. An example of such a kit is the familiar blister pack used for the packaging of tablets, capsules and the like. To assist in compliance, the kit typically includes directions for administration and may be provided with a memory aid.

The kit may further comprise other materials that may be useful in administering the medicament, such as diluents, filters, IV bags and lines, needles and syringes, and the like.

In some preferred embodiments, the embodiment is selected from the group consisting of embodiments E1 to E52:

E1. A crystalline form of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060) monohydrate (Form 2), having a $^{19}F$ solid state NMR spectrum comprising resonance (ppm) values of: −126.1 and −125.6 ppm±0.2 ppm.

E2. A crystalline form of PF-07220060 monohydrate (Form 2), having a powder X-ray diffraction (PXRD) pattern comprising peaks at 2θ values of: 9.6, 11.8 and 14.7°2θ±0.2°2θ.

E3. The crystalline form of embodiment E2, having a PXRD pattern further comprising a peak at a 2θ value of: 12.4°2θ±0.2°2θ.

E4. The crystalline form of embodiment E2 or E3, having a PXRD pattern further comprising a peak at a 2θ value of: 21.0°2θ±0.2°2θ.

E5. The crystalline form of embodiment E2, E3 or E4, having a Raman spectrum comprising wavenumber ($cm^{-1}$) values of: 1484, 1555 and 1587 $cm^{-1}$±2 $cm^{-1}$.

E6. The crystalline form of embodiment E5, having a Raman spectrum further comprising a wavenumber ($cm^{-1}$) value of: 1387 $cm^{-1}$±2 $cm^{-1}$.

E7. The crystalline form of embodiment E5 or E6, having a Raman spectrum further comprising a wavenumber ($cm^{-1}$) value of: 1395 $cm^{-1}$±2 $cm^{-1}$.

E8. The crystalline form of any one of embodiments E2 to E7, having a $^{13}C$ solid state NMR spectrum comprising resonance (ppm) values of: 22.8 and 163.0 ppm±0.2 ppm.

E9. The crystalline form of embodiment E8, having a $^{13}C$ solid state NMR spectrum further comprising one, two or three resonance (ppm) values selected from the group consisting of: 50.3, 109.8 and 129.1 ppm±0.2 ppm.

E10. The crystalline form of any one of embodiments E2 to E9, having a $^{19}F$ solid state NMR spectrum comprising a resonance (ppm) value of: −126.1 ppm±0.2 ppm.

E11. The crystalline form of any one of embodiments E2 to E10, having a $^{19}F$ solid state NMR spectrum further comprising a resonance (ppm) value of: −125.6 ppm±0.2 ppm.

E12. A crystalline form of PF-07220060 monohydrate (Form 2), having a $^{13}C$ solid state NMR spectrum comprising resonance (ppm) values of: 22.8 and 163.0 ppm±0.2 ppm.

E13. The crystalline form of embodiment E12, having a $^{13}C$ solid state NMR spectrum further comprising one, two or three resonance (ppm) values selected from the group consisting of: 50.3, 109.8 and 129.1 ppm±0.2 ppm.

E14. A crystalline form of PF-07220060 monohydrate (Form 2), having a Raman spectrum comprising wavenumber ($cm^{-1}$) values of: 1484, 1555 and 1587 $cm^{-1}$±2 $cm^{-1}$.

E15. The crystalline form of embodiment E14, having a Raman spectrum further comprising a wavenumber ($cm^{-1}$) value of: 1387 $cm^{-1}$±2 $cm^{-1}$.

E16. The crystalline form of embodiment E13 or E14, having a Raman spectrum further comprising a wavenumber ($cm^{-1}$) value of: 1395 $cm^{-1}$±2 $cm^{-1}$.

E17. A crystalline form of PF-07220060 (Form 2), having: (a) a powder X-ray diffraction (PXRD) pattern comprising peaks at 2θ values of: 9.6, 11.8 and 14.7°2θ±0.2° 2θ; (b) a Raman spectrum comprising wavenumber ($cm^{-1}$) values of: 1484, 1555 and 1587 $cm^{-1}$±2 $cm^{-1}$; (c) a $^{13}C$ solid state NMR spectrum comprising resonance (ppm) values of: 22.8 and 163.0 ppm±0.2 ppm; or (d) a $^{19}F$ solid state NMR spectrum comprising resonance (ppm) values of: −126.1 and −125.6 ppm±0.2 ppm; or any combination of (a), (b), (c) and (d).

E18. An anhydrous crystalline form of PF-07220060 (Form 6), having a $^{19}F$ solid state NMR spectrum comprising resonance (ppm) values of: −132.4 and −131.1 ppm±0.2 ppm.

E19. An anhydrous crystalline form of PF-07220060 (Form 6), having a $^{19}F$ solid state NMR spectrum comprising resonance (ppm) values of: −132.4 ppm±0.2 ppm.

E20. An anhydrous crystalline form of PF-07220060 (Form 6), having a $^{19}F$ solid state NMR spectrum comprising resonance (ppm) values of: −131.1 ppm±0.2 ppm.

E21. An anhydrous crystalline form of PF-07220060 (Form 6), having a powder X-ray diffraction (PXRD) pattern comprising peaks at 2θ values of:

(a) 6.8 and 10.1°2θ±0.2°2θ;
(b) 6.8, 10.1 and 12.2°2θ±0.2°2θ;
(c) 6.8, 10.1 and 17.8°2θ±0.2°2θ;
(d) 6.8, 10.1, 12.2 and 17.8°2θ±0.2°2θ;
(e) 8.5, 10.1 and 13.8°2θ±0.2°2θ;
(f) 6.8, 8.5 and 13.8°2θ±0.2°2θ;
(g) 6.8, 8.5, 10.1 and 13.8°2θ±0.2°2θ; or
(h) 6.8, 8.5, 10.1, 12.2 and 13.8°2θ±0.2°2θ.

E22. The crystalline form of any one of embodiments E18 to E21, having a Raman spectrum comprising wavenumber ($cm^{-1}$) values of: 1436, 1465 and 1566 $cm^{-1}$±2 $cm^{-1}$.

E23. The crystalline form of any one of embodiments E18 to E22, having a $^{13}C$ solid state NMR spectrum comprising resonance (ppm) values of: 54.7, 112.6 and 132.8 ppm±0.2 ppm.

E24. The crystalline form of embodiment E23, having a $^{13}C$ solid state NMR spectrum further comprising a resonance (ppm) value of: 49.2 ppm±0.2 ppm.

E25. The crystalline form of any one of embodiments E18 to E22, having a $^{13}C$ solid state NMR spectrum comprising two, three or four resonance (ppm) values selected from the group consisting of: 49.2, 54.7, 112.6 and 132.8 ppm±0.2 ppm.

E26. The crystalline form of any one of embodiments E18 to E25, having a $^{19}F$ solid state NMR spectrum comprising a resonance (ppm) value of: −132.4 ppm±0.2 ppm.

E27. The crystalline form of any one of embodiments E18 to E26, having a $^{19}F$ solid state NMR spectrum further comprising a resonance (ppm) value of: −131.1 ppm±0.2 ppm.

E28. An anhydrous crystalline form of PF-07220060 (Form 6), having a $^{13}C$ solid state NMR spectrum comprising resonance (ppm) values of: 54.7, 112.6 and 132.8 ppm±0.2 ppm.

E29. The crystalline form of embodiment E28, having a $^{13}C$ solid state NMR spectrum further comprising a resonance (ppm) value of: 49.2 ppm±0.2 ppm.

E30. An anhydrous crystalline form of PF-07220060 (Form 6), having a Raman spectrum comprising wavenumber ($cm^{-1}$) values of: 1436 and 1566 $cm^{-1}$±2 $cm^{-1}$.

E31. The crystalline form of embodiment E30, having a Raman spectrum further comprising a wavenumber ($cm^{-1}$) value of: 1465 $cm^{-1}$±2 $cm^{-1}$.

E32. An anhydrous crystalline form of PF-07220060 (Form 6), having:

(a) a powder X-ray diffraction (PXRD) pattern comprising peaks at 2θ values of:
(i) 6.8 and 10.1°2θ±0.2°2θ;
(ii) 6.8, 10.1 and 12.2°2θ±0.2°2θ;
(iii) 6.8, 10.1 and 17.8°2θ±0.2°2θ;
(iv) 6.8, 10.1, 12.2 and 17.8°2θ±0.2°2θ;
(v) 8.5, 10.1 and 13.8°2θ±0.2°2θ;
(vi) 6.8, 8.5 and 13.8°2θ±0.2°2θ;
(vii) 6.8, 8.5, 10.1 and 13.8°2θ±0.2°2θ; or
(viii) 6.8, 8.5, 10.1, 12.2 and 13.8°2θ±0.2°2θ;
(b) a Raman spectrum comprising wavenumber ($cm^{-1}$) values of: 1436, 1465 and 1566 $cm^{-1}$±2 $cm^{-1}$;
(c) a $^{13}C$ solid state NMR spectrum comprising resonance (ppm) values of: 54.7, 112.6 and 132.8 ppm±0.2 ppm; or
(d) a $^{19}F$ solid state NMR spectrum comprising resonance (ppm) values of: −132.4 and −131.1 ppm±0.2 ppm;

or any combination of two or more of (a), (b), (c) and (d).

E33. An anhydrous crystalline form of PF-07220060 (Form 11), having a powder X-ray diffraction (PXRD) pattern essentially the same as in FIG. 17.

E34. The crystalline form of any one of embodiments E1 to E17, wherein the crystalline form is substantially pure crystalline PF-07220060 monohydrate (Form 2).

E35. The crystalline form of any one of embodiments E18 to E32, wherein the crystalline form is substantially pure anhydrous crystalline PF-07220060 (Form 6).

E36. The crystalline form of embodiment E33, wherein the crystalline form is substantially pure anhydrous crystalline PF-07220060 (Form 11).

E37. A pharmaceutical composition comprising the crystalline form of any one of embodiments E1 to E17 and E34, and a pharmaceutically acceptable carrier or excipient.

E38. A pharmaceutical composition comprising the crystalline form of any one of embodiments E18 to E32 and E35, and a pharmaceutically acceptable carrier or excipient.

E39. An amorphous form of PF-07220060 (Form 8).

E40. The amorphous form of embodiment E39, having a powder X-ray diffraction (PXRD) pattern comprising a broad peak at diffraction angles (2θ) from about 4 to about 40°2θ±0.5°2θ.

E41. The amorphous form of embodiment E39 or E40, having a powder X-ray diffraction (PXRD) pattern essentially the same as in FIG. 8.

E42. The amorphous form of any one of embodiments E39 to E41, having a $^{19}F$ solid state NMR spectrum comprising a resonance (ppm) value of: −127.5 ppm±0.5 ppm.

E43. The amorphous form of embodiment E42, having a $^{13}C$ solid state NMR spectrum comprising resonance (ppm) values of: 20.9, 49.3 and 116.6 ppm±0.5 ppm.

E44. The amorphous form of any one of embodiments E39 to E43, wherein the amorphous form is substantially pure amorphous PF-07220060 (Form 8).

E45. A pharmaceutical composition comprising the amorphous form of any one of embodiments E39 to E44, and a pharmaceutically acceptable carrier or excipient.

E46. A method of treating cancer in a subject in need thereof, comprising administering to the subject a therapeutically effective amount of the crystalline form of any one of embodiments E1 to E36 or the amorphous form of any one of embodiments E39 to E45.

E47. A method of treating cancer in a subject in need thereof, comprising administering to the subject a therapeutically effective amount of the pharmaceutical composition of embodiment E37, E38 or E45.

E48. The method of embodiment E46 or E47, wherein the cancer is selected from the group consisting of breast cancer, prostate cancer, lung cancer, liver cancer, kidney cancer, bladder cancer, ovarian cancer, peritoneal cancer, fallopian tube cancer, cervical cancer, uterine cancer, pancreatic cancer, stomach cancer, colorectal cancer, esophageal cancer, head and neck cancer, testicular cancer, adrenal cancer, skin cancer, brain cancer, sarcoma, and lymphoma.

E49. The crystalline form of any one of embodiments E1 to E36 or the amorphous form of any one of embodiments E39 to E45 for use in treating cancer.

E50. The pharmaceutical composition of embodiment E37, E38 or E45 for use in treating cancer.

E51. The crystalline form of embodiment E49 or the pharmaceutical composition of E50, wherein the cancer is selected from the group consisting of breast cancer, prostate cancer, lung cancer, liver cancer, kidney cancer, bladder cancer, ovarian cancer, peritoneal cancer, fallopian tube cancer, cervical cancer, uterine cancer, pancreatic cancer, stomach cancer, colorectal cancer, esophageal cancer, head and neck cancer, testicular cancer, adrenal cancer, skin cancer, brain cancer, sarcoma, and lymphoma.

E52. Use of the crystalline form of any one of embodiments E1 to E36 or the amorphous form of any one of embodiments E39 to E45 for the manufacture of a medicament for treating cancer.

EXAMPLES

The examples and preparations provided below further illustrate and exemplify aspects and embodiments of the invention. It is to be understood that the scope of the present invention is not limited by the scope of the following examples.

General Method 1A. Powder X-ray Diffraction (PXRD)

Instrument Method:

Powder X-ray diffraction analysis was conducted using a Bruker AXS D8 Endeavor diffractometer equipped with a copper radiation source. The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected at the copper (Cu) wavelength (CuKα=1.5418λ) in the Theta-Theta goniometer from 3.0 to 40.0 degrees 2-Theta. A step size of 0.01 degrees and a step time of 1.0 second was used for Form 2, Form 6 and Form 8. A step size of 0.02 degrees and a step time of 0.3 seconds was used for Form 11. The antiscatter screen was set to a fixed distance of 1.5 mm. Samples were rotated during data collection. Samples were prepared by placing them in a silicon low background sample holder and rotated during collection. Data were collected using Bruker DIFFRAC Plus software and analysis was performed by EVA diffract plus software.

Peak Picking Method:

The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to plus or minus (±) 0.2°2-Theta (USP-941) for crystalline forms, and up to plus or minus (±) 0.5°2-Theta for amorphous forms.

General Method 1B. Powder X-Ray Diffraction (PXRD)

Instrument Method:

Powder X-ray diffraction analysis was conducted using a Bruker AXS D8 Endeavor diffractometer equipped with a copper radiation source. The divergence slit was set at 10 mm continuous illumination. Diffracted radiation was detected by a LYNXEYE_EX detector, with the secondary slit set at 5.50 mm. The X-ray tube voltage and amperage were set to 40 kV and 40 mA respectively. Data was collected at the Cu wavelength (CuKα=1.5418λ) in the Theta-Theta goniometer from 3.0 to 40.0 degrees 2-Theta using a step size of 0.02 degrees and a step time of 0.5 second for Form 1. The antiscatter screen was in place. Samples were prepared by placing them in a silicon low background sample holder and rotated during collection. Data were collected using Bruker DIFFRAC Plus software and analysis was performed by EVA diffract plus software.

Peak Selection:

The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked, and peak positions were adjusted to the peak maximum. Peaks with relative intensity of ≥3% were generally chosen. Typically, the peaks which were not resolved or were consistent with noise were not selected. A typical error associated with the peak position from PXRD stated in USP up to plus or minus (±) 0.2°2-Theta (USP-941) for crystalline forms, and up to plus or minus (±) 0.5°2-Theta for amorphous forms.

General Method 2. Raman Spectroscopy

Instrument Method:

Raman spectra were collected using a Thermo Scientific iS50 FT-Raman accessory attached to the FT-IR bench. A CaF2 beam splitter is utilized in the FT-Raman configuration. The spectrometer is equipped with a 1064 nm diode laser and a room temperature InGaAs detector. Prior to data acquisition, instrument performance and calibration verifications were conducted using polystyrene. Samples were analyzed in glass NMR tubes, as tablets or in a suitable sample holder held static during data collection. The spectra were collected using between 0.1 and 0.5 W of laser power and 512 co-added scans. The collection range was 3700-100 $cm^{-1}$. The API spectra were recorded using 2 $cm^{-1}$ resolution, and Happ-Genzel apodization was utilized for all of the spectra. Multiple spectra were recorded, and the reported spectrum is representative of two spots.

Peak Picking Method:

The intensity scale was normalized to 1 prior to peak picking. Peaks were manually identified using the Thermo Nicolet Omnic 9.7.46 software. Peak position was picked at the peak maximum, and peaks were only identified as such, if there was a slope on each side; shoulders on peaks were not included. For neat PF-07220060 Form 2 an absolute threshold of 0.06 with a sensitivity of 75 was utilized during peak picking.

The peak position has been rounded to the nearest whole number using standard practice (0.5 rounds up, 0.4 rounds down). Peaks with normalized peak intensity between (1-0.75), (0.74-0.30), (0.29-0) were labeled as strong, medium and weak, respectively.

General Method 3. $^{13}C$ Solid State NMR (ssNMR) Spectroscopy

Instrument Method:

Solid-state NMR (ssNMR) analysis was conducted on a CPMAS probe positioned into a Bruker-BioSpin Avance III 500 MHz ($^{1}H$ frequency) NMR spectrometer. Material was packed into a 4 mm rotor. A magic angle spinning rate of 15.0 kHz was used. Spectra were collected at ambient temperature (temperature uncontrolled).

$^{13}C$ ssNMR spectra were collected using a proton decoupled cross-polarization magic angle spinning (CP-MAS) experiment. A phase modulated proton decoupling field of 80-100 kHz was applied during spectral acquisition. The cross-polarization contact time was set to 2 ms. Spectra were collected with a recycle delay of 3.25 seconds for Form 1 and 3.5 seconds for Form 2, Form 6 and Form 8. The number of scans was adjusted to obtain an adequate signal to noise ratio. The $^{13}C$ chemical shift scale was referenced using a $^{13}C$ CPMAS experiment on an external standard of crystalline adamantane, setting its up-field resonance to 29.5 ppm.

$^{19}F$ ssNMR spectra were collected using a proton decoupled magic angle spinning (MAS) experiment. A phase modulated proton decoupling field of 80-100 kHz was applied during spectral acquisition. A recycle delay of 5.25 second was used for the Form 1 spectrum. A recycle delay of 45 seconds was used for the Form 2 spectrum. Spectra were collected with a recycle delay of 29 seconds for Form 6, and 5 seconds for Form 8. The number of scans was adjusted to obtain an adequate signal to noise ratio. The $^{19}F$ chemical shift scale was referenced using a $^{19}F$ MAS experiment on an external standard of trifluoroacetic acid and water (50%/50% v/v), setting its resonance to −76.54 ppm.

Peak Picking Method:

Automatic peak picking was performed using Bruker-BioSpin TopSpin version 3.6 software. Generally, a threshold value of 5% relative intensity was used for preliminary peak selection. The output of the automated peak picking was visually checked to ensure validity and adjustments were manually made if necessary. Although specific solid-state NMR peak values are reported herein there does exist a range for these peak values due to differences in instruments, samples, and sample preparation. This is common practice in the art of solid-state NMR because of the variation inherent in peak positions. A typical variability for a $^{13}C$ and $^{19}F$ chemical shift x-axis value is on the order of plus or minus (±) 0.2 ppm for a crystalline solid and plus or minus (±) 0.5 ppm for an amorphous solid. The solid-state NMR peak heights reported herein are relative intensities. Solid-state NMR intensities can vary depending on the actual setup of the experimental parameters and the thermal history of the sample.

General Method 4. Thermogravimetric Analysis (TGA)

Thermogravimetric analysis was conducted using a Discovery TGA (TA instruments) thermogravimetric analyzer. Samples of approximately 10 mg were weighed into aluminum pans and heated from ambient (−20° C.) to 250° C. at 10° C./minute heating rate under nitrogen purge (10 mL/min for both sample chamber and balance).

General Method 5A. Differential Scanning Calorimetry (DSC)

Modulated Differential scanning calorimetry (DSC) measurements were performed with Discovery DSC (TA instruments) equipped with a refrigerated cooling accessory. All the experiments were performed in standard/Tzero aluminum pans. The cell constant was determined using indium and temperature calibration was performed using indium and tin as standards. All the measurements were done under continuous dry nitrogen purge (50 mL/min). Approximately 1-5 mg of solid sample was weighed into a Tzero aluminum pan, sealed non-hermetically and heated from −40° C. to 220° C. at 10° C./min heating rate. The experimental data were analyzed using commercially available software (TA Universal Analysis 2000/Trios software, TA Instruments).

General Method 5B. Differential Scanning Calorimetry (DSC)

DSC measurements were performed with Discovery DSC (TA instruments) equipped with a refrigerated cooling accessory. All the experiments were performed in standard/Tzero aluminum pans. The cell constant was determined using indium and temperature calibration was performed using indium and tin as standards. All the measurements were done under continuous dry nitrogen purge (50 mL/min). Approximately 7 mg of solid sample was weighed into a Tzero aluminum pan, sealed non-hermetically and heated from −40° C. to 165° C. using a modulate temperature amplitude of 1° C., a modulation period of 100 s, and a ramp rate of 2° C./min. The experimental data were analyzed using commercially available software (TA Universal Analysis 2000/Trios software, TA Instruments).

General Method 6. Moisture Sorption (Hygroscopicity)

Water sorption and desorption studies were conducted on an automated vapor sorption analyzer (TA instruments Q5000 SA). The microbalance was calibrated using a 100 mg standard weight. The relative humidity (RH) sensor was calibrated at 5.0, 11.3, 32.8, 52.8, 75.3, and 84.3% RH (25° C.) using saturated salt solutions. Approximately 10-20 mg of the powder sample was placed in the quartz sample holder and dried at 3% RH at 60° C. The attainment of equilibrium was assumed when the weight change of the sample was <0.001 wt % in 5 min or by a maximum equilibration time of 300 minutes. The RH was then progressively increased to 90% in increments of 10% followed by a decrease to a final RH of 10% in 10% RH increments. Again, the attainment of equilibrium was assumed when the weight change of the sample was <0.001 wt % in 5 min or by a maximum equilibration time of 300 minutes. The weight gain at 60% RH is based on the weight after the initial drying step.

Example 1

Preparation of PF-07220060 Monohydrate (Form 2)

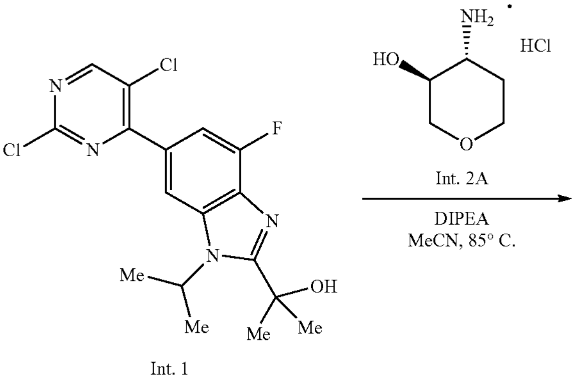

Int. 1

-continued

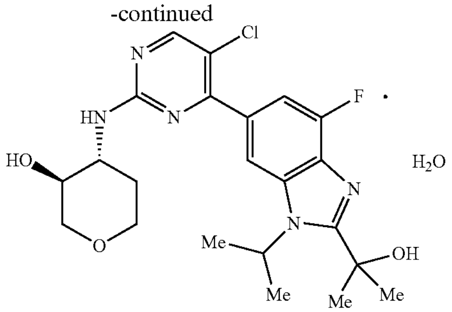

Vial A: MeCN recryst.
PF-07220060 hydrate (Form 1)
Vial B: MeCN/$H_2O$ recryst.
PF-07220060 monohydrate (Form 2)

Two reactions were run in parallel in crimpable vials (labeled Vial A and Vial B). The reactions were run under the same conditions and scale, but the isolation and recrystallization procedures for Vial A and Vial B differed as indicated below.

Each 20 mL crimpable vial was equipped with a stir bar and charged with 2-[6-(2,5-dichloropyrimidin-4-yl)-4-fluoro-1-(propan-2-yl)-1H-benzimidazol-2-yl]propan-2-ol (Int. 1, prepared as described in Example A94 of U.S. Pat. No. 10,233,188) (1.48 g, 3.865 mmol), 3-amino-1,5-anhydro-2,3-dideoxy-D-threo-pentitol hydrochloride (Int. 2A) (0.68 g, 4.44 mmol), and acetonitrile (MeCN) (15 mL). Diisopropylethylamine (DIPEA) (1.745 g, 2.35 mL, 13.5 mmol) was added and the vial was crimped and heated to 85° C. in a heating mantle and stirred for 17 hours.

After cooling slightly, precipitation was observed. LCMS analysis of an aliquot showed and 80:20 mixture of product to starting material. The internal temperature was measured as 76° C. The vial was heated to an internal temperature of 85° C. and the cloudy mixture was heated at that temperature for an additional 21 hours. LCMS analysis of an aliquot showed and 92:8 mixture of product to starting material.

The reaction mixture for each vial was transferred to a round bottom flask and the volume was reduced by one-third, then stirred at room temperature for 1 hour. The mixture was filtered to remove precipitated inorganic solids.

The filtrate was seeded with –1 mg of seed crystals of PF-07220060 hydrate (Form 1) prepared as described in Example A94 of U.S. Pat. No. 10,233,188. After a few minutes, a cloudy suspension formed. The mixture was stirred slowly at room temperature for 2 days. The thick slurry was filtered, and the flask was rinsed with a small volume of acetonitrile to facilitate the transfer, and the solids were rinsed with 10% MeCN/diisopropyl ether (DIPE).

Vial A: PF-07220060 Hydrate (Form 1)

The MeCN/DIPE filtrate was reduced to minimum volume. The residue was partitioned between ethyl acetate (EtOAc)/water and the layers separated. The aqueous layer was extracted once more with EtOAc. The combined organic layers were washed with brine, dried over $MgSO_4$ and filtered. The filtrate was reduced to minimum volume to give 1.75 g of an amber residue.

The residue was dissolved in 18 mL MeCN and stirred at room temperature. After a few minutes, solids started to come out of solution without seeding. The suspension was covered with a kimwipe and allowed to stir overnight. The MeCN suspension was filtered and the solids were rinsed with 10% MeCN/DIPE then dried in the vacuum oven (no heat) overnight to give 834 mg of a white solid. The solid provided a PXRD pattern (FIG. 5) consistent with an authentic sample of PF-07220060 hydrate (Form 1) prepared as described in Example A94 of U.S. Pat. No. 10,233,188.

Vial B: PF-07220060 monohydrate (Form 2)

The MeCN/DIPE filtrate was concentrated to dryness and the solids were dried in a vacuum oven at 55° C. for about 1 hour to give 1.8 g of a slightly sticky, off-white solid. LCMS and $^1H$ NMR analysis showed the solids were contaminated with DIPEA hydrochloride. The solids were resuspended in 18 mL of 10% MeCN/water to give a thick slurry, which was further diluted with an additional 18 mL portion of 10% MeCN/water. The thick mixture was stirred at room temperature for 20 minutes, then filtered and rinsed with 130 mL of 10% MeCN/water.

The solids were dried in a vacuum oven at 55° C. overnight to give 1.75 g of crystalline material. After further characterization, the material was identified as having a new PXRD pattern (FIG. 1) and identified as PF-07220060 monohydrate (Form 2). Elemental analysis passed with 1.0 equivalent of water. Analysis calculated for $C_{22}H_{27}N_5O_3FCl$. 1.0 $H_2O$: C: 54.82; H: 6.07; N: 14.53; Cl: 7.36; Found: C: 54.73, 54.81; H: 6.08, 6.12; N: 14.42, 14.45; Cl; 7.19.

Example 2

Alternative Preparation of PF-07220060 Monohydrate (Form 2)

Step 1: 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060)

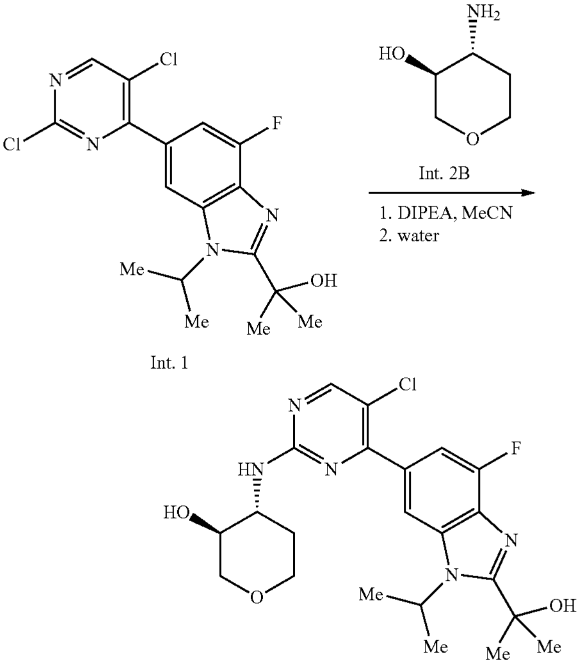

Int. 1

PF-07220060

A 200 L reactor purged with nitrogen was charged with acetonitrile (45 L, 5 vol). The reactor was set to a jacket temperature (Tj) of 25° C.±5° C. and 2-[6-(2,5-dichloropyrimidin-4-yl)-4-fluoro-1-(propan-2-yl)-1H-benzimidazol-2-yl]propan-2-ol (Int. 1, 9 kg, 23.34 mol) and 3-amino-1,5-anhydro-2,3-dideoxy-D-threo-pentitol (Int. 2B, 3.867 kg, 32.68 mol, 1.4 equiv) were charged. The mixture was stirred at medium speed for a minimum of 10 min. before charging DIPEA (8.132 L, 46.68 mol, 2 equiv). The reactor was set to a Tj of 80° C.±5° C. and the reaction was heated for 36 h under nitrogen atmosphere. A second charge of DIPEA (2 L, 11.67 mol, 0.5 equiv) was required to push to 97% reaction completion after heating for another 6 h at a Tj of 80° C.±5° C. Process water (45.00 L, 5 vol) was charged over 20 min while maintaining a temperature of 75° C.±10° C. and the reaction was cooled to 25° C.±5° C. over 60 min, and held at this temperature for 18 h.

The solvent was reduced under mild vacuum to approximately 35 volumes and the resulting solution was seeded with crystalline material generated outside the reactor by cooling/scratching a 30 mL aliquot. After crystallization occurred, the resulting mixture was granulated at room temperature over 18 h.

The crude product PF-07220060 was collected by filtration through a Nutsche filter and the cake was rinsed with MeCN/water (45 L, 10 vol, 1:1 mixture), and pulled dry under nitrogen to give the crude 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060) as a light brown solid (10 kg, 94.38% yield, 97% purity by UPLC).

Step 1R: 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol monohydrate (PF-07220060) (Form 2)

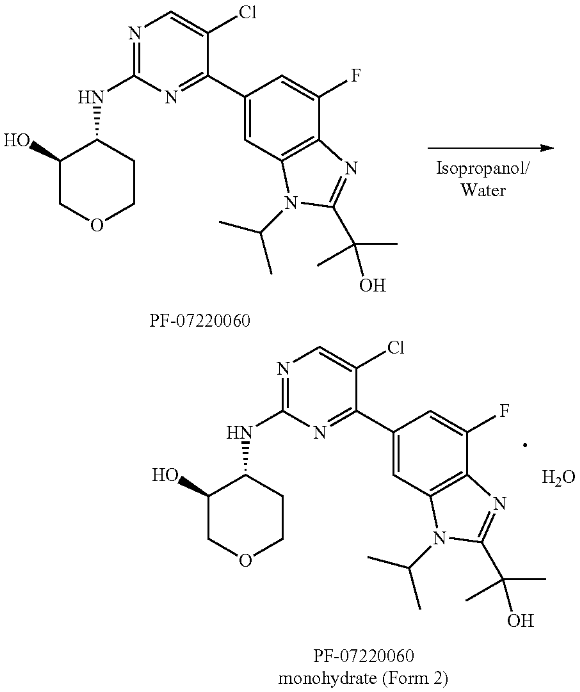

PF-07220060

PF-07220060 monohydrate (Form 2)

In a 200 L reactor, isopropanol (100 L, 10 Vol) and the crude 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060, 10 kg, 21.56 mol) were charged. The reactor was set to a Tj of 40° C.±15° C. and the mixture was stirred under nitrogen until complete dissolution was achieved (60 min). The solution was cooled to 25° C.±5° C. and it was transferred into a holding drum.

In a 200 L reactor, particulate filter process water (135 L, 13.5 volumes) was charged. The reactor was set to a Tj of 40° C.±5° C. and the isopropanol solution containing the product was added to the reactor through a polypropylene particulate filter while distilling under vacuum. The transfer rate and reactor pressure were adjusted as needed to distill isopropanol while maintaining a constant volume of about 135 L in the 200 L vessel and an approximate ratio of 85/15 water to isopropanol. Once the addition was completed, the product was granulated for 48 h and the particle size reduced using high shear wet milling.

The product was filtered through a Nutsche filter and the cake was washed with 27 L of process water and pulled dry under vacuum. The product was transferred to oven trays and further dried under vacuum at 30° C.±10° C. over 4 h to give 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060) monohydrate (Form 2) as a white solid (9.2 kg, 81% yield, 98.6% purity by UPLC).

Example 3

Characterization of PF-07220060 Monohydrate (Form 2)

PF-07220060 monohydrate (Form 2) prepared according to Example 2 was characterized as follows:

PXRD Data

FIG. 1 shows PXRD data for PF-07220060 monohydrate (Form 2), collected according to General Method 1A. A list of PXRD peaks at diffraction angles 2-Theta (° 2θ)±0.2°2θ and their relative intensities is provided in Table 1.

TABLE 1

PXRD Peak list for PF-07220060 monohydrate (Form 2) (2-Theta °)

| Angle (2-theta °) ± 0.2 °2θ | Relative Intensity (%) |
|---|---|
| 9.6 | 66.3 |
| 11.8 | 15.7 |
| 12.4 | 10 |
| 13.1 | 14.4 |
| 13.5 | 6.6 |
| 14.7 | 54.7 |
| 16.4 | 25.2 |
| 16.9 | 15.2 |
| 17.2 | 10.7 |
| 19.3 | 28.5 |
| 19.7 | 8.2 |
| 20.2 | 8.3 |
| 20.4 | 18.1 |
| 21.0 | 100.0 |
| 22.0 | 25.8 |
| 22.2 | 40.3 |
| 23.3 | 5.6 |
| 23.7 | 14.8 |
| 26.4 | 48.8 |
| 27.1 | 13.3 |
| 27.7 | 11.7 |
| 28.0 | 11.0 |
| 28.7 | 7.5 |

TABLE 1-continued

| PXRD Peak list for PF-07220060 monohydrate (Form 2) (2-Theta °) | |
|---|---|
| Angle (2-theta °) ± 0.2 °2θ | Relative Intensity (%) |
| 29.5 | 14.6 |
| 30.1 | 31.1 |
| 30.8 | 7.9 |
| 31.8 | 12.9 |
| 33.3 | 20.8 |
| 33.9 | 9.3 |
| 35.2 | 9.1 |
| 35.7 | 6.9 |
| 36.1 | 6.4 |
| 36.4 | 5.8 |
| 39.8 | 6.3 |

FT-Raman Data

Figure 2:
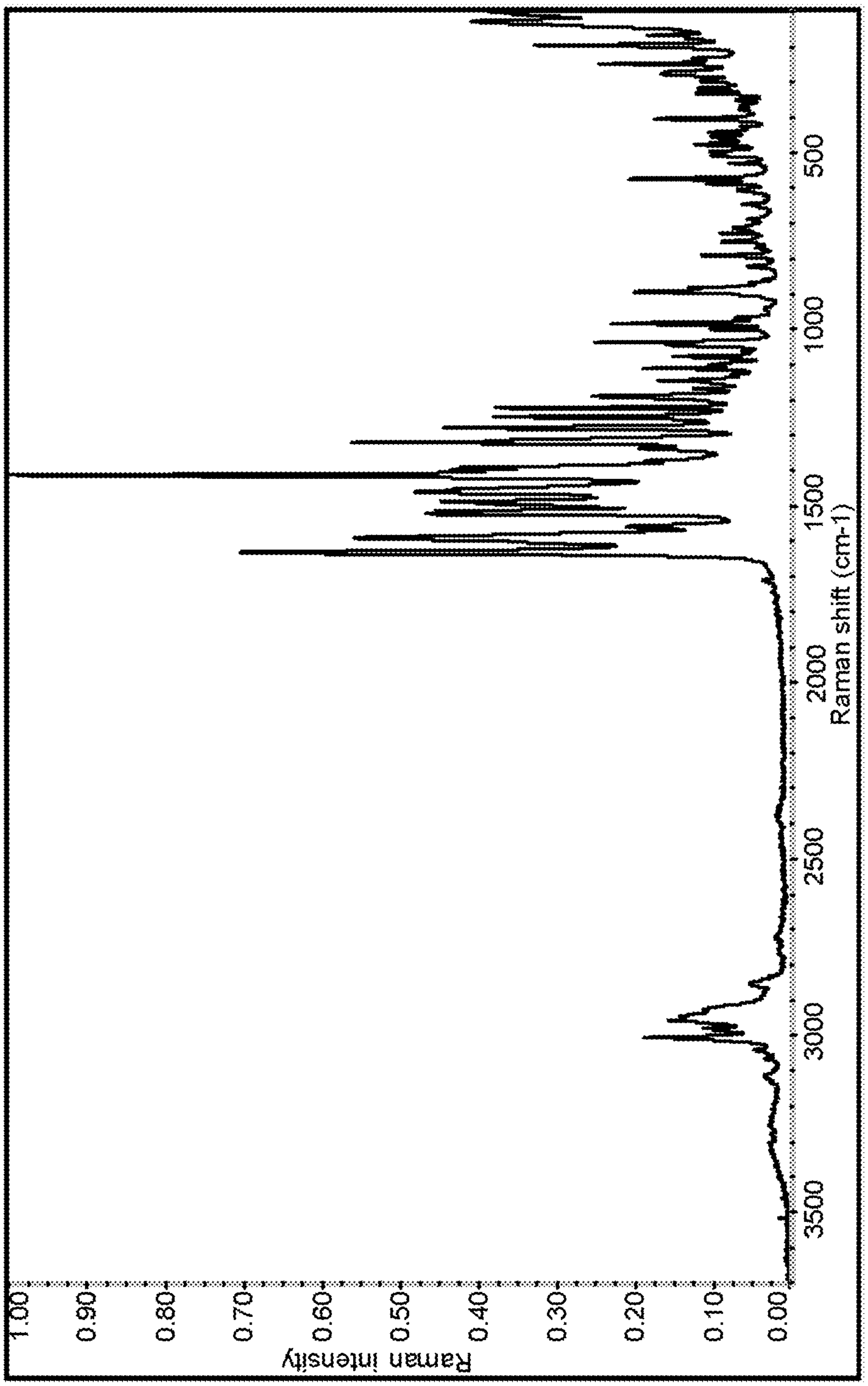
FIG. 2. FT-Raman spectrum of crystalline PF-07220060 monohydrate (Form 2).

FIG. 2 shows the FT-Raman spectrum of PF-07220060 monohydrate (Form 2), collected according to General Method 2. A full list of FT-Raman peaks ($cm^{-1}$) and qualitative intensities is provided in Table 2 in $cm^{-1}\pm 2$ $cm^{-1}$ Normalized peak intensities are indicated as follows: w=weak; m=medium; s=strong.

TABLE 2

| FT Raman Peak list for PF-07220060 monohydrate (Form 2) ($cm^{-1}$) | | |
|---|---|---|
| Peak position $cm^{-1}$ ± 2 $cm^{-1}$ | Normalized intensity | Classification |
| 99 | 0.39 | m |
| 124 | 0.41 | m |
| 163 | 0.18 | w |
| 191 | 0.33 | m |
| 229 | 0.12 | w |
| 245 | 0.24 | w |
| 273 | 0.17 | w |
| 293 | 0.11 | w |
| 313 | 0.12 | w |
| 328 | 0.12 | w |
| 347 | 0.07 | w |
| 364 | 0.06 | w |
| 372 | 0.06 | w |
| 400 | 0.17 | w |
| 421 | 0.06 | w |
| 439 | 0.10 | w |
| 449 | 0.10 | w |
| 460 | 0.09 | w |
| 471 | 0.12 | w |
| 491 | 0.10 | w |
| 500 | 0.10 | w |
| 525 | 0.08 | w |
| 570 | 0.20 | w |
| 584 | 0.11 | w |
| 601 | 0.07 | w |
| 641 | 0.06 | w |
| 710 | 0.07 | w |
| 716 | 0.06 | w |
| 724 | 0.09 | w |
| 748 | 0.09 | w |
| 786 | 0.11 | w |
| 881 | 0.13 | w |
| 890 | 0.20 | w |
| 963 | 0.07 | w |
| 980 | 0.23 | w |
| 996 | 0.10 | w |
| 1033 | 0.25 | w |
| 1042 | 0.15 | w |
| 1060 | 0.06 | w |
| 1073 | 0.15 | w |
| 1097 | 0.10 | w |
| 1107 | 0.19 | w |
| 1125 | 0.08 | w |

TABLE 2-continued

| FT Raman Peak list for PF-07220060 monohydrate (Form 2) ($cm^{-1}$) | | |
|---|---|---|
| Peak position $cm^{-1}$ ± 2 $cm^{-1}$ | Normalized intensity | Classification |
| 1140 | 0.17 | w |
| 1165 | 0.12 | w |
| 1186 | 0.25 | w |
| 1218 | 0.37 | m |
| 1244 | 0.38 | m |
| 1274 | 0.44 | m |
| 1317 | 0.56 | m |
| 1332 | 0.19 | w |
| 1368 | 0.19 | w |
| 1387 | 0.42 | m |
| 1395 | 0.44 | m |
| 1408 | 1.00 | s |
| 1457 | 0.48 | m |
| 1484 | 0.45 | m |
| 1510 | 0.45 | m |
| 1517 | 0.47 | m |
| 1555 | 0.21 | w |
| 1587 | 0.56 | m |
| 1627 | 0.70 | m |
| 2954 | 0.15 | w |
| 2975 | 0.11 | w |
| 2983 | 0.10 | w |
| 3001 | 0.19 | w |

ssNMR data

Figure 3:
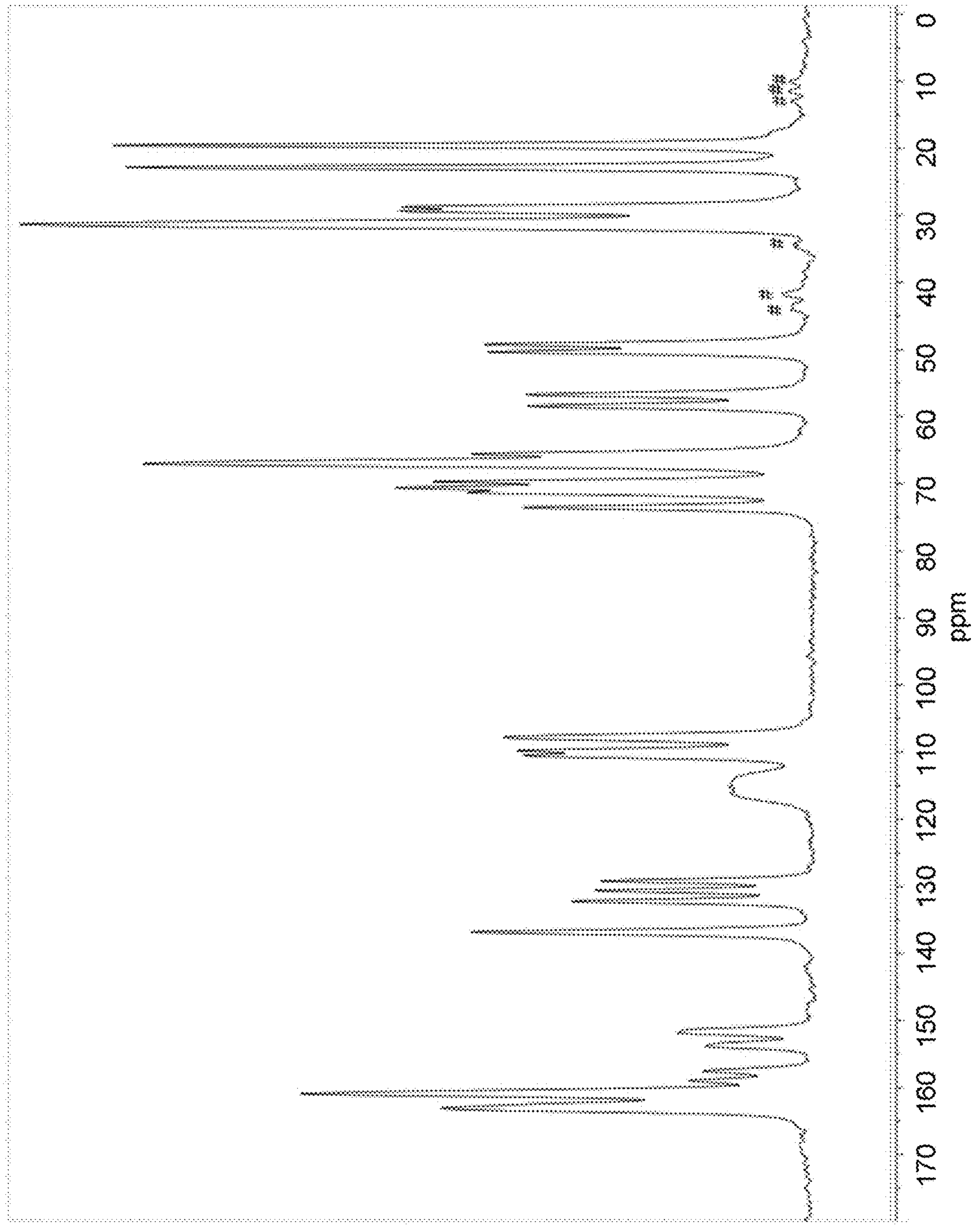
FIG. 3. Carbon CPMAS spectrum of crystalline PF-07220060 monohydrate (Form 2) (# indicates spinning sidebands).

FIG. 3 shows the carbon CPMAS spectrum of PF-07220060 monohydrate (Form 2), which was collected according to General Method 3. Chemical shifts are expressed in parts per million (ppm) and are referenced to external sample of solid phase adamantane at 29.5 ppm. A list of ssNMR $^{13}C$ chemical shifts (ppm) for Form 2 is provided in Table 3 in ppm±0.2 ppm.

TABLE 3

| ssNMR $^{13}C$ Chemical Shifts for PF-07220060 monohydrate (Form 2) (ppm) | |
|---|---|
| $^{13}C$ Chemical Shifts ppm ± 0.2 ppm | Relative Intensity (%) |
| 19.6 | 88 |
| 22.8 | 86 |
| 28.7 | 51 |
| 29.4 | 52 |
| 31.3 | 100 |
| 49.2 | 41 |
| 50.3 | 41 |
| 56.7 | 36 |
| 58.4 | 36 |
| 65.6 | 43 |
| 67.0 | 85 |
| 69.7 | 48 |
| 70.6 | 53 |
| 71.3 | 44 |
| 73.5 | 37 |
| 107.8 | 40 |
| 109.8 | 38 |
| 110.5 | 37 |
| 115.1 | 11 |
| 129.1 | 27 |
| 130.6 | 28 |
| 132.2 | 31 |
| 136.8 | 44 |
| 151.4 | 17 |
| 151.8 | 18 |
| 153.4 | 13 |

TABLE 3-continued

| ssNMR $^{13}C$ Chemical Shifts for PF-07220060 monohydrate (Form 2) (ppm) | |
|---|---|
| $^{13}C$ Chemical Shifts ppm ± 0.2 ppm | Relative Intensity (%) |
| 153.8 | 14 |
| 157.5 | 14 |
| 158.9 | 16 |
| 160.9 | 66 |
| 163.0 | 48 |

FIG. 4 shows the $^{19}F$ ssNMR spectrum of PF-07220060 monohydrate (Form 2), which was collected according to General Method 3. Chemical shifts are expressed in parts per million (ppm) and are referenced to external standard of trifluoroacetic acid and water (50/50 volume/volume), setting its resonance to −76.54 ppm (as determined from neat TMS).

TABLE 4

| $^{19}F$ solid state NMR peak list for PF-07220060 monohydrate (Form 2) (ppm). | |
|---|---|
| $^{19}F$ Chemical Shifts ppm ± 0.2 ppm | Relative Intensity (%) |
| −126.1 | 100 |
| −125.6 | 95 |

Example 4

Comparative Example: Preparation of PF-07220060 Hydrate (Form 1)

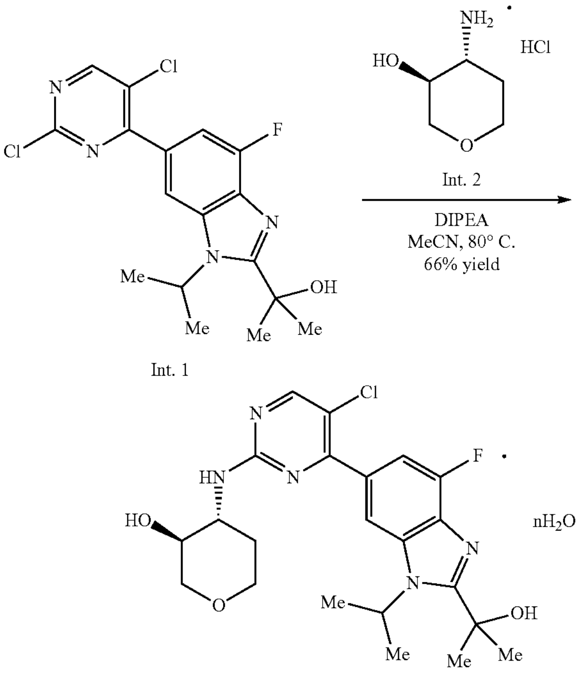

Int. 1

Int. 2

PF-07220060 hydrate (Form 1)

PF-07220060 hydrate (Form 1) was prepared as a white crystalline solid according to the procedure described in Example A94 of U.S. Pat. No. 10,233,188. The crystalline solid was determined to be a hydrate having undefined stoichiometry and identified as PF-07220060 hydrate (Form 1).

Example 5

Comparative Example: Alternate Preparation of PF-07220060 Hydrate (Form 1)

Example 5A: Crystalline PF-07220060 monohydrate (Form 2) (348 mg) prepared as described in Example 2 and acetonitrile (3.00 mL) were stirred at room temperature. After stirring approximately 24 hours, a small aliquot (~0.1 mL) was removed from the mixture for analysis with PXRD. The remaining material was stirred for another day. After stirring for a total of two days, the white solid was collected with vacuum filtration and washed with acetonitrile (2×0.500 mL). 282 mg, 81%. The solid was confirmed by PXRD to have converted to PF-07220060 hydrate (Form 1).

Example 5B: PF-07220060 monohydrate (Form 2) (1.01529 g) prepared as described in Example 2 was combined with acetonitrile (10.0 mL). After stirring for 3 days, the solid was collected with vacuum filtration and dried on the filter frit. The crystalline solid was determined to be PF-07220060 hydrate (Form 1).

Example 6

Characterization of PF-07220060 Hydrate (Form 1)

PF-07220060 hydrate (Form 1) prepared as described in Example 5B was characterized as follows:

PXRD Data

Figure 5:
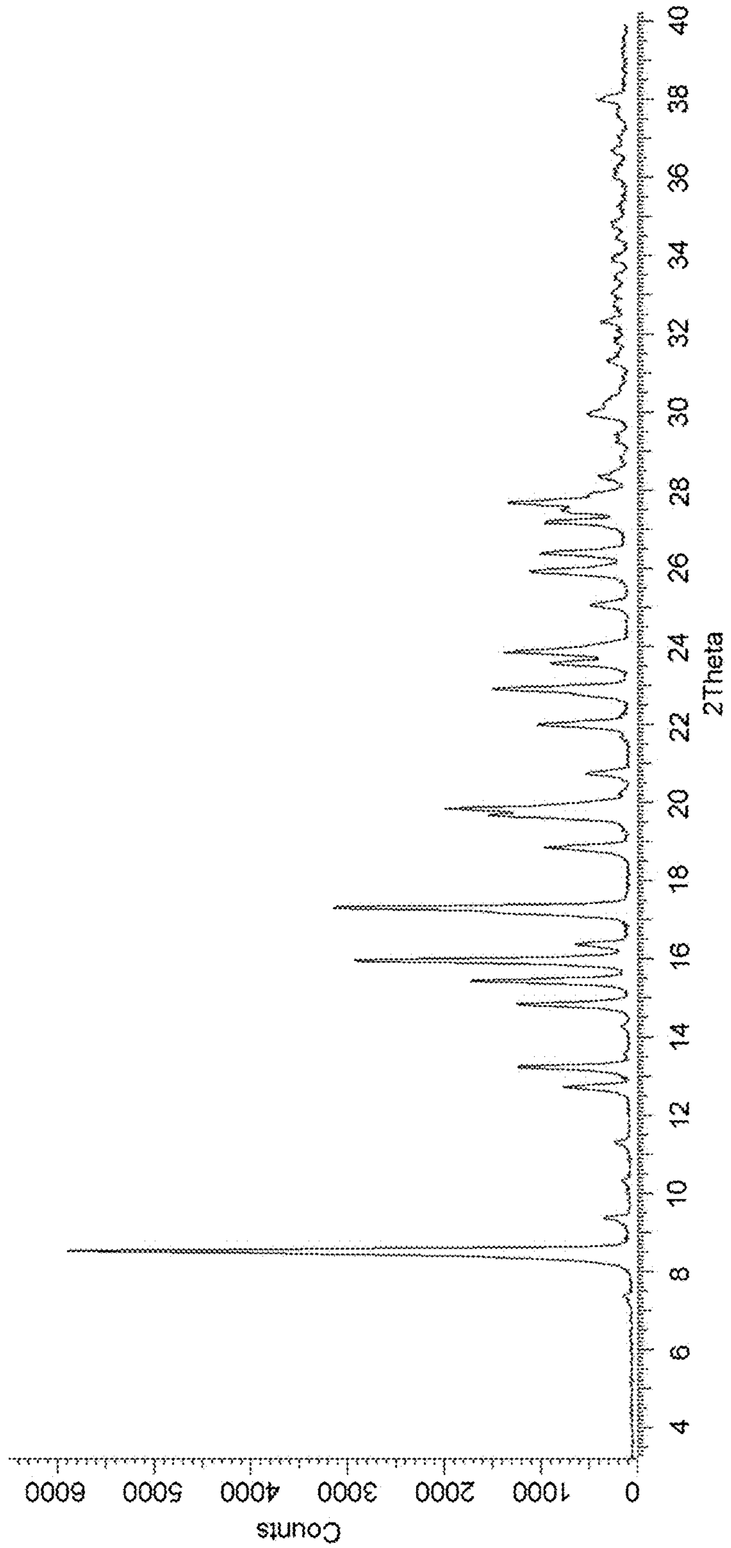
FIG. 5. PXRD pattern of crystalline PF-07220060 hydrate (Form 1).

FIG. 5 shows PXRD data for PF-07220060 hydrate (Form 1), collected according to General Method 1B.

ssNMR Data

Figure 6:
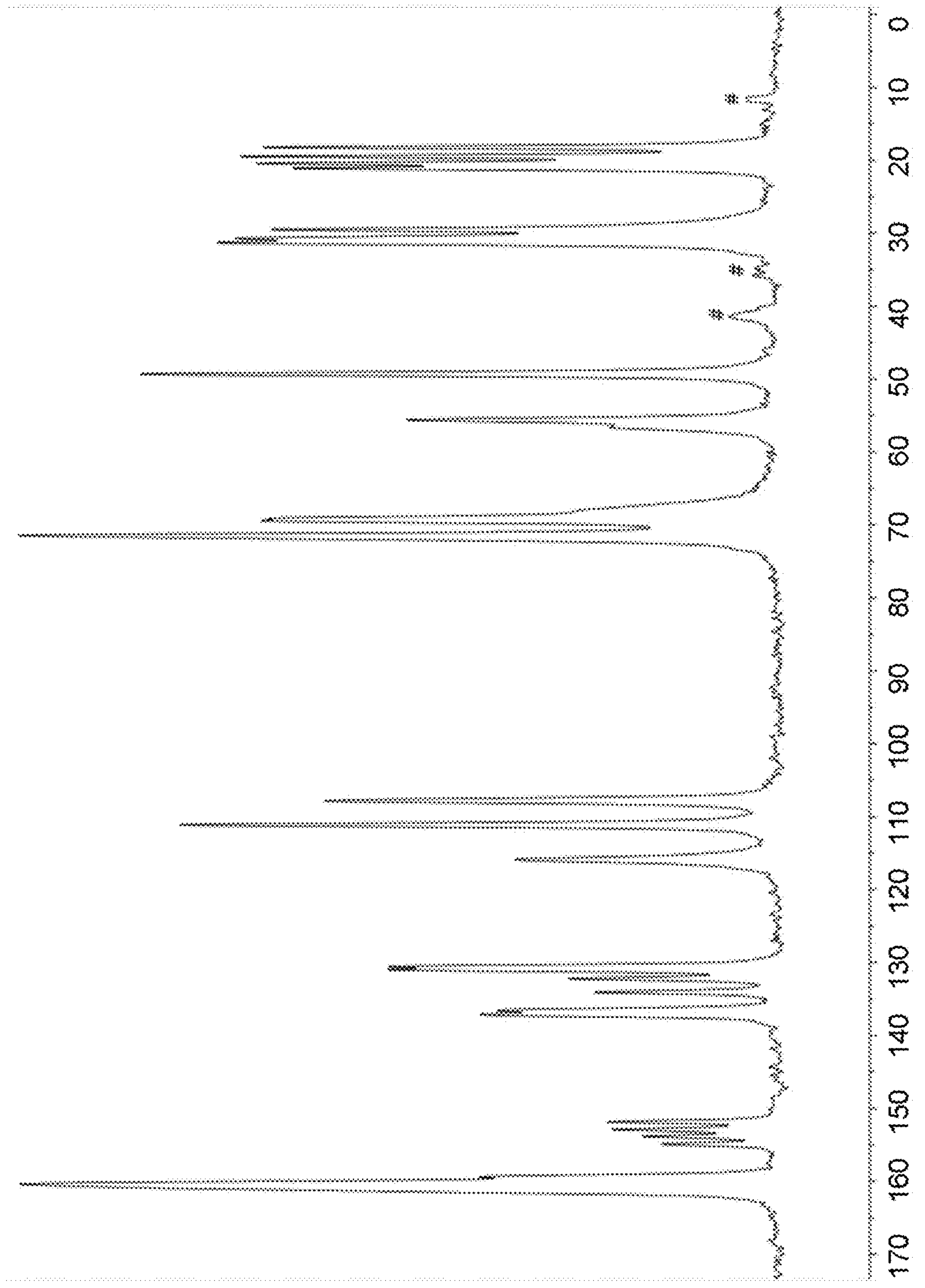
FIG. 6. Carbon CPMAS spectrum of crystalline PF-07220060 hydrate (Form 1) (# indicates spinning sidebands).

FIG. 6 shows the carbon CPMAS spectrum of PF-07220060 hydrate (Form 1), which was collected according to General Method 3. Chemical shifts are expressed in parts per million (ppm) and are referenced to external sample of solid phase adamantane at 29.5 ppm. A list of ssNMR $^{13}C$ chemical shifts (ppm) for Form 1 is provided in Table 5 in ppm±0.2 ppm.

TABLE 5

| ssNMR $^{13}C$ Chemical Shifts for PF-07220060 hydrate (Form 1) (ppm) | |
|---|---|
| $^{13}C$ Chemical Shifts ppm ± 0.2 ppm | Relative Intensity (%) |
| 18.2 | 67 |
| 19.4 | 70 |
| 20.4 | 68 |
| 21.1 | 63 |
| 29.5 | 66 |
| 30.7 | 71 |
| 31.3 | 73 |
| 49.3 | 84 |
| 55.6 | 48 |

TABLE 5-continued

| ssNMR $^{13}C$ Chemical Shifts for PF-07220060 hydrate (Form 1) (ppm) | |
|---|---|
| $^{13}C$ Chemical Shifts ppm ± 0.2 ppm | Relative Intensity (%) |
| 56.6 | 21 |
| 68.1 | 27 |
| 69.1 | 67 |
| 69.4 | 68 |
| 71.4 | 100 |
| 107.8 | 60 |
| 111.1 | 79 |
| 115.9 | 35 |
| 130.5 | 52 |
| 131.0 | 51 |
| 132.2 | 27 |
| 134.1 | 24 |
| 136.6 | 37 |
| 137.1 | 39 |
| 151.8 | 23 |
| 152.9 | 22 |
| 153.8 | 18 |
| 154.9 | 15 |
| 159.4 | 39 |
| 160.4 | 100 |

Figure 7:
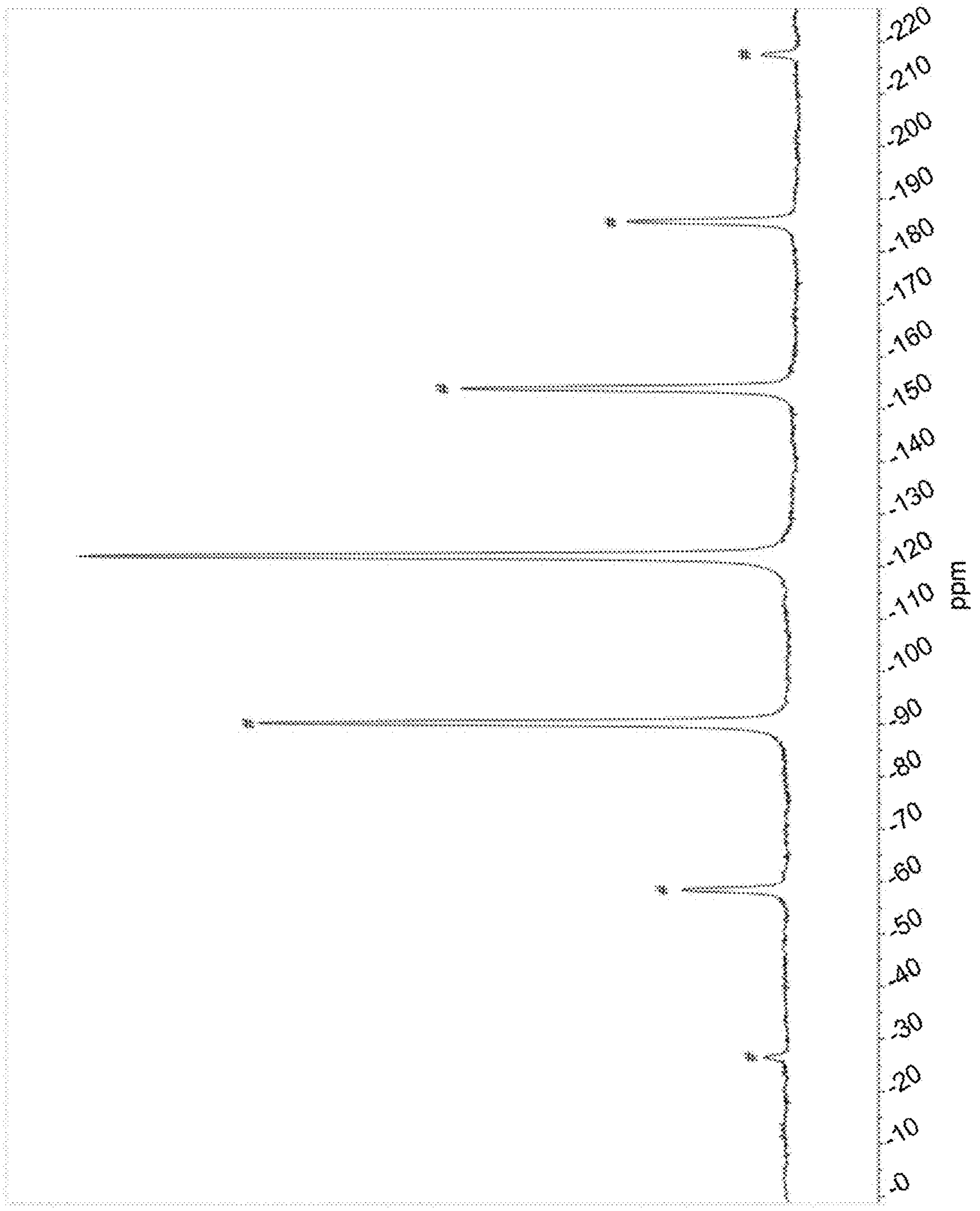
FIG. 7. Fluorine MAS spectrum of crystalline PF-07220060 hydrate (Form 1) (# indicates spinning sidebands).

FIG. 7 shows the $^{19}F$ ssNMR spectrum of PF-07220060 hydrate (Form 1), which was collected according to General Method 3. Chemical shifts are expressed in parts per million (ppm) and are referenced to external standard of trifluoroacetic acid and water (50/50 volume/volume), setting its resonance to −76.54 ppm (as determined from neat TMS). A list of ssNMR $^{19}F$ chemical shifts (ppm) for Form 1 is provided in Table 6 in ppm±0.2 ppm.

TABLE 6

| $^{19}F$ solid state NMR peak list for PF-07220060 hydrate (Form 1) (ppm). | |
|---|---|
| $^{19}F$ Chemical Shifts ppm ± 0.2 ppm | Relative Intensity (%) |
| −122.0 | 100 |

Example 7

Conversion of PF-07220060 Hydrate (Form 1) to PF-07220060 Monohydrate (Form 2)

Crystalline PF-07220060 hydrate (Form 1) (25 mg) prepared as described in Example 1, Vial A was suspended in 10% MeCN/water (0.5 mL) and slurried at room temperature for ~30 minutes. An aliquot of the suspension was confirmed by PXRD to have converted to PF-07220060 monohydrate (Form 2).

Example 8

Preparation of Amorphous PF-07220060 (Form 8)

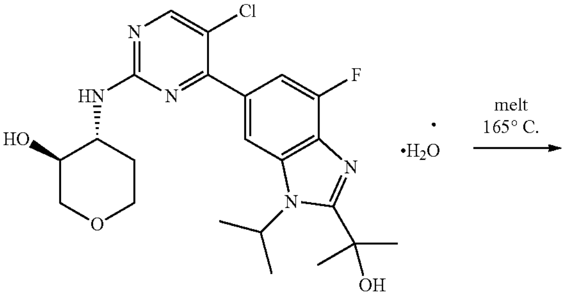

PF-07220060 monohydrate (Form 2)

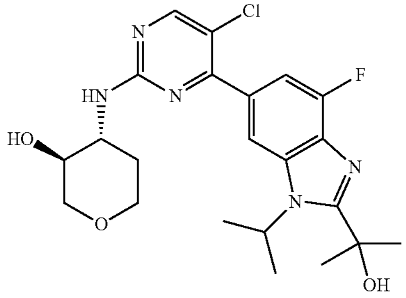

PF-07220060 amorphous

PF-07220060 monohydrate (Form 2) (331.7 mg), prepared as described in Example 2, was melted in a small aluminum pan at approximately 165° C. The resulting pale-yellow liquid was placed in ice water and cooled rapidly. The liquid became a pale-yellow, transparent solid. The solid was transferred to a vial and crushed with a spatula into a pale-yellow powder, which was determined by PXRD to be amorphous PF-07220060 (Form 8) (294.2 mg, 89%).

Example 9

Alternative Preparation of Amorphous PF-07220060 (Form 8)

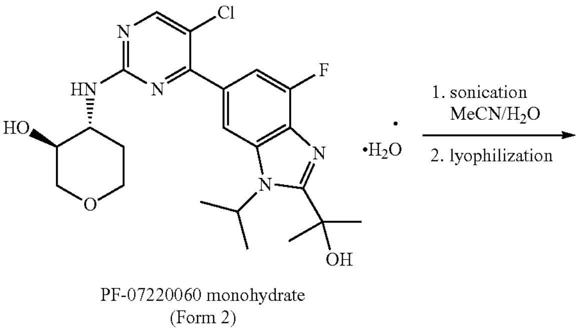

PF-07220060 monohydrate (Form 2)

-continued

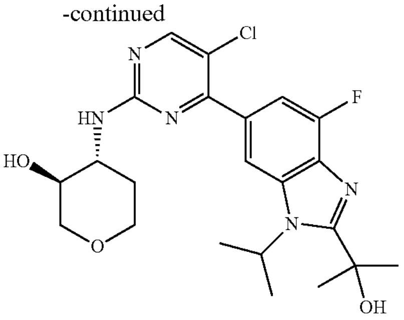

PF-07220060 amorphous (Form 8)

PF-07220060 monohydrate (Form 2) (~2 g), prepared as described in Example 2, and acetonitrile (100 mL) was combined and sonicated for 15 minutes. The sample was then placed in a 50° C. water batch for 15 minutes until the solid fully dissolved. Water (5.0 mL) was added before the sample was sonicated for 5 more minutes. The resulting solution was filtered through a 0.20 mm PTFE filter. The filtrate was frozen with a dry ice/acetone bath and placed onto a Labconco FreezeZone −105° C. freeze dryer. The sample was kept on the freeze dryer until all solvent was removed.

Example 10

Characterization of Amorphous PF-07220060 (Form 8)

Amorphous PF-07220060 (Form 8), prepared as described in Example 9, was characterized as follows:

PXRD Data

Figure 8:
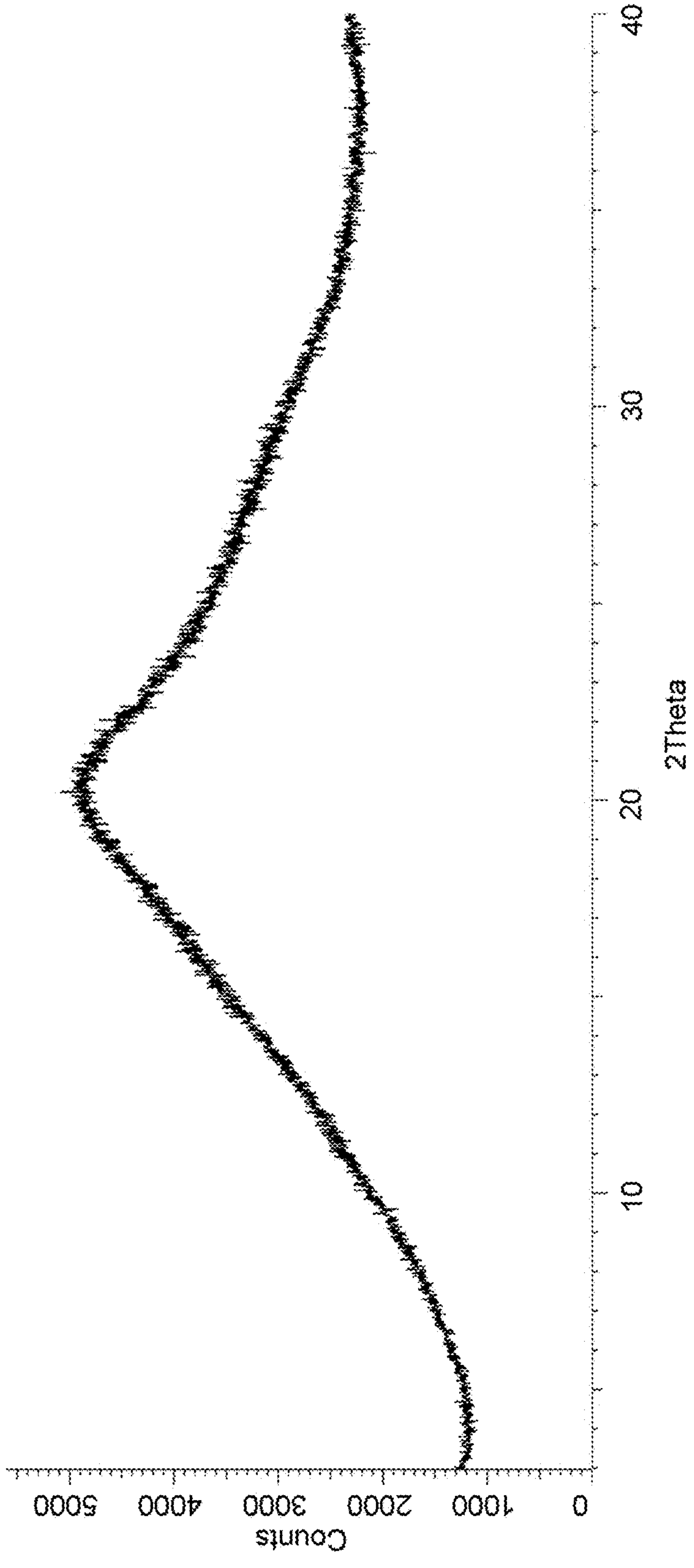
FIG. 8. PXRD pattern of amorphous PF-07220060.

FIG. 8 shows PXRD data for amorphous PF-07220060 (Form 8), collected according to General Method 1A.

Modulated Differential Scanning Calorimetry (DSC)

Figure 9:
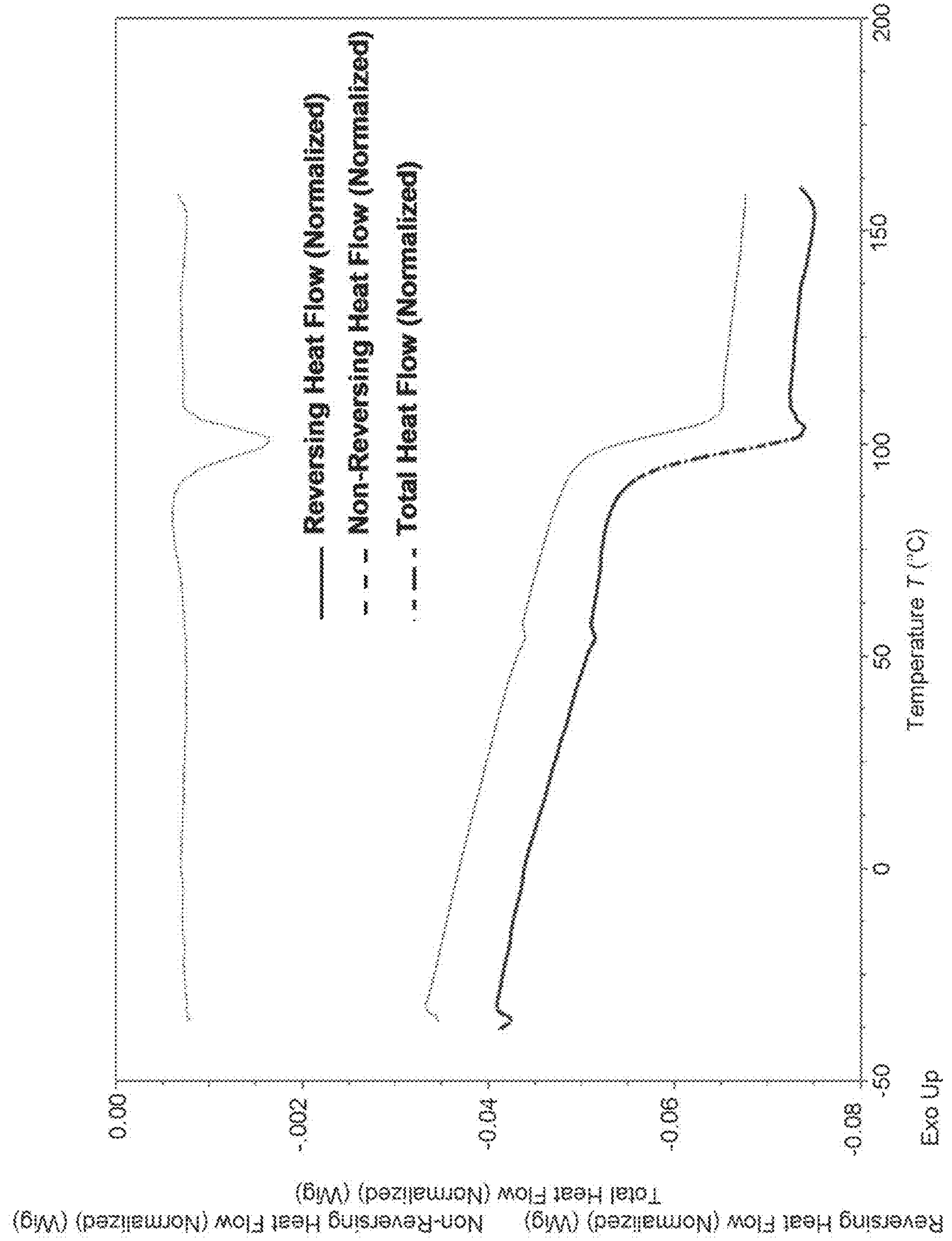
FIG. 9. Modulated DSC scan of amorphous PF-07220060.

FIG. 9 shows a modulated DSC scan of amorphous PF-07220060 (Form 8) collected according to General Method 5B, showing a glass transition temperature (Tg) of 102° C.±5° C.

FT-Raman Data

Figure 10:
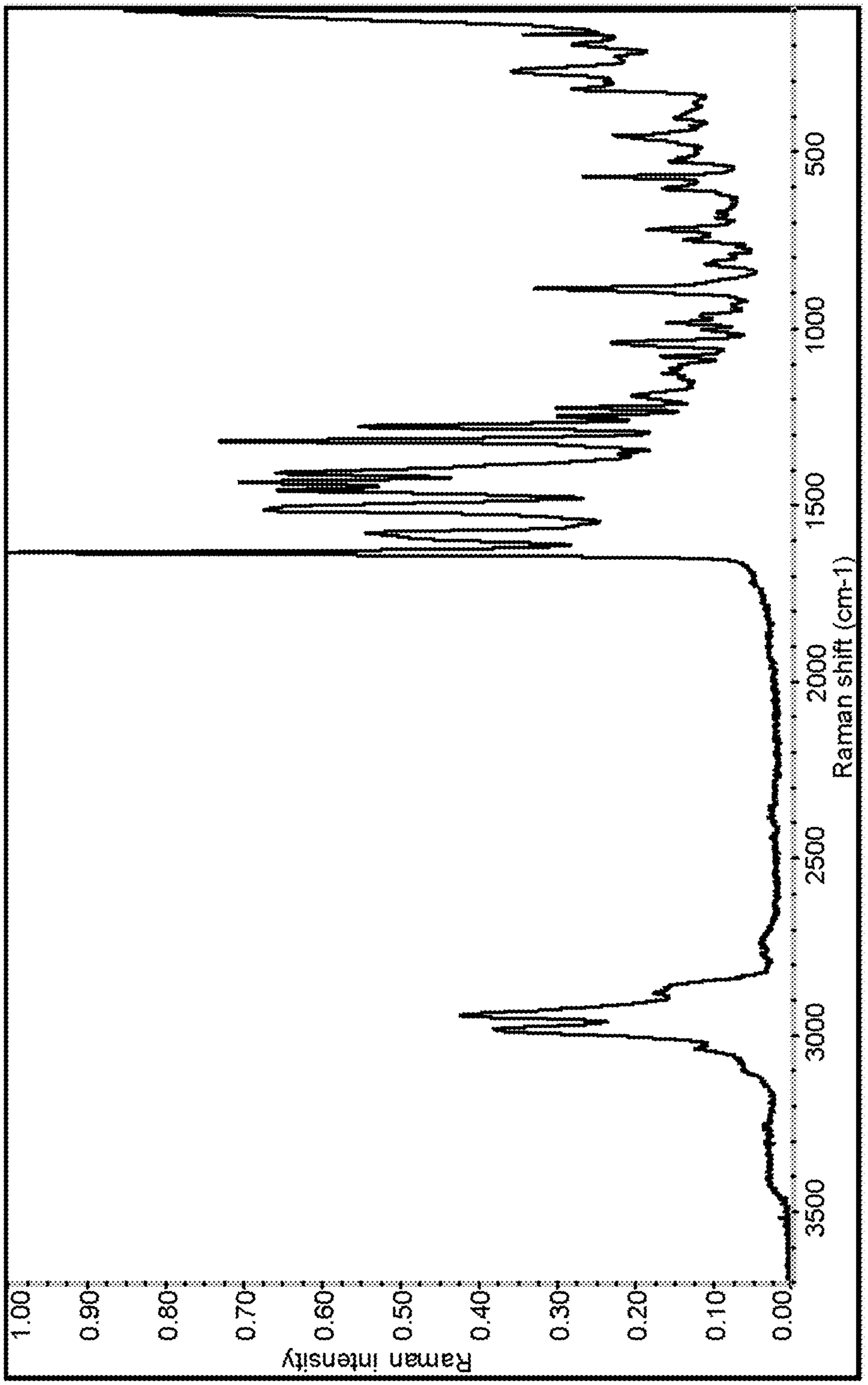
FIG. 10. FT-Raman spectrum of amorphous PF-07220060 (Form 8).

FIG. 10 shows the FT-Raman spectrum of amorphous PF-07220060 (Form 8), collected according to General Method 2. A full list of FT-Raman peaks ($cm^{-1}$) and qualitative intensities is provided in Table 7 in $cm^{-1}$±2 $cm^{-1}$. Normalized peak intensities are indicated as follows: w=weak; m=medium; s=strong.

TABLE 7

FT Raman peak list for amorphous PF-07220060 (Form 8) ($cm^{-1}$)

| Peak position $cm^{-1}$ ± 2 $cm^{-1}$ | Normalized intensity | Classification |
|---|---|---|
| 225 | 0.22 | w |
| 269 | 0.36 | m |
| 318 | 0.28 | w |
| 354 | 0.12 | w |
| 401 | 0.15 | w |
| 421 | 0.13 | w |
| 449 | 0.23 | w |
| 522 | 0.16 | w |
| 566 | 0.27 | w |
| 599 | 0.16 | w |
| 666 | 0.09 | w |
| 682 | 0.10 | w |
| 716 | 0.18 | w |
| 746 | 0.14 | w |
| 767 | 0.07 | w |
| 813 | 0.11 | w |
| 882 | 0.33 | m |
| 933 | 0.07 | w |
| 957 | 0.12 | w |
| 979 | 0.16 | w |
| 998 | 0.11 | w |
| 1035 | 0.23 | w |
| 1075 | 0.17 | w |
| 1107 | 0.15 | w |
| 1122 | 0.16 | w |
| 1186 | 0.20 | w |
| 1220 | 0.30 | m |
| 1243 | 0.30 | m |
| 1273 | 0.55 | m |
| 1314 | 0.73 | m |
| 1351 | 0.22 | w |
| 1405 | 0.66 | m |
| 1430 | 0.70 | m |
| 1453 | 0.66 | m |
| 1509 | 0.67 | m |
| 1574 | 0.54 | m |
| 1630 | 1.00 | s |
| 2829 | 0.07 | w |
| 2877 | 0.18 | w |
| 2940 | 0.42 | m |
| 2979 | 0.38 | m |
| 3034 | 0.12 | w |

ssNMR Data

Figure 11:
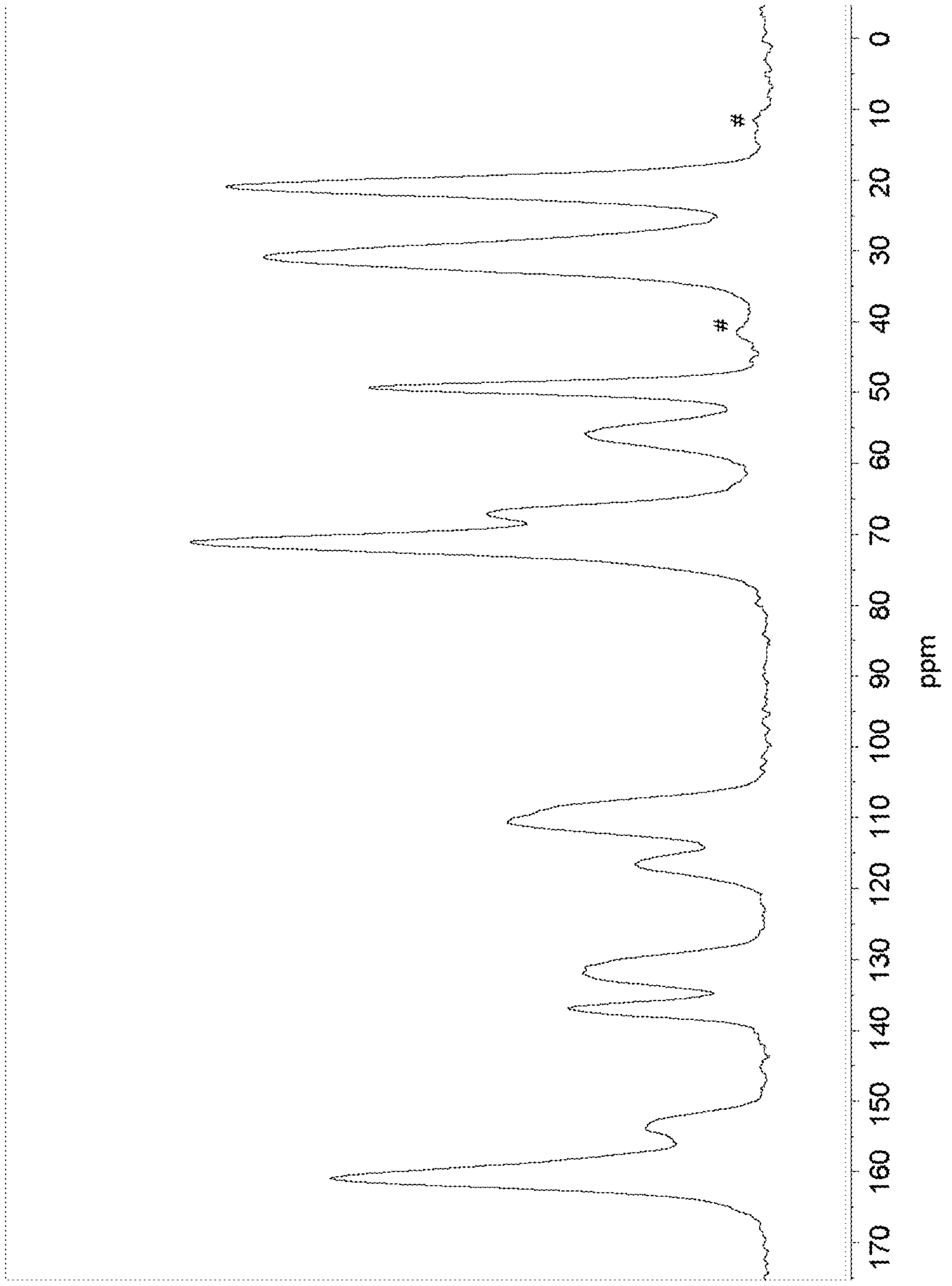
FIG. 11. Carbon CPMAS spectrum of amorphous PF-07220060 (Form 8) (# indicates spinning sidebands).

FIG. 11 shows the carbon CPMAS spectrum of amorphous PF-07220060 (Form 8), which was collected according to General Method 3. Chemical shifts are expressed in parts per million (ppm) and are referenced to external sample of solid phase adamantane at 29.5 ppm. A list of ssNMR $^{13}C$ chemical shifts (ppm) for Form 8 is provided in Table 8 in ppm±0.2 ppm.

TABLE 8 ssNMR $^{13}C$ Chemical Shifts for amorphous PF-07220060 (Form 8) (ppm)

| $^{13}C$ Chemical Shifts ppm ± 0.2 ppm | Relative Intensity (%) |
|---|---|
| 160.9 | 76 |
| 153.9 | 21 |
| 136.9 | 34 |
| 132.0 | 32 |
| 131.1 | 31 |
| 116.6 | 23 |
| 110.6 | 45 |
| 71.2 | 100 |
| 67.2 | 49 |
| 55.8 | 32 |
| 49.3 | 69 |
| 30.9 | 87 |
| 20.9 | 94 |

FIG. 12 shows the $^{19}F$ ssNMR spectrum of amorphous PF-07220060 (Form 8), which was collected according to General Method 3. Chemical shifts are expressed in parts per million (ppm) and are referenced to external standard of trifluoroacetic acid and water (50/50 volume/volume), setting its resonance to −76.54 ppm (as determined from neat TMS).

TABLE 9

| $^{19}F$ solid state NMR peak list for amorphous PF-07220060 (Form 8) (ppm). | |
|---|---|
| $^{19}F$ Chemical Shifts ppm ± 0.2 ppm | Relative Intensity (%) |
| −127.5 | 100 |

Example 11

Preparation of Anhydrous Crystalline PF-07220060 (Form 6)

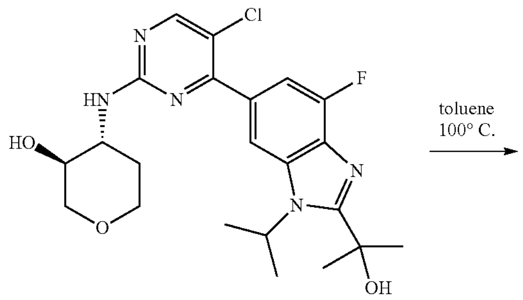

PF-07220060
amorphous (Form 8)

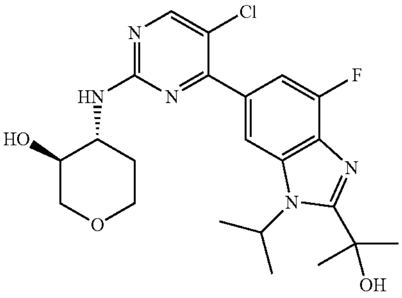

anhydrous PF-07220060
(Form 6)

Amorphous PF-07220060 (Form 8) (991.94 mg), prepared as described in Example 9, was added to a 20 mL vial with a stir bar. Toluene (7.50 mL) was added and the mixture warmed to 100° C. After stirring for 1 hour at 100° C., the solid was collected (while still hot) with vacuum filtration and dried under vacuum at 50° C. to provide anhydrous crystalline PF-07220060 (Form 6). 614 mg, 62%.

Example 12

Characterization of Anhydrous Crystalline PF-07220060 (Form 6) Anhydrous crystalline PF-07220060 (Form 6), prepared as described in Example 11, was characterized as follows:

PXRD Data

Figure 13:
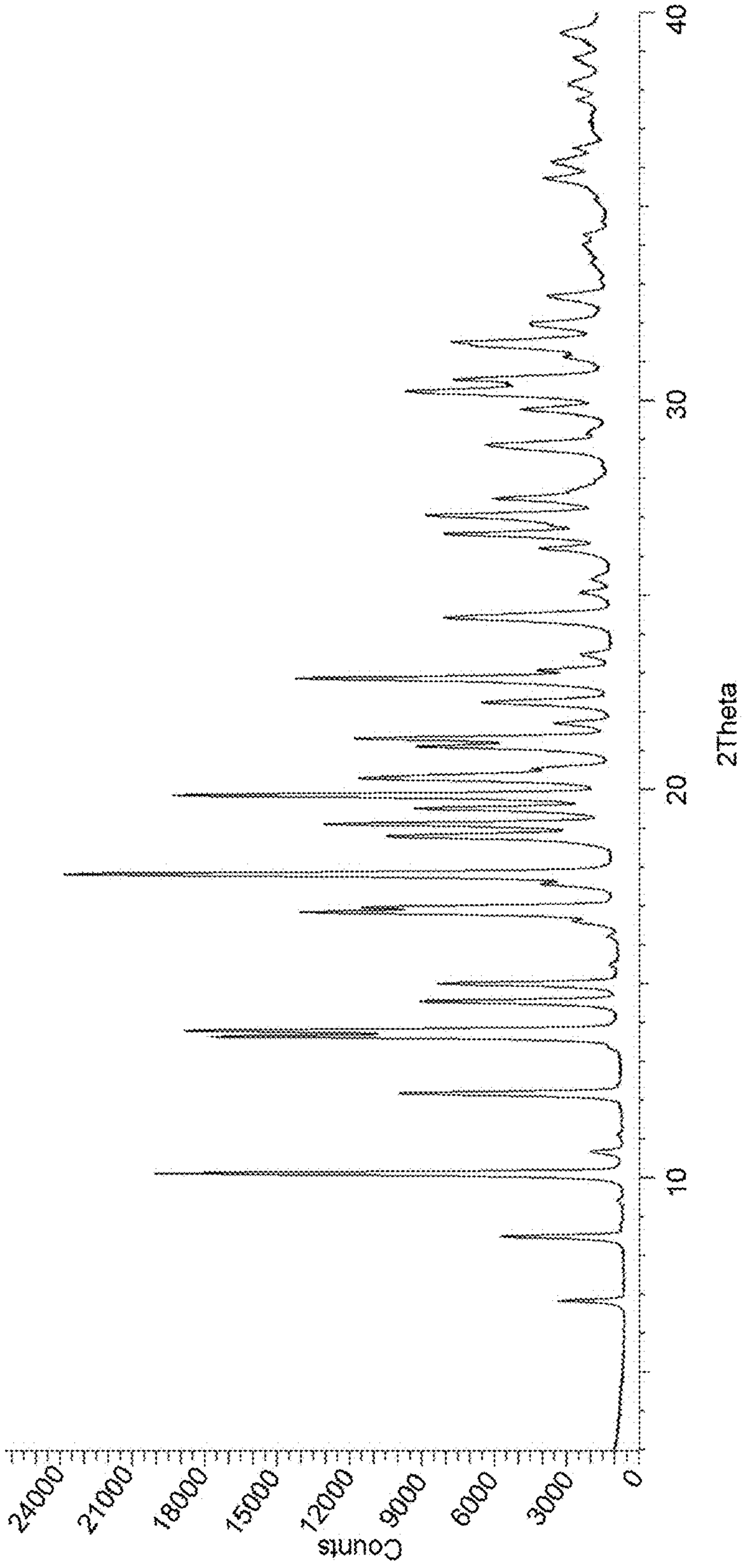
FIG. 13. PXRD pattern of anhydrous crystalline PF-07220060 (Form 6).

FIG. 13 shows PXRD data collected according to General Method 1A. A list of PXRD peaks at diffraction angles 2-Theta ° (° 2θ)±0.2°2θ and their relative intensities is provided in Table 10.

TABLE 10

| PXRD peak list for anhydrous crystalline PF-07220060 (Form 6) (2-Theta °) | |
|---|---|
| Angle (2-theta °) ± 0.2 °2θ | Relative Intensity (%) |
| 6.8 | 12.0 |
| 8.5 | 22.3 |
| 10.1 | 91.1 |
| 10.7 | 4.0 |
| 12.2 | 40.7 |
| 13.6 | 81.4 |
| 13.8 | 79.5 |
| 14.5 | 36.4 |
| 15.0 | 33.2 |
| 16.6 | 5.5 |
| 16.8 | 57.3 |
| 17.0 | 47.5 |
| 17.6 | 13.2 |
| 17.8 | 100.0 |
| 18.8 | 40.9 |
| 19.1 | 52.3 |
| 19.5 | 35.7 |
| 19.9 | 79.8 |
| 20.3 | 45.6 |
| 21.1 | 35.8 |
| 21.3 | 46.4 |
| 21.7 | 9.8 |
| 22.2 | 23.2 |
| 22.9 | 57.1 |
| 24.4 | 30.0 |
| 26.2 | 12.5 |
| 26.6 | 29.9 |
| 27.1 | 32.9 |
| 27.5 | 20.5 |
| 28.9 | 21.9 |
| 29.8 | 14.5 |
| 30.3 | 36.1 |
| 30.6 | 27.4 |
| 31.5 | 23.9 |
| 32.0 | 12.8 |
| 32.7 | 9.6 |
| 35.7 | 10.8 |
| 36.2 | 8.7 |
| 36.5 | 4.6 |
| 37.8 | 3.9 |
| 38.1 | 5.3 |
| 38.8 | 3.8 |
| 39.5 | 6.3 |

FT-Raman Data

Figure 14:
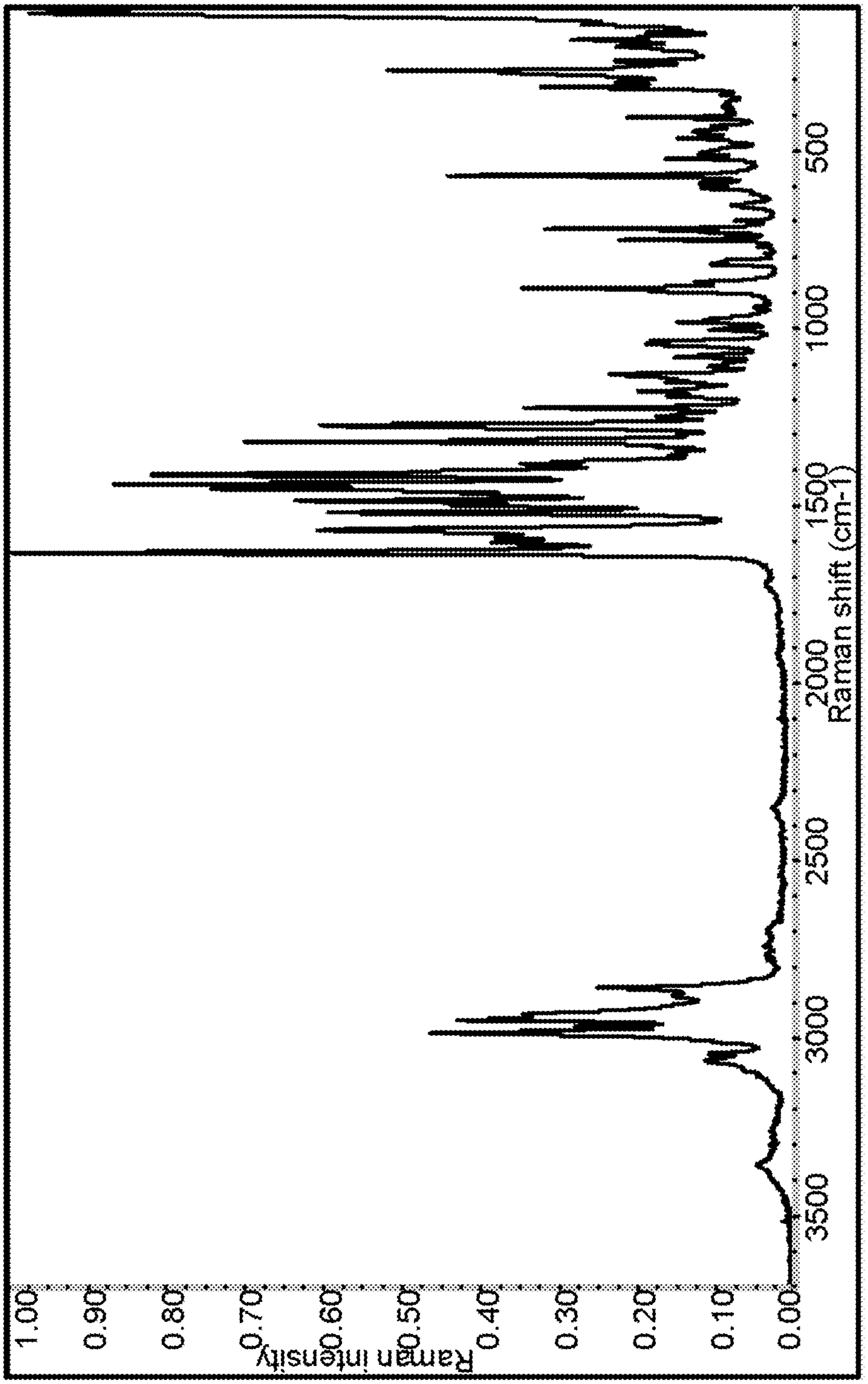
FIG. 14. FT-Raman spectrum of anhydrous crystalline PF-07220060 (Form 6).

FIG. 14 shows the FT-Raman spectrum of anhydrous crystalline PF-07220060 (Form 6), collected according to General Method 2. A full list of FT-Raman peaks ($cm^{-1}$) and qualitative intensities is provided in Table 11 in $cm^{-1}$±2 $cm^{-1}$. Normalized peak intensities are indicated as follows: w=weak; m=medium; s=strong.

TABLE 11

| FT Raman peak list for anhydrous crystalline PF-07220060 (Form 6) ($cm^{-1}$) | | |
|---|---|---|
| Peak position $cm^{-1}$ ± 2 $cm^{-1}$ | Normalized intensity | Classification |
| 202 | 0.22 | w |
| 243 | 0.23 | w |
| 270 | 0.52 | m |
| 303 | 0.23 | w |
| 318 | 0.32 | m |
| 340 | 0.09 | w |
| 371 | 0.09 | w |
| 389 | 0.08 | w |
| 402 | 0.21 | w |
| 427 | 0.10 | w |
| 442 | 0.13 | w |

TABLE 11-continued

| FT Raman peak list for anhydrous crystalline PF-07220060 (Form 6) ($cm^{-1}$) | | |
|---|---|---|
| Peak position $cm^{-1}$ ± 2 $cm^{-1}$ | Normalized intensity | Classification |
| 448 | 0.12 | w |
| 460 | 0.15 | w |
| 504 | 0.12 | w |
| 519 | 0.16 | w |
| 566 | 0.44 | m |
| 588 | 0.12 | w |
| 601 | 0.12 | w |
| 650 | 0.08 | w |
| 693 | 0.07 | w |
| 716 | 0.32 | m |
| 726 | 0.12 | w |
| 748 | 0.22 | w |
| 811 | 0.10 | w |
| 816 | 0.10 | w |
| 865 | 0.13 | w |
| 882 | 0.35 | m |
| 969 | 0.11 | w |
| 978 | 0.15 | w |
| 1000 | 0.11 | w |
| 1033 | 0.18 | w |
| 1042 | 0.19 | w |
| 1077 | 0.15 | w |
| 1104 | 0.11 | w |
| 1124 | 0.23 | w |
| 1149 | 0.16 | w |
| 1173 | 0.20 | w |
| 1187 | 0.16 | w |
| 1220 | 0.34 | m |
| 1245 | 0.17 | w |
| 1268 | 0.60 | m |
| 1295 | 0.15 | w |
| 1316 | 0.70 | m |
| 1330 | 0.18 | w |
| 1346 | 0.15 | w |
| 1356 | 0.16 | w |
| 1377 | 0.35 | m |
| 1384 | 0.28 | w |
| 1409 | 0.82 | s |
| 1436 | 0.87 | s |
| 1450 | 0.74 | m |
| 1465 | 0.42 | m |
| 1481 | 0.63 | m |
| 1494 | 0.43 | m |
| 1515 | 0.59 | m |
| 1566 | 0.61 | m |
| 1583 | 0.38 | m |
| 1599 | 0.38 | m |
| 1629 | 1.00 | s |
| 2853 | 0.25 | w |
| 2876 | 0.15 | w |
| 2928 | 0.34 | m |
| 2944 | 0.43 | m |
| 2962 | 0.28 | w |
| 2981 | 0.46 | m |
| 3038 | 0.11 | w |
| 3060 | 0.11 | w |

ssNMR Data

Figure 15:
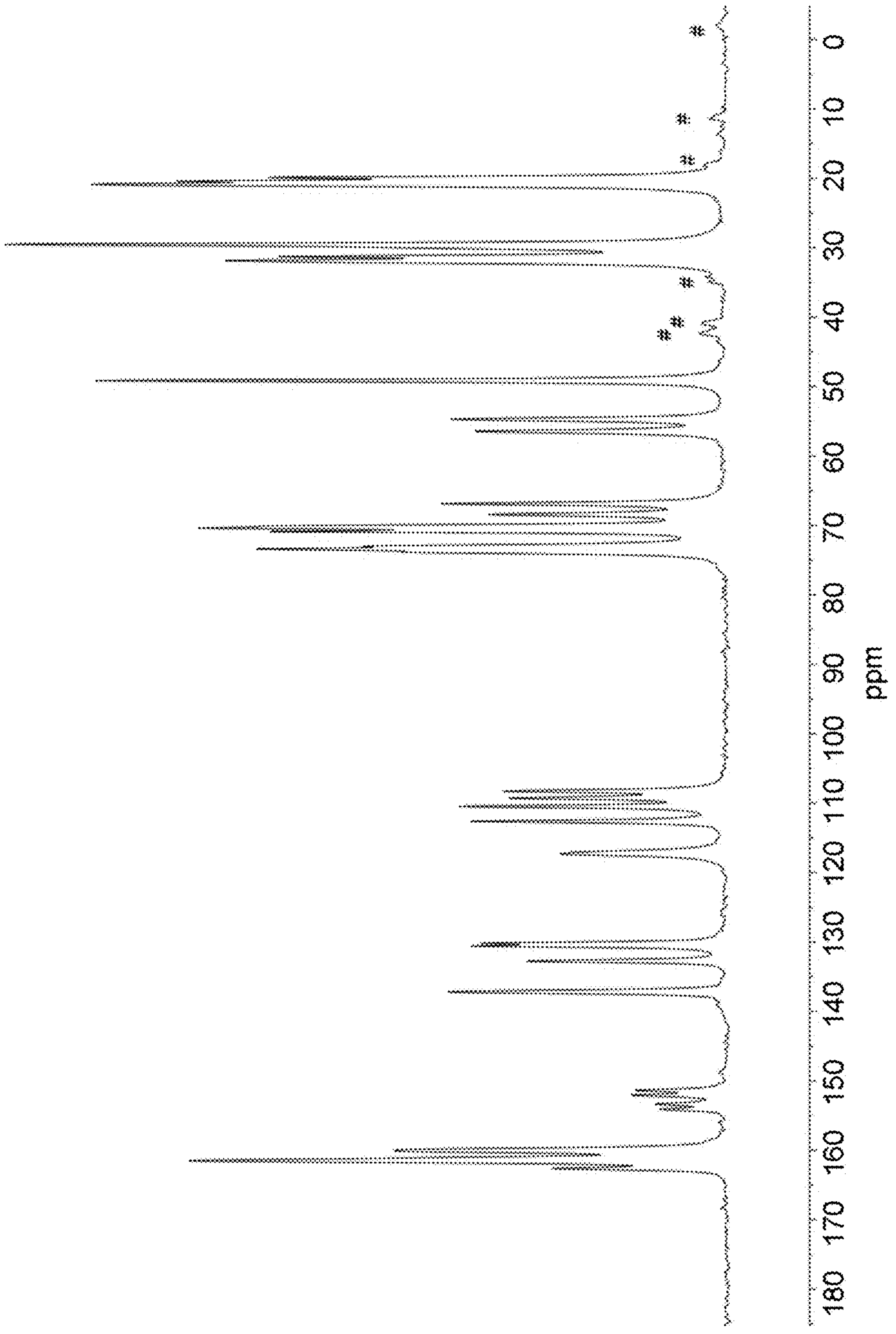
FIG. 15. Carbon CPMAS spectrum of anhydrous crystalline PF-07220060 (Form 6) (# indicates spinning sidebands).

FIG. 15 shows the carbon CPMAS spectrum of anhydrous crystalline PF-07220060 (Form 6), which was collected according to General Method 3. Chemical shifts are expressed in parts per million (ppm) and are referenced to external sample of solid phase adamantane at 29.5 ppm. A list of ssNMR $^{13}C$ chemical shifts (ppm) for Form 6 is provided in Table 12 in ppm±0.2 ppm.

TABLE 12

| ssNMR $^{13}C$ Chemical Shifts for anhydrous crystalline PF-07220060 (Form 6) (ppm) | |
|---|---|
| $^{13}C$ Chemical Shifts ppm ± 0.2 ppm | Relative Intensity (%) |
| 162.6 | 24 |
| 161.5 | 75 |
| 160.0 | 46 |
| 154.1 | 9 |
| 153.4 | 10 |
| 152.1 | 13 |
| 151.4 | 13 |
| 137.2 | 39 |
| 132.8 | 28 |
| 130.6 | 35 |
| 130.2 | 34 |
| 117.3 | 23 |
| 112.6 | 35 |
| 110.5 | 37 |
| 109.3 | 30 |
| 108.3 | 31 |
| 73.8 | 45 |
| 73.4 | 66 |
| 73.0 | 50 |
| 70.9 | 63 |
| 70.4 | 73 |
| 70.1 | 65 |
| 68.4 | 33 |
| 66.9 | 40 |
| 56.5 | 35 |
| 54.7 | 38 |
| 49.2 | 89 |
| 31.9 | 70 |
| 31.3 | 62 |
| 29.6 | 100 |
| 20.9 | 88 |
| 20.5 | 76 |
| 19.9 | 63 |

FIG. 16 shows the $^{19}F$ ssNMR spectrum of anhydrous crystalline PF-07220060 (Form 6), which was collected according to General Method 3. Chemical shifts are expressed in parts per million (ppm) and are referenced to external standard of trifluoroacetic acid and water (50/50 volume/volume), setting its resonance to −76.54 ppm (as determined from neat TMS). A list of ssNMR $^{19}F$ chemical shifts (ppm) for Form 6 is provided in Table 13 in ppm±0.2 ppm.

TABLE 13

| $^{19}F$ solid state NMR peak list for anhydrous crystalline PF-07220060 (Form 6) (ppm). | |
|---|---|
| $^{19}F$ Chemical Shifts ppm ± 0.2 ppm | Relative Intensity (%) |
| −131.1 | 86 |
| −132.4 | 100 |

Example 13

Preparation of Anhydrous Crystalline PF-07220060 (Form 11)

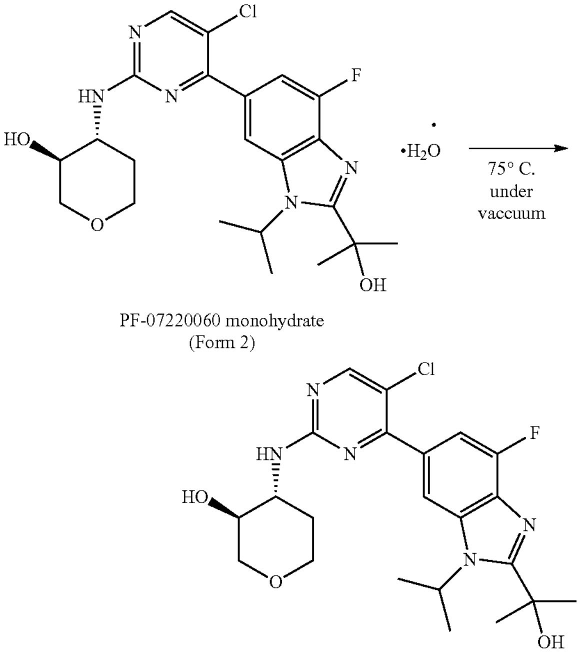

PF-07220060 monohydrate (Form 2)

anhydrous PF-07220060 (Form 11)

PF-07220060 monohydrate (Form 2) (1.8 g), prepared as described in Example 2, was dehydrated under vacuum at 75° C. for 4 days to provide anhydrous crystalline PF-07220060 (Form 11).

Figure 17:
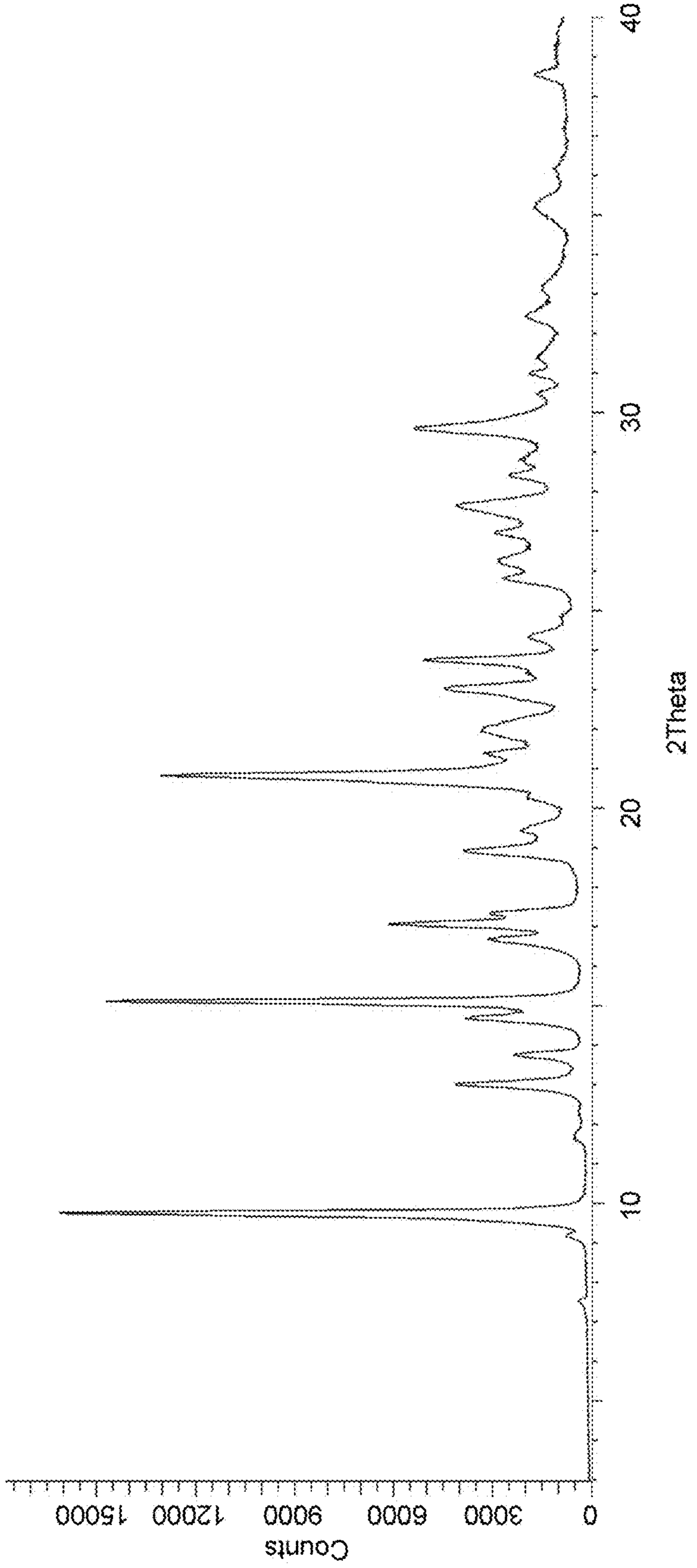
FIG. 17. PXRD pattern of anhydrous crystalline PF-07220060 (Form 11).

Characterization of Form 11 by PXRD:

FIG. 17 shows PXRD data for anhydrous crystalline PF-07220060 (Form 11), collected according to General Method 1A.

Example 14

Solid State Stability Analysis of PF-07220060 Monohydrate (Form 2)

Accelerated solid state chemical stability and photostability of PF-07220060 monohydrate (Form 2) was investigated. Solid state chemical/humidity stability of PF-07220060 monohydrate (Form 2) was evaluated by UPLC (ultra performance liquid chromatography) analysis after storage at 70° C./5% RH and 70° C./75% RH for one week, and at 40° C./5% RH and 40° C./75% RH for 6 weeks. The percentage of identified impurity peaks at the indicated RRT (relative retention time) values were determined under the challenge conditions versus a control sample stored at ambient temperature. RRT is calculated by dividing the retention time (RT) of the impurity by the RT of Form 2. Data at 70° C./5% RH and 70° C./75% RH for one week are provided in Table 14 and Table 15, respectively.

TABLE 14

Stability Testing of PF-07220060 Monohydrate (Form 2) at 70° C./5% RH

| Storage condition | % impurity RRT 0.89 | % impurity RRT 1.31 |
|---|---|---|
| 70° C./5% RH (one week) | 0.57% | 0.99% |
| Control | 0.57% | 1.00% |

TABLE 15

Stability Testing of PF-07220060 Monohydrate (Form 2) at 70° C./75% RH

| Storage condition | % impurity RRT 0.89 | % impurity RRT 1.31 |
|---|---|---|
| 70° C./75% RH (one week) | 0.58% | 1.00% |
| control | 0.57% | 1.00% |

No significant change in appearance was observed in any stressed samples (i.e., at 70° C./75% RH and 70° C./5% RH for one week, or 40° C./75% RH, and 40° C./5% RH for 6 weeks) compared to the control sample. No individual impurities grew by more than 0.2% and total impurities did not exceed 2.0% in the stressed samples.

Powder X-ray diffraction was used to assess the solid form of the control and the stressed samples. No form change was detected upon storage of PF-07220060 monohydrate (Form 2) at 70° C./75% RH for one week or at 40° C./75% RH for six weeks. Slight disorder was observed at 70° C./5% RH for one week and disorder was observed at 40° C./5% RH for six weeks of storage of PF-07220060 monohydrate (Form 2) under conditions of elevated temperature and low humidity.

Solid-state photostability of PF-07220060 monohydrate (Form 2) was evaluated after light exposure equivalent to 2× International Conference on Harmonisation (ICH) guidelines. No significant change in appearance was observed in the 2×CH photostability sample compared to the dark control sample, which was wrapped in foil. No individual impurities grew by more than 0.2% and total impurities did not exceed 2.0% in the 2×CH photostability samples. Powder X-ray diffraction assessment of the control and stressed sample confirmed that there was no form change at 2×CH condition. Photostability data are provided in Table 16.

TABLE 16

Photostability Testing of PF-07220060 Monohydrate (Form 2)

| Storage condition | % impurity RRT 0.74 | % impurity RRT 0.87 | % impurity RRT 1.02 | % impurity RRT 1.33 |
|---|---|---|---|---|
| Dark control | NMT = 0.05% | 0.06% | NMT = 0.05% | 0.08% |
| UV/Fluor | 0.11% | 0.06% | 0.07% | 0.07% |

NMT = Not more than

Example 15

Moisture Sorption Analysis of PF-07220060 Monohydrate (Form 2)

Water sorption and desorption studies of PF-07220060 monohydrate (Form 2), prepared as described in Example 2, were conducted according to General Method 6. Data are provided in Table 17.

TABLE 17

Moisture Sorption Analysis of PF-07220060 monohydrate (Form 2).

| Temperature (° C.) | RH (%) | Weight gain (%) |
|---|---|---|
| 60 | 0 | 0.00 |
| 25 | 0 | 0.00 |
| 25 | 10 | 0.45 |
| 25 | 20 | 0.49 |
| 25 | 30 | 0.51 |
| 25 | 40 | 0.52 |
| 25 | 50 | 0.54 |
| 25 | 60 | 0.56 |
| 25 | 70 | 0.57 |
| 25 | 80 | 0.59 |
| 25 | 90 | 0.62 |
| 25 | 80 | 0.61 |
| 25 | 70 | 0.60 |
| 25 | 60 | 0.60 |
| 25 | 50 | 0.58 |
| 25 | 40 | 0.57 |
| 25 | 30 | 0.56 |
| 25 | 20 | 0.55 |
| 25 | 10 | 0.54 |

Example 16

Moisture Sorption Analysis of PF-07220060 Hydrate (Form 1)

Water sorption and desorption studies of PF-07220060 hydrate (Form 1), prepared as described in Example 5B, were conducted according to General Method 6. Data are provided in Table 18.

TABLE 18

Moisture Sorption analysis of PF-07220060 hydrate (Form 1)

| Temperature (° C.) | RH (%) | Weight gain (%) |
|---|---|---|
| 60 | 0 | 0.00 |
| 25 | 0 | 0.05 |
| 25 | 10 | 1.23 |
| 25 | 20 | 2.34 |
| 25 | 30 | 2.84 |
| 25 | 40 | 3.10 |
| 25 | 50 | 3.26 |
| 25 | 60 | 3.37 |
| 25 | 70 | 3.46 |
| 25 | 80 | 3.53 |
| 25 | 90 | 3.61 |
| 25 | 80 | 3.55 |
| 25 | 70 | 3.49 |
| 25 | 60 | 3.41 |
| 25 | 50 | 3.30 |
| 25 | 40 | 3.13 |
| 25 | 30 | 2.87 |
| 25 | 20 | 2.38 |
| 25 | 10 | 1.26 |

Example 17

Comparative Hygroscopicity Experiments

Comparative hygroscopicity experiments were performed using moisture sorption analysis according to General Method 6. Data are summarized in Table 19. PF-07220060 Forms 1, 2, 6, and 8 were evaluated using moisture sorption at 25° C., 60% RH. A form change at the completion of the run was not detected for any of the forms by PXRD. Form 2 and Form 6 showed reduced hygroscopicity and significantly less weight gain relative to Form 8 and Form 1, which had the highest weight gain.

TABLE 19

Comparative Moisture Sorption Data for Forms 1, 2, 6 and 8

| PF-07220060 In going form | Weight Gain (%) at 25° C., 60% RH |
|---|---|
| Form 1 | ~3 |
| Form 8 | ~2 |
| Form 2 | <1 |
| Form 6 | <1 |

Example 18

Competitive Slurry Experiments

Competitive slurry experiments were performed between Form 1 and Form 2 (Entry 1), and between Form 6 and Form 2 (Entry 2), in 2-propanol/1% water. Data are summarized in Table 20.

Entry 1: PF-07220060 hydrate (Form 1) (64.3 mg), PF-07220060 monohydrate (Form 2) (67.7 mg), 2-propanol (0.990 mL) and water (0.010 mL) were stirred at room temperature for 15 hours. The solids were collected with vacuum filtration and analyzed with PXRD. PXRD data was consistent with PF-07220060 monohydrate (Form 2).

Entry 2: Anhydrous PF-07220060 (Form 6) (56.5 mg), PF-07220060 monohydrate (Form 2) (59.4 mg), 2-propanol (0.990 mL) and water (0.010 mL) were stirred at room temperature for 15 hours. The solids were collected with vacuum filtration and analyzed with PXRD. PXRD data was consistent with PF-07220060 monohydrate (Form 2).

Form 1 and Form 6 converted to Form 2 in competitive slurries in 2-propanol/1% water. Form 2 was thermodynamically stable above 15% RH based on the competition slurry experiments.

TABLE 20

Summary of Competitive Slurry Experiments in 2-propanol/1% water.

| Entry | In-going form | Out-going form |
|---|---|---|
| 1 | Form 1 + Form 2 | Form 2 |
| 2 | Form 6 + Form 2 | Form 2 |

Example 19

Comparative Thermal Stability Experiments

Thermal stability data were obtained through thermogravimetric analysis (TGA) according to General Method 4, and Differential Scanning Calorimetry (DSC) scan according to General Method 5A. Data is shown in Table 21. Form 6 and Form 2 showed improved thermal stability relative to Form 1 and Form 8.

TABLE 21

| Thermal Stability Data for Forms 1, 2, 6 and 8 | | |
|---|---|---|
| PF-07220060 Form | Thermal stability via DSC (° C.) | Thermal stability via TGA (° C.) |
| Form 8 (amorphous) | −10 | 20 |
| Form 1 (hydrate) | 0 | 20 |
| Form 2 (monohydrate) | 50 | 60 |
| Form 6 (anhydrous) | 195 | 195 |

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

The invention claimed is:

1. A crystalline form of 1,5-anhydro-3-({5-chloro-4-[4-fluoro-2-(2-hydroxypropan-2-yl)-1-(propan-2-yl)-1H-benzimidazol-6-yl]pyrimidin-2-yl}amino)-2,3-dideoxy-D-threo-pentitol (PF-07220060) monohydrate (Form 2), having a $^{19}F$ solid state NMR spectrum comprising resonance (ppm) values of: −126.1 and −125.6 ppm±0.2 ppm.

2. A crystalline form of PF-07220060 monohydrate (Form 2), having a powder X-ray diffraction (PXRD) pattern comprising peaks at 2θ values of: 9.6, 11.8 and 14.7°2θ±0.2°2θ.

3. The crystalline form of claim 2, having a PXRD pattern further comprising a peak at a 2θ value of: 12.4°2θ±0.2°2θ.

4. The crystalline form of claim 3, having a PXRD pattern further comprising a peak at a 2θ value of: 21.0°2θ±0.2°2θ.

5. The crystalline form of claim 2, having a Raman spectrum comprising wavenumber ($cm^{-1}$) values of: 1484, 1555 and 1587 $cm^{-1}$±2 $cm^{-1}$.

6. The crystalline form of claim 5, having a Raman spectrum further comprising a wavenumber ($cm^{-1}$) value of: 1387 $cm^{-1}$±2 $cm^{-1}$.

7. The crystalline form of claim 6, having a Raman spectrum further comprising a wavenumber ($cm^{-1}$) value of: 1395 $cm^{-1}$±2 $cm^{-1}$.

8. The crystalline form of claim 2, having a $^{13}C$ solid state NMR spectrum comprising resonance (ppm) values of: 22.8 and 163.0 ppm±0.2 ppm.

9. The crystalline form of claim 8, having a $^{13}C$ solid state NMR spectrum further comprising one, two or three resonance (ppm) values selected from the group consisting of: 50.3, 109.8 and 129.1 ppm±0.2 ppm.

10. The crystalline form of claim 2, having a $^{19}F$ solid state NMR spectrum comprising a resonance (ppm) value of: −126.1 ppm±0.2 ppm.

11. The crystalline form of claim 10, having a $^{19}F$ solid state NMR spectrum further comprising a resonance (ppm) value of: −125.6 ppm±0.2 ppm.

12. A crystalline form of PF-07220060 monohydrate (Form 2), having: (a) a powder X-ray diffraction (PXRD) pattern comprising peaks at 2θ values of: 9.6, 11.8 and 14.7°2θ±0.2°2θ; (b) a Raman spectrum comprising wavenumber ($cm^{-1}$) values of: 1484, 1555 and 1587 $cm^{-1}$±2 $cm^{-1}$; (c) a $^{13}C$ solid state NMR spectrum comprising resonance (ppm) values of: 22.8 and 163.0 ppm±0.2 ppm; or (d) a $^{19}F$ solid state NMR spectrum comprising resonance (ppm) values of: −126.1 and −125.6 ppm±0.2 ppm; or any combination of (a), (b), (c) and (d).

13. An anhydrous crystalline form of PF-07220060 (Form 6), having: (a) a powder X-ray diffraction (PXRD) pattern comprising peaks at 2θ values of: 8.5, 10.1 and 13.8°2θ±0.2°2θ; (b) a Raman spectrum comprising wavenumber ($cm^{-1}$) values of: 1436, 1465 and 1566 $cm^{-1}$±2 $cm^{-1}$; (c) a $^{13}C$ solid state NMR spectrum comprising resonance (ppm) values of: 54.7, 112.6 and 132.8 ppm±0.2 ppm; or (d) a $^{19}F$ solid state NMR spectrum comprising resonance (ppm) values of: −132.4 and −131.1 ppm±0.2 ppm; or any combination of two or more of (a), (b), (c) and (d).

14. An anhydrous crystalline form of PF-07220060 (Form 11), having a powder X-ray diffraction (PXRD) pattern essentially the same as in FIG. 15.

15. The crystalline form of claim 2, wherein the crystalline form is substantially pure.

16. An amorphous form of PF-07220060 (Form 8), having a $^{19}F$ solid state NMR spectrum comprising a resonance (ppm) value of: −127.5 ppm±0.5 ppm.

17. The amorphous form of claim 16, having a $^{13}C$ solid state NMR spectrum comprising resonance (ppm) values of: 20.9, 49.3 and 116.6 ppm±0.5 ppm.

18. The amorphous form of claim 16, having a PXRD peak at diffraction angles (2θ) from about 4 to about 40°2θ±0.5°2θ.

19. A pharmaceutical composition comprising the crystalline form of any one of claims 1 to 11 and 12 to 15, or the amorphous form of any one of claims 16 to 18, and a pharmaceutically acceptable carrier or excipient.

20. A method of treating cancer in a subject in need thereof, comprising administering to the subject a therapeutically effective amount of the crystalline form of any one of claims 1 to 11 and 12 to 15, or the amorphous form of any one of claims 16 to 18; wherein the cancer is breast cancer.

* * * * *